(12) United States Patent
Hsieh et al.

(10) Patent No.: US 9,695,404 B2
(45) Date of Patent: Jul. 4, 2017

(54) GENETICALLY MODIFIED MICROORGANISM FOR PRODUCING LONG-CHAIN DICARBOXYLIC ACID AND METHOD OF USING THEREOF

(71) Applicant: Industrial Technology Research Institute, Hsinchu (TW)

(72) Inventors: Hsin-Ju Hsieh, Hsinchu (TW); Liang-Jung Chien, New Taipei (TW); Jia-Hung Wang, Taichung (TW); Yu-Ju Lin, Zhubei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/802,282

(22) Filed: Jul. 17, 2015

(65) Prior Publication Data

US 2016/0017387 A1    Jan. 21, 2016

Related U.S. Application Data

(60) Provisional application No. 62/026,428, filed on Jul. 18, 2014, provisional application No. 62/032,956, filed on Aug. 4, 2014.

(30) Foreign Application Priority Data

Jun. 30, 2015 (TW) .............................. 104121064 A

(51) Int. Cl.
| | |
|---|---|
| *C12P 7/64* | (2006.01) |
| *C12N 1/20* | (2006.01) |
| *C12N 1/00* | (2006.01) |
| *C12N 1/12* | (2006.01) |
| *C07H 21/04* | (2006.01) |
| *C12N 9/16* | (2006.01) |
| *C12P 7/44* | (2006.01) |

(52) U.S. Cl.
CPC .................. *C12N 9/16* (2013.01); *C12P 7/44* (2013.01); *C12P 7/6418* (2013.01); *C12Y 301/02014* (2013.01)

(58) Field of Classification Search
None
See application file for complete search history.

(56) References Cited

U.S. PATENT DOCUMENTS

| | | | |
|---|---|---|---|
| 4,965,201 A | 10/1990 | Casey et al. | |
| 6,004,784 A | 12/1999 | Mobley et al. | |
| 6,066,480 A | 5/2000 | Mobley et al. | |
| 6,258,288 B1 | 7/2001 | Miyoshi et al. | |
| 8,143,034 B2 | 3/2012 | Gross et al. | |
| 8,158,391 B2 | 4/2012 | Gross et al. | |
| 8,383,373 B2 | 2/2013 | Kamal et al. | |
| 2010/0041115 A1 | 2/2010 | Nicaud et al. | |
| 2011/0118433 A1 | 5/2011 | Potter et al. | |
| 2011/0165637 A1 | 7/2011 | Pfleger et al. | |
| 2013/0197247 A1* | 8/2013 | Franklin | C12N 9/00 554/1 |
| 2013/0267012 A1 | 10/2013 | Steen et al. | |

FOREIGN PATENT DOCUMENTS

| | | |
|---|---|---|
| CN | 1635013 | 7/2005 |
| CN | 1810968 | 8/2006 |
| CN | 1928100 | 3/2007 |
| CN | 102115766 | 7/2013 |
| WO | WO2007096654 A2 | 8/2007 |
| WO | WO2013006733 | 4/2013 |
| WO | WO2013109865 A2 | 7/2013 |

OTHER PUBLICATIONS

Hsieh et al. 2013 2nd International Conference on Environment, Energy and Biotechnology (ICEEB 2013), Jun. 8-9, 2013, Kuala Lumpur, Malaysia, IPCBEE vol. 51, p. 153-156).*
Green, et al., "Candida cloacae oxidation of long-chain fatty acids to dioic acids", Enzyme and Microbial Technology 27 (2000) 205-211.
Jing, et al., "Phylogenetic and experimental characterization of an acyl-ACP thioesterase family reveals significant diversity in enzymatic specificity and activity", BMC Biochemistry 2011, 12:44, pp. 1-16.
Lu, et al., "Biosynthesis of Monomers for Plastics from Renewable Oils", J. Am. Chem. Soc., 2010, 132 (43), pp. 15451-15455.
Smit, et al., "a,w-Dicarboxylic acid accumulation by acyl-CoA oxidase deficient mutants of Yarrowia lipolytica", Biotechnology Letters, Jun. 2005, vol. 27, Issue 12, pp. 859-864.
Smit, et al., "Preparation of dodecanol-tolerant strains of Yarrowia lipolytica", Biotechnol Lett. May 2004;26(10):849-54.
Voelker, et al., "Alteration of the Specificity and Regulation of Fatty Acid Synthesis of *Escherichia coli* by Expression of a Plant Medium-Chain Acyl-Acyl Carrier Protein Thioesterase", Journal of Bacteriology, Dec. 1994,vol. 176, No. 23, p. 7320-7327.
Zibek , et al., "Fermentative Herstellung der α,ω-Dicarbonsäure 1,18-Oktadecendisäure als Grundbaustein für biobasierte Kunststoffe", Chemie Ingenieur Technik 2009, 81, No. 11, 1797-1808.

* cited by examiner

*Primary Examiner* — Iqbal H Chowdhury
(74) *Attorney, Agent, or Firm* — Cesari and McKenna, LLP

(57) ABSTRACT

Described herein are genetically-modified microorganisms for producing long-chain dicarboxylic acids and methods of using the microorganisms. The microorganisms contain a first nucleic acid encoding an *Umbellularia californica* lauroyl ACP-thioesterase (BTE) operably linked to a promoter or a second nucleic acid encoding a *Cocos nucifera* lauroyl ACP-thioesterase (FatB3) operably linked to a promoter.

16 Claims, 17 Drawing Sheets

Co-expression

GENETICALLY MODIFIED MICROORGANISM FOR PRODUCING LONG-CHAIN DICARBOXYLIC ACID AND METHOD OF USING THEREOF

CROSS REFERENCE TO RELATED APPLICATIONS

This application claims priority to U.S. Provisional Application No. 62/026,428, filed on Jul. 18, 2014, U.S. Provisional Application No. 62/032,956, filed on Aug. 4, 2014, and Taiwanese Patent Application No. 104121064, filed on Jun. 30, 2015. The contents of all three prior applications are hereby incorporated by reference herein in their entirety.

BACKGROUND

Long-carbon-chain nylon is a high-performing and high-value chemical material due to its unique thermal, physical, chemical and mechanical properties. Nylon 12 is a specialty resin designated for making fuel lines and brake systems. For high-grade Nylon 12, the price is usually more than 15 euros/kg. Analysis of a fatal explosion at a German plant of the world's largest Nylon 12 supplier, Evonik, revealed that explosion caused by contact between a highly active catalyst (Et2AlCl) and water is a major risk factor. Thus, there is a need for a safe process for producing long-chain dicarboxylic acids.

SUMMARY

In one aspect, described herein is a genetically modified microorganism that contains a first nucleic acid encoding an *Umbellularia californica* lauroyl ACP-thioesterase (BTE) operably linked to a promoter or a second nucleic acid encoding a *Cocos nucifera* lauroyl ACP-thioesterase (FatB3) operably linked to a promoter. The microorganism produces an increased amount of long-chain dicarboxylic acids as compared to the unmodified parent of the microorganism. The genetically modified microorganism can be *Yarrowia lipolytica* or *Escherichia coli*.

The genetically modified microorganism can include one or more further modifications. In one embodiment, it contains one or more additional nucleic acids each operably linked to a promoter, each additional nucleic acid encoding a protein selected from the group consisting of an acetyl-CoA carboxylase (ACC), an acetyl-CoA carboxylase carboxyl transferase subunit α (AccA), an acetyl-CoA carboxylase biotin carboxyl carrier protein (AccB), an acetyl-CoA biotin carboxylase (AccC), an acetyl-CoA carboxylase transferase subunit β (AccD), a fatty acid synthase (FAS) subunit, a cytochrome P450 reductase (CPR), a long-chain alcohol oxidase (FAO1), a long-chain alcohol dehydrogenase (FADH), and an adenosine monophosphate-forming acetyl-coenzyme A synthetase (AceCS). Alternatively or additionally, the genetically modified microorganism can include a loss-of-function mutation in or expresses a lower level of one or more genes selected from the group consisting of a palmitoyl-acyl carrier protein (ACP) thioesterase gene, an acyl-coenzyme A oxidase gene, a citric synthetase (gltA) gene, or an acyl-coenzyme A synthetase (acs) gene.

In another aspect, described herein is a method of producing a long-chain dicarboxylic acid. The method includes culturing the genetically modified microorganism in a culture medium containing glucose or glycerol at pH 6 to 8 under conditions that allow production of a long-chain dicarboxylic acid, whereby the microorganism produces the long-chain dicarboxylic acid. The method can further include collecting the long-chain dicarboxylic acid, e.g., C10-C18 dicarboxylic acid.

The details of one or more embodiments are set forth in the accompanying drawing and the description below. Other features, objects, and advantages of the embodiments will be apparent from the description and drawing, and from the claims.

DETAILED DESCRIPTION

Figure 1:
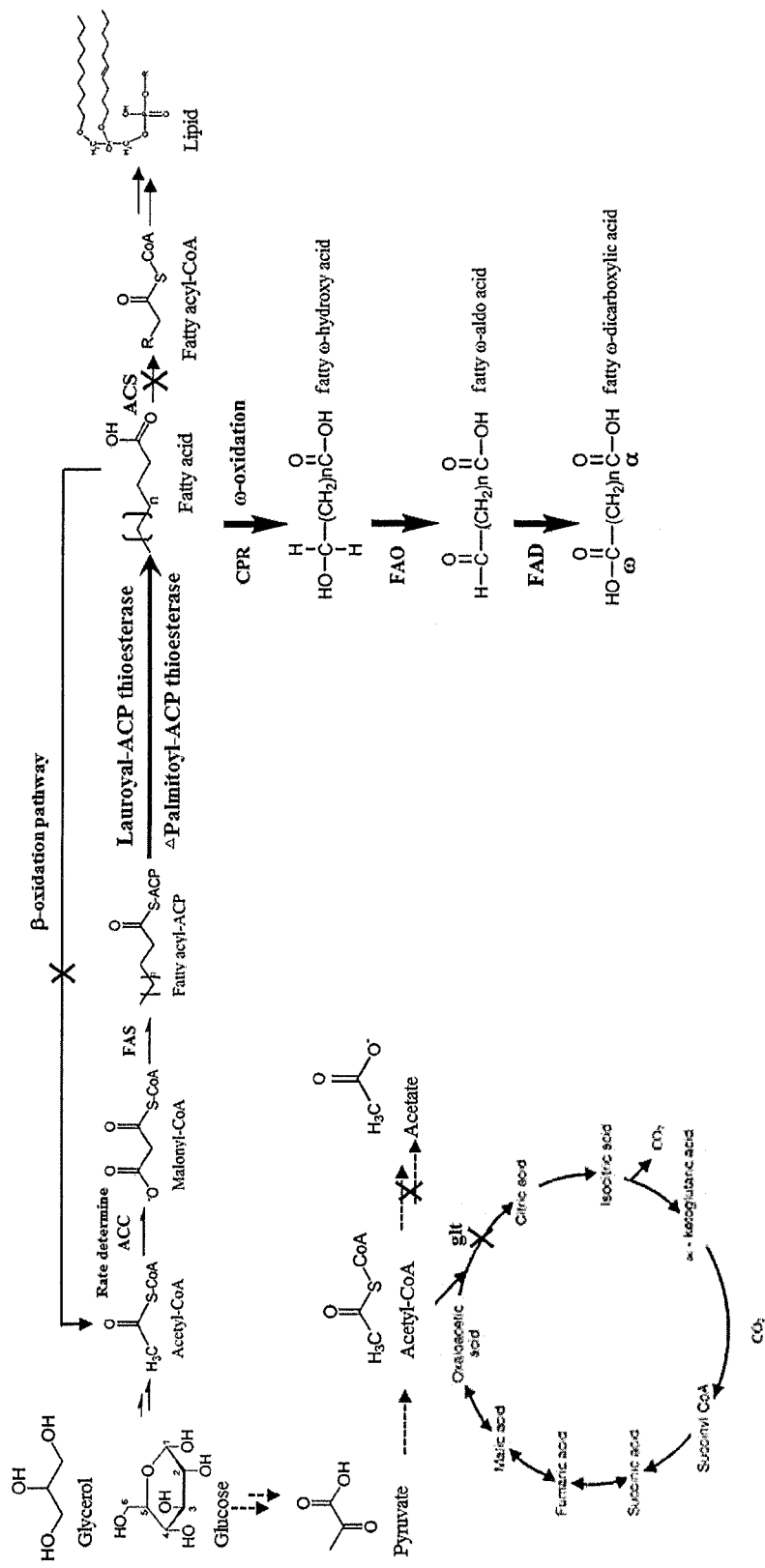
FIG. 1 is a schematic representation showing a modified α,ω-dicarboxylic acid metabolic pathway.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Described below are genetically-modified microorganisms for producing long-chain dicarboxylic acids and methods of using the microorganisms.

To improve production of dicarboxylic acids, one or more modifications can be introduced into the α,ω-dicarboxylic acid metabolic pathway of a microorganism. See FIG. 1. Such modifications can include, for example, increasing free fatty acid contents, enhancing substrate specificity of ω-oxidation enzymes, increasing expression of key proteins in fatty acid synthesis (e.g., acetyl-CoA carboxylase and fatty acid synthase), knocking out a gene upstream of β-oxidation (e.g., pox2, pox5, or fadD), decreasing fatty acid degradation, knocking out a, citric synthetase gene (e.g., gltA), increasing fatty acid synthesis, knocking out an acyl-coenzyme A synthetase gene (e.g., acs), decreasing triglyceride accumulation, increasing expression of an adenosine monophosphate-forming acetyl-coenzyme A synthetase (AceCS), enhancing expression of a lauroyl-ACP thioesterases (e.g., *Cocos nucifera* FatB3 or *Umbellularia californica* BTE), decreasing or silencing expression of a palmitoyl-acyl carrier protein (ACP) thioesterase, and expressing w-oxidation metabolic pathway genes (e.g., cpr, fao1, and fadH).

Accordingly, a genetically-modified microorganism can contain a nucleic acid encoding an *Umbellularia californica* lauroyl ACP-thioesterase (BTE). It can alternatively or further include a nucleic acid encoding a *Cocos nucifera* lauroyl ACP-thioesterase (FatB3).

The genetically-modified microorganism can also have a nucleic acid that encodes an acetyl-CoA carboxylase (ACC), a fatty acid synthase (FAS) subunit, a cytochrome P450 reductase (CPR), a long-chain alcohol oxidase (e.g., FAO1), or a long-chain alcohol dehydrogenase (e.g., FADH).

Each of the above-described nucleic acid is operably linked to a suitable promoter for gene expression in the genetically-modified microorganism. If appropriate or necessary, the sequence of the nucleic acid can also be codon-optimized for expression in the genetically-modified microorganism.

Expression of one or more genes or proteins can also be decreased in the genetically-modified microorganism. For example, the expression of an ACP thioesterase gene, an acyl-coenzyme A oxidase gene (e.g., pox2, pox5, or fadD), a citric synthetase gene (gltA), or an acyl-coenzyme A synthetase gene (acs) can be decreased or silenced in the genetically-modified microorganism. Such a microorganism can have a loss-of-function mutation (e.g., deletion) in the gene or an expression construct that expresses an RNAi molecule targeting the gene.

As used herein, the term "promoter" refers to a nucleotide sequence containing elements that initiate the transcription of an operably linked nucleic acid sequence in a desired host cell. At a minimum, a promoter contains an RNA polymerase binding site. It can further contain one or more enhancer elements which, by definition, enhance transcription, or one or more regulatory elements that control the on/off status of the promoter. A promoter can be an inducible or constitutive promoter. Exemplary promoters include glyceraldehyde-3-phosphate dehydrogenase (GAP), fructose 1,6-bisphosphate aldolase intron (FBAin), beta-lactamase (bla, conferring ampicillin resistance), lac operon, T7, and SP6 promoters.

An expression cassette for expressing any of the genes described above can be introduced into a suitable host cell to produce a genetically modified microorganism using methods known in the art or described herein. Methods known in the art and described below can be used to knock-out a gene or decrease expression of a gene in a host cell to construct the genetically-modified microorganism.

Suitable host cells include, but are not limited to, *Candida tropicalis, Candida cloaceae, Escherichia coli*, and *Yarrowia lipolytica*.

The modified microorganism can then be cultured in a medium suitable for long chain dicarboxylic acid production. For example, the medium can contain glucose or glycerol as a carbon source. After a sufficient culturing period, dicarboxylic acids, in particular DCA12, can be isolated from the medium.

A computer readable file containing a sequence listing is electronically co-filed with this application via EFS-Web. The computer readable file, submitted under 37 CFR §1.821 (e), also serves as the copy required by 37 CFR §1.821(c). The file (filename "28X9833.TXT") was created on Jun. 30, 2015 and has a size of 204,809 bytes. The content of the computer readable file is hereby incorporated by reference herein in its entirety.

Exemplary nucleic acid and amino acid sequences of the proteins described herein are provided in the sequence listing: *Y. lipolytica* acetyl-CoA carboxylase (ACC) (SEQ ID NOs:1 and 2), *E. coli* acetyl-CoA carboxylase carboxyl transferase subunit α (AccA) (SEQ ID NOs: 3 and 4), *E. coli* acetyl-CoA carboxylase biotin carboxyl carrier protein (AccB/BCCP) (SEQ ID NOs:5 and 6), *E. coli* acetyl-CoA biotin carboxylase (AccC) (SEQ ID NOs:7 and 8), *E. coli* acetyl-CoA carboxylase transferase subunit β (AccD) (SEQ ID NOs:9 and 10), *Y. lipolytica* fatty acid synthase subunit α (FASA) (SEQ ID NOs:11 and 12), *Y. lipolytica* fatty acid synthase subunit β (FASB) (SEQ ID NOs:13 and 14), *Y. lipolytica* acetyl-CoA carboxylase transferase subunit β (AccD) (SEQ ID NOs:15 and 16), *Y. lipolytica* fatty acid synthase subunit alpha-active site 1 (FASA-1) (SEQ ID NOs:17 and 18), *Y. lipolytica* codon-optimized *Umbellularia californica* lauroyl ACP-thioesterase (BTE) (SEQ ID NOs: 19 and 20), *E. coli* codon-optimized BTEΔNC (SEQ ID NOs:21 and 22), *Y. lipolytica* codon-optimized *Cocos nucifera* lauroyl palmitoyl-acyl carrier protein (ACP) thioesterase (FatB3) (SEQ ID NOs:23 and 24), *E. coli* codon-optimized FatB3ΔNC (SEQ ID NOs:25 and 26), *Y. lipolytica* ACP thioesterase (SEQ ID NOs:27 and 28), *Candida tropicalis* cytochrome P450 reductase (CPR/CTP 00485) (SEQ ID NOs:29 and 30), *E. coli* codon-optimized *Candida tropicalis* CPR nucleic acid sequence (SEQ ID NO: 31), *Candida albicans* fatty alcohol oxgenase (FAO1) (SEQ ID NOs:32 and 33), *E. coli* codon-optimized *Candida albicans* FAO1 nucleic acid sequence (SEQ ID NO:34), *Candida albicans* fatty aldehyde hydrogenase (FADH) (SEQ ID Nos:35 and 36), *E. coli* codon-optimized *Candida albicans* FADH (SEQ ID NO:37), *Y. lipolytica* acyl-coenzyme A oxidase (PDX2) (SEQ ID NOs:38 and 39), *Y. lipolytica* acyl-coenzyme A oxidase (PDX5) (SEQ ID NOs:40 and 41), *E. coli* acyl-coenzyme A oxidase (FadD) (SEQ ID NOs:42 and 43), *E. coli* adenosine monophosphate-forming acetyl-CoA synthetase (AceCS) (SEQ ID NOs:44 and 45), *E. coli* acyl-CoA synthetase (ACS) (SEQ ID NOs:46 and 47), and *E. coli* citric synthetase (gltA) (SEQ ID NOs:48 and 49).

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

Modified *Y. lipolytica* Strains

Figure 2:
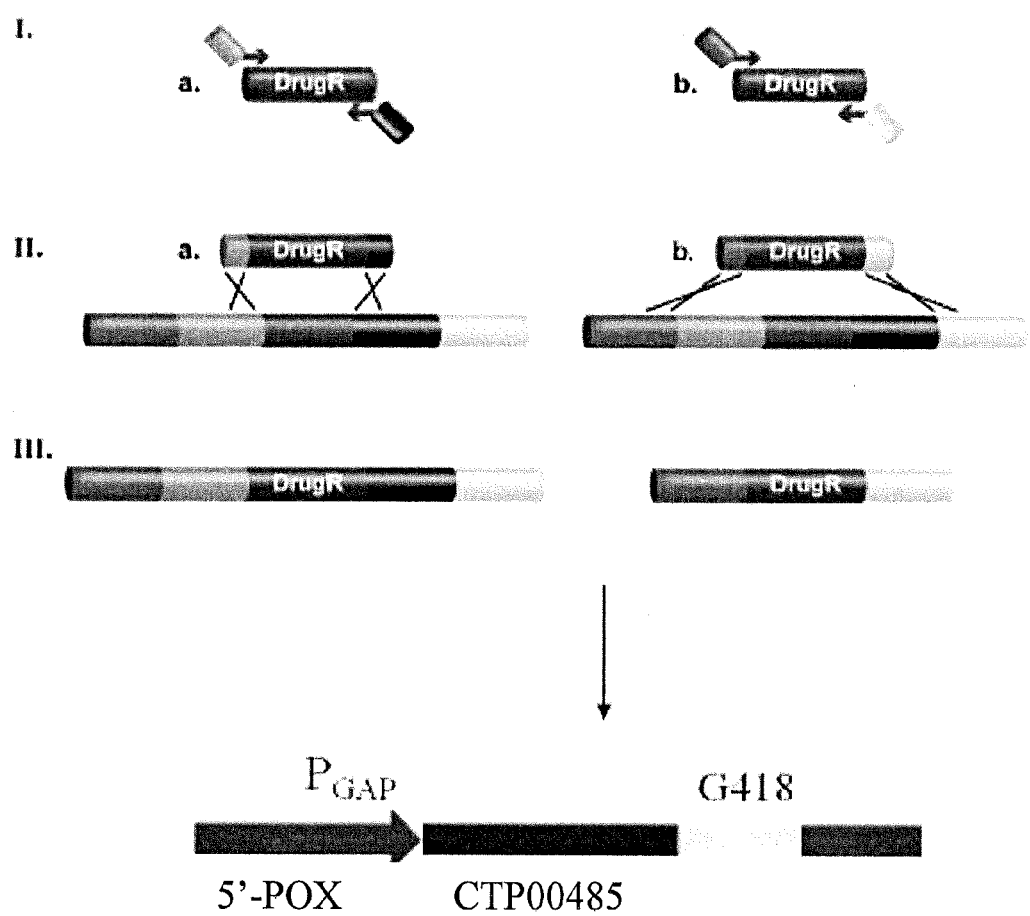
FIG. 2 is a schematic diagram showing construction of a modified *Y. lipolytica* strain.

Since *Yarrowia* and *Pichia* expression systems are similar, the *Yarrowia* expression system used in this study was design based on a *Pichia pastoris* expression system. A construct for single/double-crossover homologous recombination was designed to insert a co-oxidation gene into the acyl coenzyme A oxidase gene (pox1-5) of a *Yarrowia* strain in order to knock out the β-oxidation activity of the strain. Geneticin was used as the selectable marker. A schematic diagram of the construct is shown in FIG. 2.

Splice overlap extension (SOE) polymerase chain reaction (PCR) was used to generate a fusion construct containing pox2 or pox5 and a selectable marker (Kan::G418). See FIG. 2. The fusion construct was cloned into the pUC19 vector. The fusion construct was used to generate pox2- and pox5-deficient strains. Our analysis showed that this strategy significantly reduced unnecessary strain replication and DNA purification steps. The PCR product was used directly to efficiently transform a strain.

The electroporation method was used to introduce constructs into cells. First, Y. lipolytica cells were incubated in TE/LiAc/$H_2O$ for 30 minutes, and then washed with Sorbitol to obtain competent Y. lipolytica cells. Constructs were then introduced into the cells via electroporation. 50-500 μg/mL Geneticin was used to select for antibiotic-resistant transformants.

Y. lipolytica cells were cultured under various conditions in different media, i.e., YNB medium (0.17% YNB without amino acid, 0.5% ammonium sulphate, glucose or glycerol, 0.15% Yeast extract, 0.5% NH4Cl, 0.01% Uracil, 2% Casamino acids, and 0.02% Tween-80) and NL medium (10% Glucose, 0.85% Yeast extract, and 0.3% Peptone). The cells and culturing media were collected for analysis using gas chromatography (GC) or high-performance liquid chromatography (HPLC).

For GC, a 5 mL culture sample was adjusted to pH 10.0 and then centrifuged. The supernatant was collected and the pH was adjusted to pH 2.0. The pellet was also collected. 14% BF3-Methanol (0.1 mL) and 0.2 mL Hexane was added to the sample and heated at 80-90° C. for 60 minutes. 0.2 mL of saline solution was added, and then 0.5 mL Hexane was added. GC analysis was then performed on the sample.

Figure 3:
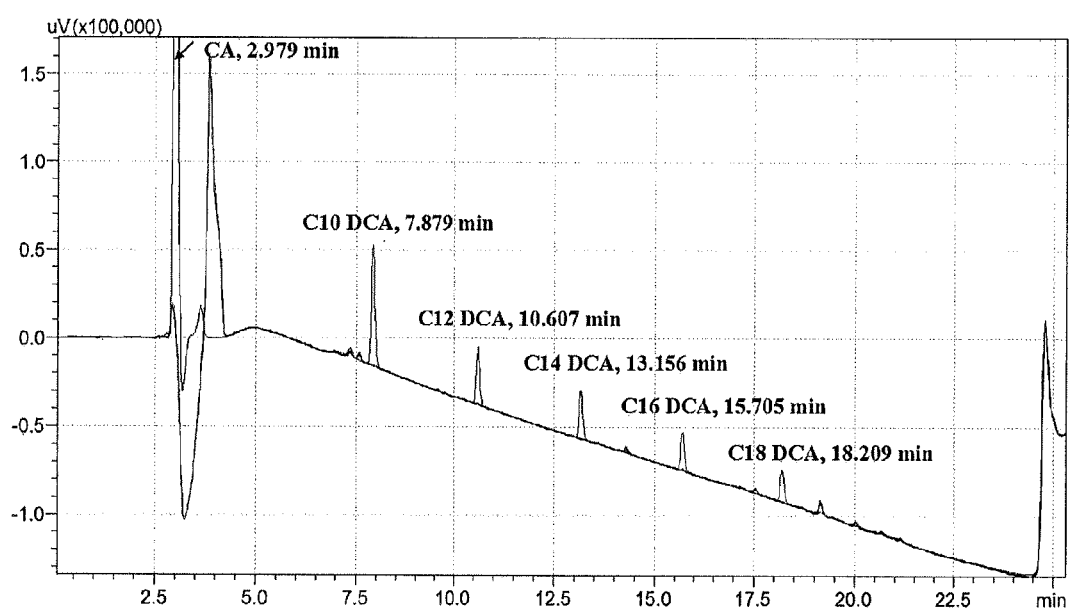
FIG. 3 is a graph showing HPLC analysis of dicarboxylic acid samples.

For HPLC, 5 mL of ethyl acetate was added to 5 mL of culture. The culture was then subjected to a Beatbeader sonicator for about one minute to break the cells and then centrifuged at 6000 rpm. The supernatant was collected. The solvent was allowed to evaporate from the supernatant. 1 mL of 99.5% ethanol was added to dissolve the extract. The sample was then analyzed by HPLC. See FIG. 3.

| Instrument: | Shimadzu 20ALC |
| --- | --- |
| Column: | Vercogel 120-5 C8, 5 um, 4.6 × 250 mm (Vercopak no. 15835) |
| Eluent: | A: 0.1% TFA in $H_2O$ |
| | B: AeCN |

| Gradient: | Time | % A | % B |
| --- | --- | --- | --- |
| | 0 | 70 | 30 |
| | 20 | 0 | 100 |
| | 22 | 70 | 30 |
| Flow rate: | 1.0 ml/min | | |
| Column oven: | 30° C. | | |
| Detection: | UV 220 nm | | |
| Samples: | Citric acid (CA), Sebacic acid (C10 DCA), Dodecanedioic acid (C12 DCA), Tetradecanedioic acid (C14 DCA), Hexadecanedioic acid (C16 DCA), Octanedecanedioic acid (C18 DCA) | | |
| Injection: | 10 μl | | |

Figure 4:
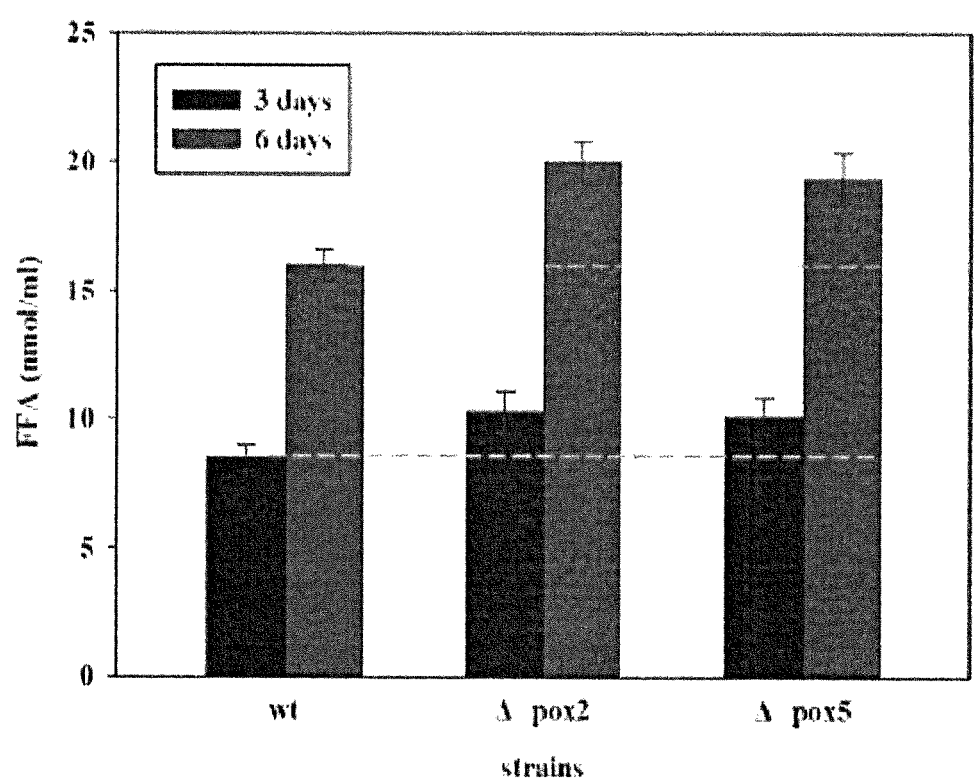
FIG. 4 is a graph showing the fatty acid contents of Δpox2 and Δpox5 mutants.

Our data showed that a pox2-deficient Y. lipolytica mutant accumulated more fatty acids than a pox5-deficient Y. lipolytica mutant. There was a 20% increase as compared to the wild-type. See FIG. 4.

Wild-type Y. lipolytica was cultured in YPD medium for one day, and then inoculated into 250 ml of YNB medium (10% glucose or glycerol) at an initial pH of 6.18 or 6.42. The cells were then cultured in a shaker bottle for 5 days without controlling the pH. Dicarboxylic acid production was measured. See Table 1.

TABLE 1

| Day | pH | Residual glu (g/L) | C10DCA (g/L) | C12DCA (g/L) | C14DCA (g/L) | C16DCA (g/L) |
| --- | --- | --- | --- | --- | --- | --- |
| D5 | 3.38 | 0 | 0.40 | — | 0.25 | — |
| | | Residual gly (g/L) | | | | |
| D5 | 3.19 | 0 | 0.47 | — | — | — |

Figure 5:
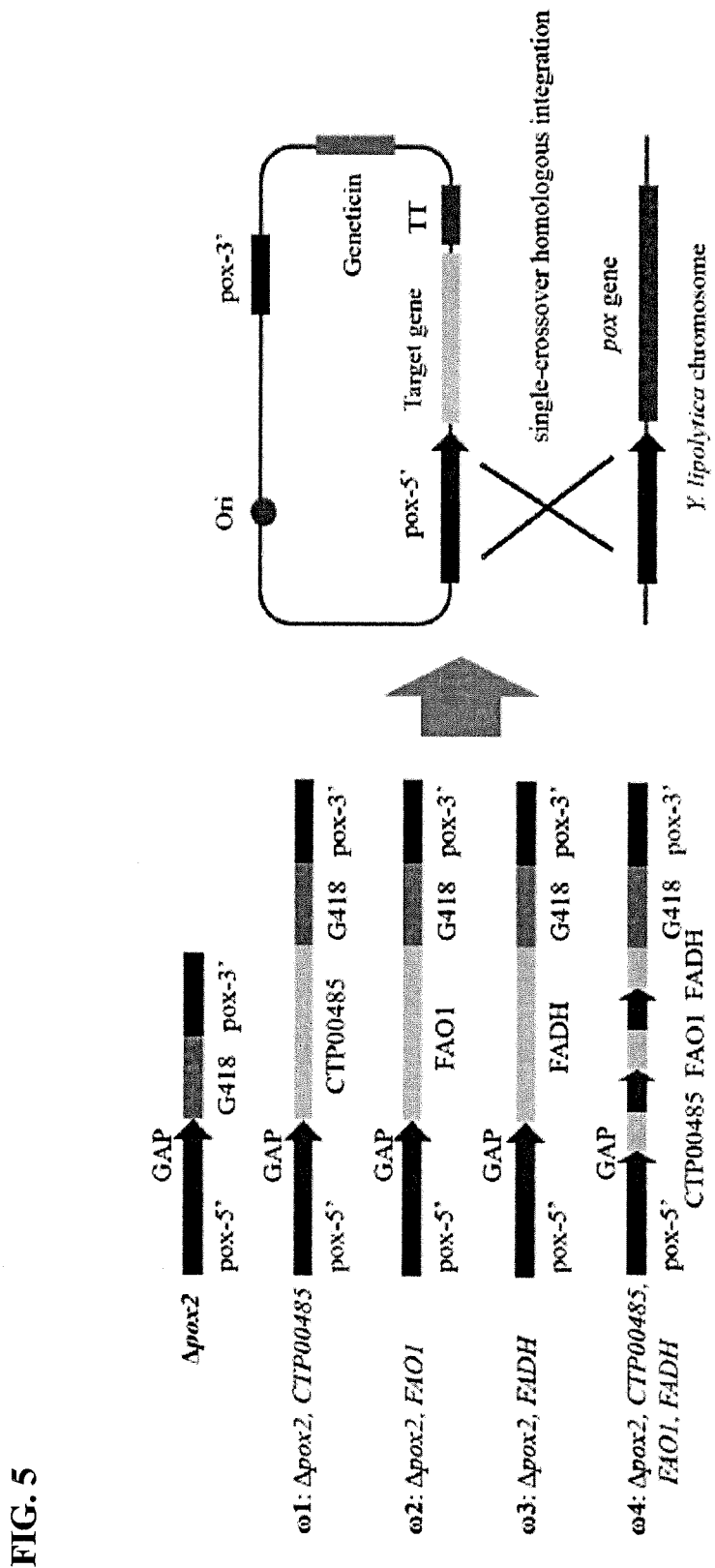
FIG. 5 is a schematic diagram showing construction of various modified *Y. lipolytica* strains.

Four Y. lipolytica strains (ω1, ω2, ω3, and ω4) were constructed using the targeted gene knockout method described above. See FIG. 5.

Strain ω4 was cultured in YPD medium for one day, inoculated into 500 ml of NL medium at an initial pH of 5.0, and then cultured in a fermenter without controlling the pH. Dicarboxylic acid production was measured. See Table 2.

TABLE 2

| Day | pH | Residual glu (g/L) | C10DCA (g/L) | C12DCA (g/L) | C14DCA (g/L) | C16DCA (g/L) |
| --- | --- | --- | --- | --- | --- | --- |
| D2 | 4.22 | 84.3 | 0.28 | 0.37 | 1.02 | — |
| D3 | 3.19 | 45.0 | 0.45 | 0.40 | 1.02 | — |
| D4 | 3.34 | 0 | 0.37 | 0.49 | 0.88 | — |
| D5 | 4.91 | 0 | 0.43 | 0.52 | 1.09 | — |
| | | Residual gly (g/L) | | | | |
| D2 | 3.45 | 94 | 0.24 | 0.08 | 1.06 | — |
| D3 | 2.37 | 37 | 0.23 | 0.57 | 0.85 | — |

Figure 6:
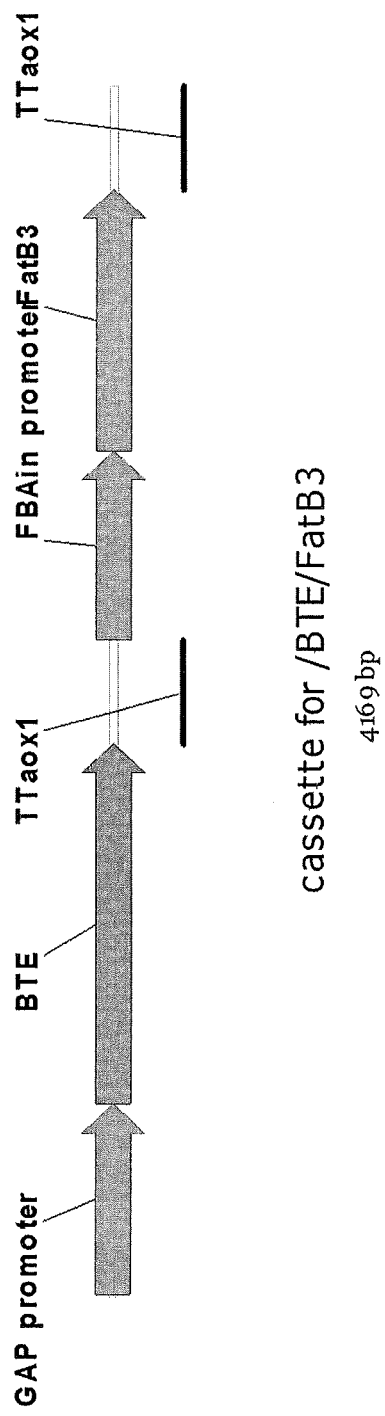
FIG. 6 is a schematic diagram showing an expression cassette for expressing an *Umbellularia californica* lauroyl ACP-thioesterase (BTE) and a *Cocos nucifera* lauroyl ACP-thioesterase (FatB3).

We constructed three additional Y. lipolytica strains, each expressing a lauroyl ACP-thioesterase (BTE, from *Umbellularia californica*), a lauroyl ACP-thioesterase (FatB3, from *Cocos nucifera*), or both. See FIG. 6.

TABLE 3

| | Relative fatty acid content (%) | | | | | | | | |
| --- | --- | --- | --- | --- | --- | --- | --- | --- | --- |
| Sample | C8:0 | C10:0 | C12:0 | C14:0 | 16:0 | 18:0 | 18:1 | 18:2 | 18:3 |
| Wild-type[1] | — | 7.1 | 6.3 | 5.9 | 19.2 | 28.6 | 23.1 | 5.6 | 2.1 |
| WT-B[1] | — | 7.1 | 6.8 | 7.5 | 19.5 | 26.9 | 22.3 | 5.8 | 2.5 |
| WT-F[1] | — | 6.9 | 7.1 | 7.8 | 18.5 | 27.1 | 21.8 | 6.4 | 2.4 |
| WT-B/F[1] | — | 7 | 13.5 | 6.8 | 16.5 | 23.7 | 19.5 | 5.4 | 3.2 |
| Wild-type[2] | — | 6.5 | 8.1 | 5.8 | 21.2 | 26.5 | 22.1 | 5.1 | 3.2 |

TABLE 3-continued

| | Relative fatty acid content (%) | | | | | | | | |
|---|---|---|---|---|---|---|---|---|---|
| Sample | C8:0 | C10:0 | C12:0 | C14:0 | 16:0 | 18:0 | 18:1 | 18:2 | 18:3 |
| WT-B[2] | — | 7.6 | 10.25 | 8.1 | 17.5 | 23.5 | 21.5 | 6.1 | 3.7 |
| WT-F[2] | — | 7.2 | 15.2 | 7.8 | 15.6 | 20.1 | 20.3 | 7.1 | 2.4 |
| WT-B/F[2] | — | 6.9 | 24.6 | 6.8 | 13.5 | 18.5 | 19.2 | 5.7 | 3.3 |
| Wild-type[3] | — | 6.6 | 10.2 | 5.9 | 20.5 | 25.6 | 21.1 | 4.9 | 3.9 |
| WT-B[3] | — | 6.3 | 16.5 | 8.9 | 16.2 | 20.5 | 21.5 | 5.6 | 3.7 |
| WT-F[3] | — | 7.5 | 21.5 | 7.5 | 13.4 | 17.6 | 20.7 | 6.7 | 3.2 |
| WT-B/F[3] | — | 7.1 | 29.5 | 5.9 | 10.2 | 15.9 | 20.3 | 7.1 | 3.3 |

WT-B: expresses BTE,
WT-F: expresses FatB3,
WT-B/F: expresses BTE and FatB3
[1]NL medium;
[2]BMGY medium at day 3;
[3]BMGY medium at day 7

The strains were cultured in YPD medium for one day, inoculated into 250 ml of NL or BMGY medium (2% Peptone, 1% yeast extract, 100 mM potassium phosphate pH 6.0, 1.34% yeast nitrogen base (w/o amino acids), 0.4 μg/mL biotin, and 1% glycerol), and then cultured in a shaker bottle for 7 days. Free fatty acid production was then measured. See Table 3.

We also constructed strain ω5 (deposited at the Bioresource Collection and Research Center in Taiwan on Dec. 10, 2014 as BCRC 920096) by introducing the BTE and FatB3 genes into strain ω4. Strain ω5 was cultured in YNB medium at an initial pH of 6.18, and then cultured in a fermenter for 6 days without controlling the pH. Dicarboxylic acid production was then measured. See Table 4.

TABLE 4

| Day | pH | Residual glu (g/L) | C10DCA (g/L) | C12DCA (g/L) | C14DCA (g/L) | C16DCA (g/L) |
|---|---|---|---|---|---|---|
| D2 | 6.16 | 94.7 | 0.50 | — | 0.86 | — |
| D3 | 3.17 | 11.8 | 0.30 | — | 0.73 | — |
| D4 | 3.71 | 0 | 0.36 | 0.31 | 0.68 | — |
| D5 | 3.75 | 0 | 0.31 | 0.27 | 0.51 | — |
| D6 | 3.38 | 0 | 0.64 | 0.53 | 0.99 | — |

Figure 7:
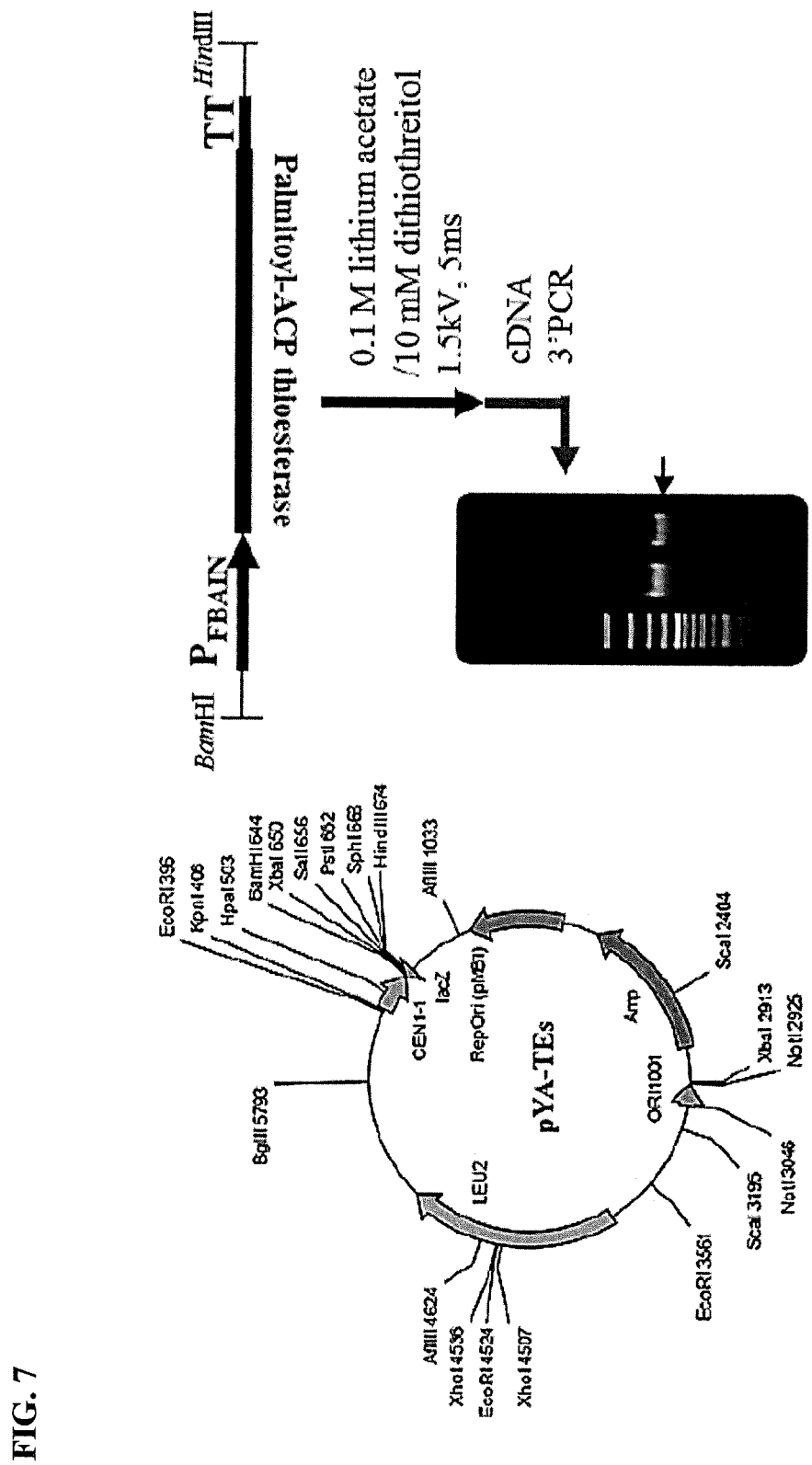
FIG. 7 is a schematic diagram showing construction of an RNAi expression cassette for silencing expression of the palmitoyl-acyl carrier protein (ACP) thioesterase gene.

In order to decrease DCA12 degradation, we constructed strain ω6 (ω5::Δ palmitoyl ACP-thioesterase; deposited at the Bioresource Collection and Research Center in Taiwan on Dec. 10, 2014 as BCRC 920097) using RNA interference. See FIG. 7.

TABLE 5

| Day | pH | Residual glu (g/L) | C10DCA (g/L) | C12DCA (g/L) | C14DCA (g/L) | C16DCA (g/L) |
|---|---|---|---|---|---|---|
| D2 | 4.24 | 58 | 1.90 | — | — | — |
| D3 | 3.35 | 0.2 | 0.50 | — | — | — |
| D4 | 2.85 | 0 | 0.52 | — | — | — |
| D5 | 3.85 | 0 | 0.71 | 0.58 | — | — |

Strain ω6 was cultured in YNB medium at an initial pH of 6.18, and then cultured in a shaker bottle for 5 days without controlling the pH. Dicarboxylic acid production was measured. See Table 5.

Figure 8:
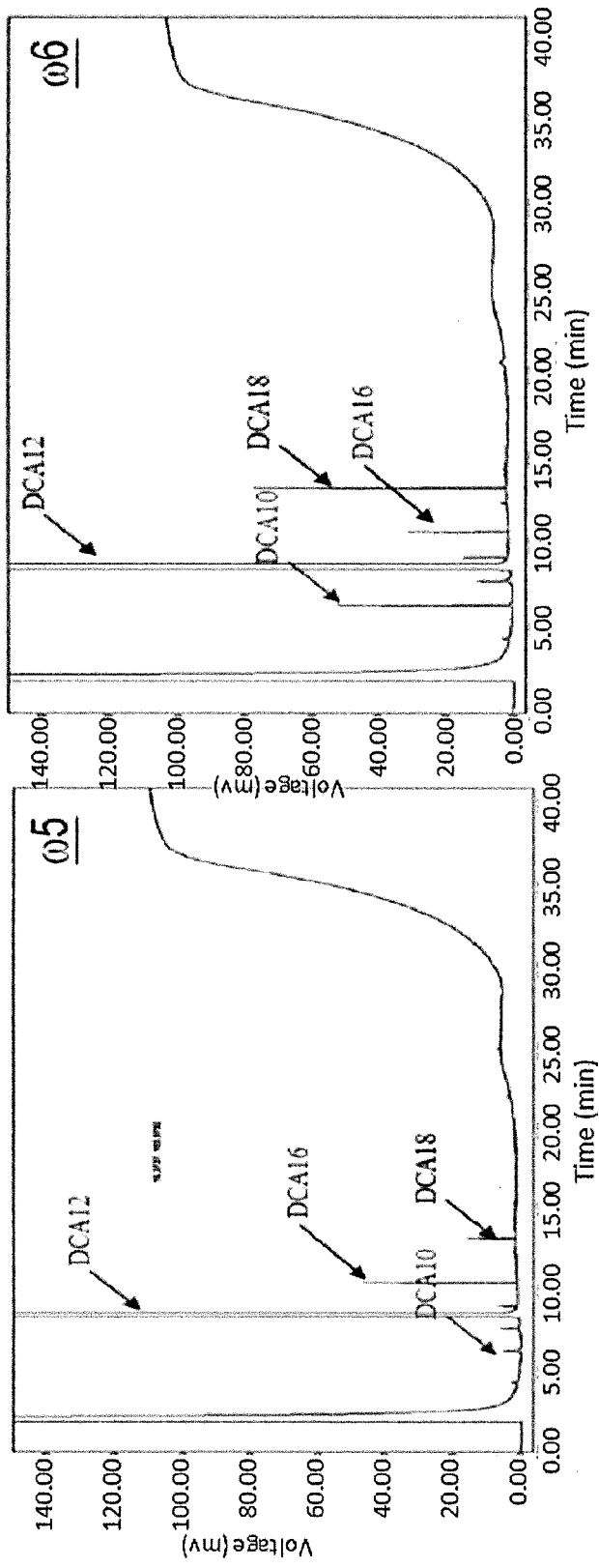
FIG. 8 is a set of graphs showing dicarboxylic acids produced by two modified *Y. lipolytica* strains.

Strains ω5 and ω6 were cultured in YPD medium for one day, and then inoculated into 250 ml of YNB medium (2% glucose) in a shaker bottle. The pH was maintained at 6.0 for two days. Additional 2% glucose was then added every 6 hours to maintain the pH at 7.5 for 5 days. For strain ω5, production of DCA12 increased from 12.9% to 51.2% (1.23 g/L) as compared to strain ω4. For strain ω6, DCA12 production was increased to 59.8% (2.35 g/L). See FIG. 8 and Table 6.

TABLE 6

| Strain | C10DCA | C12DCA | C14DCA | C16DCA |
|---|---|---|---|---|
| ω5 | 9.2 | 51.2 | 23.7 | 15.9 |
| ω6 | 11.1 | 59.8 | 10.9 | 18.2 |

We constructed strain ω7 (ω6::AccD::FASA-1; deposited at the Bioresource Collection and Research Center in Taiwan on Dec. 10, 2014 as BCRC 920098). Strain ω7 was cultured in YNB medium for 6 days without controlling the pH. Dicarboxylic acid production was measured. See Table 7.

TABLE 7

| Day | pH | Residual glu (g/L) | C10DCA (g/L) | C12DCA (g/L) | C14DCA (g/L) | C16DCA (g/L) |
|---|---|---|---|---|---|---|
| D2 | 4.24 | 93 | 1.69 | — | 0.29 | 0.27 |
| D3 | 3.35 | 21 | 0.15 | — | 0.41 | 0.73 |
| D4 | 2.85 | 0 | 0.49 | 0.46 | 0.62 | 0.48 |
| D5 | 3.85 | 0 | 0.53 | 0.47 | 0.62 | 0.48 |
| D6 | 5.47 | 0 | 0.52 | 0.58 | 0.62 | 0.46 |

Strain ω7 was cultured in YNB medium in a fermentor under 1 vvm aeration and at 300 rpm. The pH was maintained at 6.0 for the first two days, and then every 6 hours, additional 2% glucose was added to maintain the pH at 6.0 for additional 5 days. Dicarboxylic acid production was measured. See Table 8.

TABLE 8

| Day | C10DCA (g/L) | C12DCA (g/L) | C14DCA (g/L) | C16DCA (g/L) | C18DCA (g/L) |
|---|---|---|---|---|---|
| D 0 | 0.24 | 0.21 | 0.15 | 0.17 | 0.10 |
| D 1 | 0.45 | 0.38 | 0.18 | 0.26 | 0.18 |
| D 2 | 0.77 | 0.45 | 0.27 | 0.35 | 0.16 |
| D 3 | 0.53 | 0.72 | 0.32 | 0.39 | 0.17 |
| D 4 | 0.48 | 1.11 | 0.41 | 0.43 | 0.15 |
| D 5 | 0.32 | 1.19 | 0.49 | 0.45 | 0.21 |

Strain ω7 was cultured in YNB medium in a fermentor under 1 vvm aeration and at 300 rpm. The pH was maintained at 6.0 for the first two days, and then every 6 hours, additional 2% glucose was added to maintain the pH at 7.5 for additional 5 days. Dicarboxylic acid production was measured. See Table 9.

TABLE 9

| Day | C10DCA (g/L) | C12DCA (g/L) | C14DCA (g/L) | C16DCA (g/L) | C18DCA (g/L) |
|---|---|---|---|---|---|
| D 0 | 0.27 | 0.26 | 0.12 | 0.18 | 0.14 |
| D 1 | 0.30 | 0.49 | 0.23 | 0.15 | 0.12 |
| D 2 | 0.76 | 1.01 | 0.53 | 0.14 | 0.22 |
| D 3 | 0.84 | 1.51 | 0.74 | 0.21 | 0.32 |
| D 4 | 0.67 | 2.23 | 1.26 | 0.27 | 0.34 |
| D 5 | 0.60 | 2.78 | 1.47 | 0.43 | 0.41 |

Modified *E. coli* Strains

Modified *E. coli* strains were constructed using expression vectors to express certain proteins. To eliminate the β-oxidation activity of the strains, the fadD gene was deleted. The ΔfadD strain was used as the host strain to construct strains E1, E2, E3, E4, E5, and E6.

Figure 9:
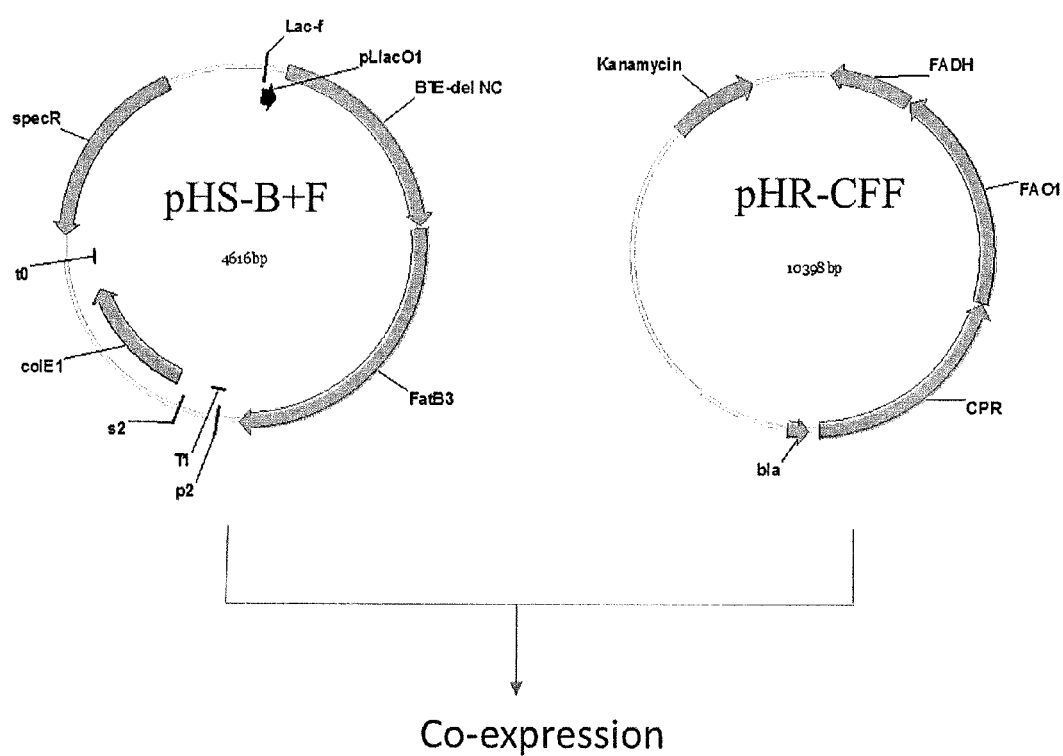
FIG. 9 is a schematic diagram showing expression constructs for generating modified *E. coli* strain E1.

We constructed strain E1 (ΔfadD::BTEΔNC::FatB3::CPR::FAO::FADH). The BTEΔNC and FatB3 genes were inserted into the Acc65I/SalI and HindIII/BamHI sites in the pHS vector, respectively. The CPR, FAO, and FADH genes were inserted into the BamHI/EcoRI, SalI/HindIII, and XhoI sites in the pHR vector, respectively. The resulting expression constructs (pHS-B+F and pHR-CFF) were introduced into host *E. coli* cells to generate strain E1. See FIG. 9.

Figure 10:
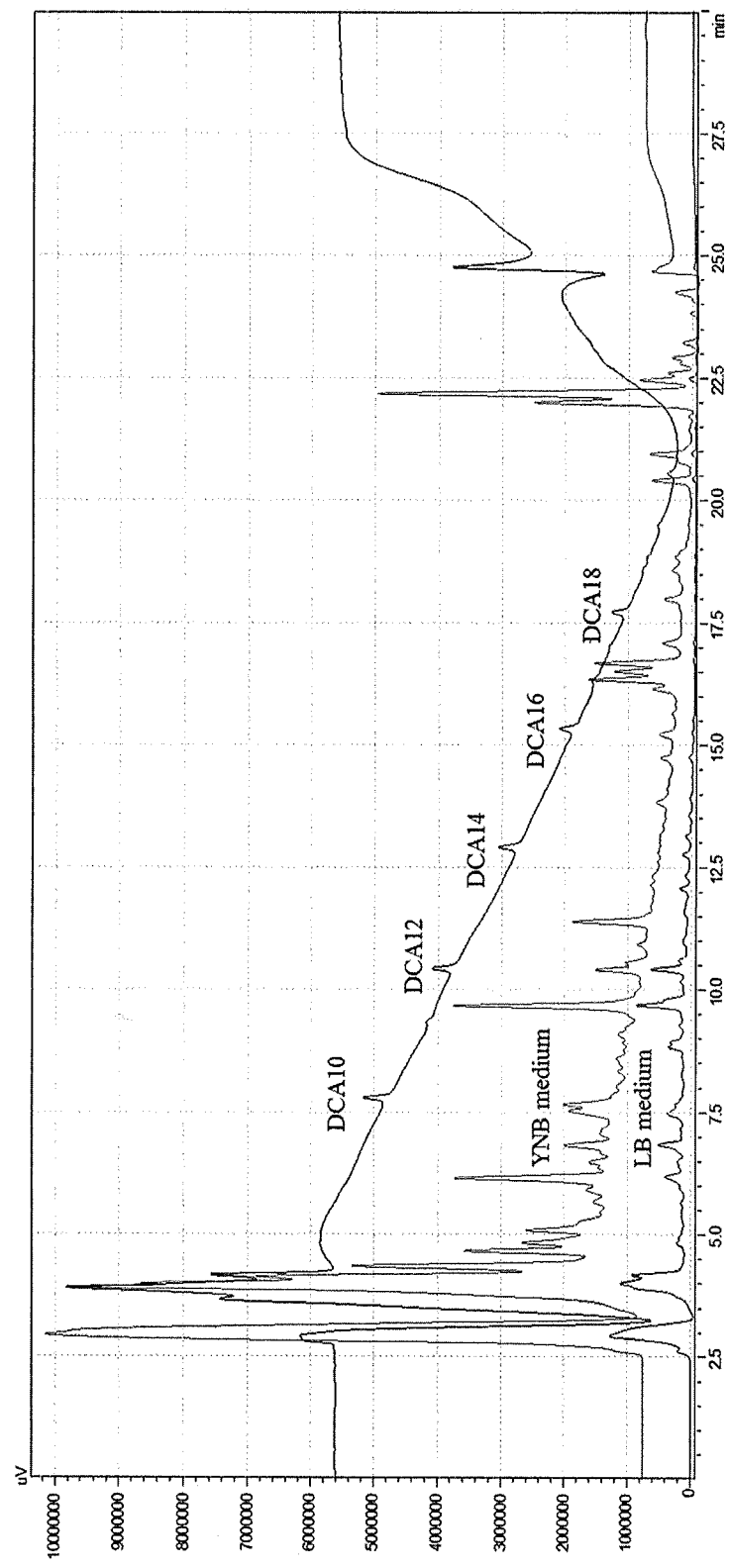
FIG. 10 is a graph showing HLPC analysis of dicarboxylic acid production of strain E1.

Strain E1 was cultured in YNB or LB medium in a fermentor under 1 vvm aeration and at 300 rpm. The pH was maintained at 6.0 for 1 day. Every 6 hours thereafter, additional 1% glucose was added to maintain the pH at 7.5 for two days. Dicarboxylic acid production was measured. See FIG. 10. As shown in FIG. 10, production reached 0.2 g.

Figure 11:
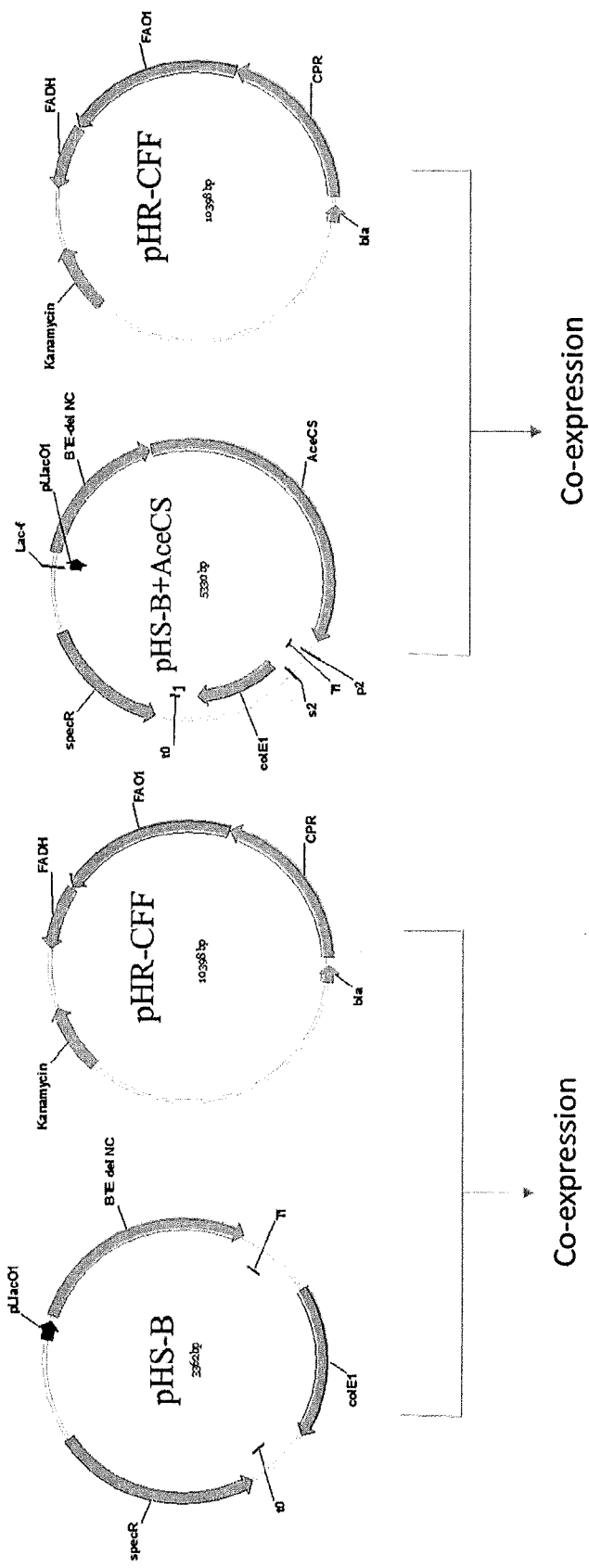
FIG. 11 is a schematic diagram showing expression constructs for generating modified *E. coli* strains E2 and E3.

We also constructed strains E2 (ΔfadD::BTEΔNC::CPR::FAO::FADH) and E3 (ΔfadD::BTEΔNC::AceCS::CPR::FAO::FADH). See FIG. 11. As shown in FIG. 11, construct pHS-B was generated by inserting the BTEΔNC gene into the pHS vector at the Acc65I/BamHI sites. Construct pHS-B+AceCS was generated by inserting the BTEΔNC and AceCS genes into the Acc65I/SalI and HindIII/BamHI sites of the pHS vector, respectively. pHS-B and pHR-CRR were introduced into host *E. coli* cells to generate strain E2 and pHS-B+AceCS and pHR-CFF were introduced into host *E. coli* cells to generate strain E3.

Figure 12:
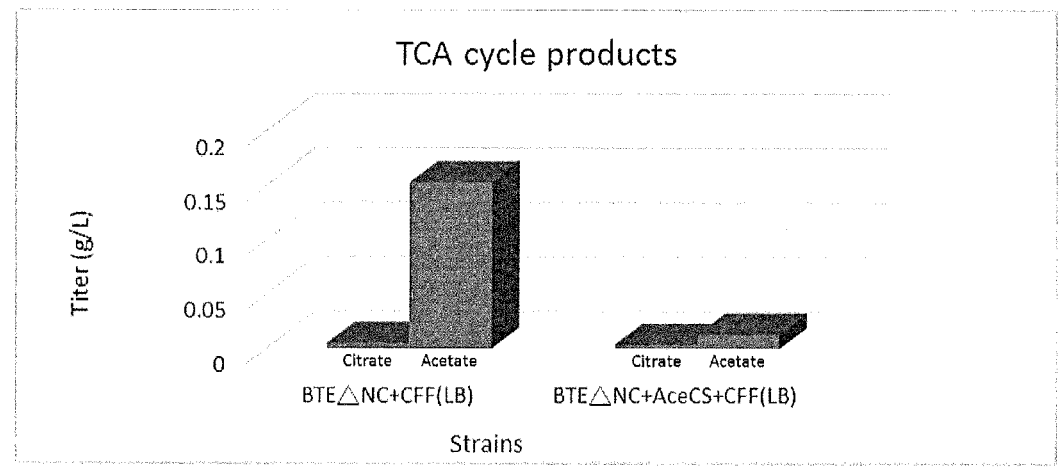
FIG. 12 is a bar graph showing citrate and acetate productions of strains E2 and E3.

Strains E2 and E3 were cultured in LB medium in a fermentor under 1 vvm aeration and at 300 rpm. The pH was maintained at 6.0 for 1 day. Every 6 hours thereafter, additional 1% glucose was added to maintain the pH at 7.5 for two days. Acetate production was measured. As shown in FIG. 12, strain E3 produced less acetate than strain E2.

Figure 13:
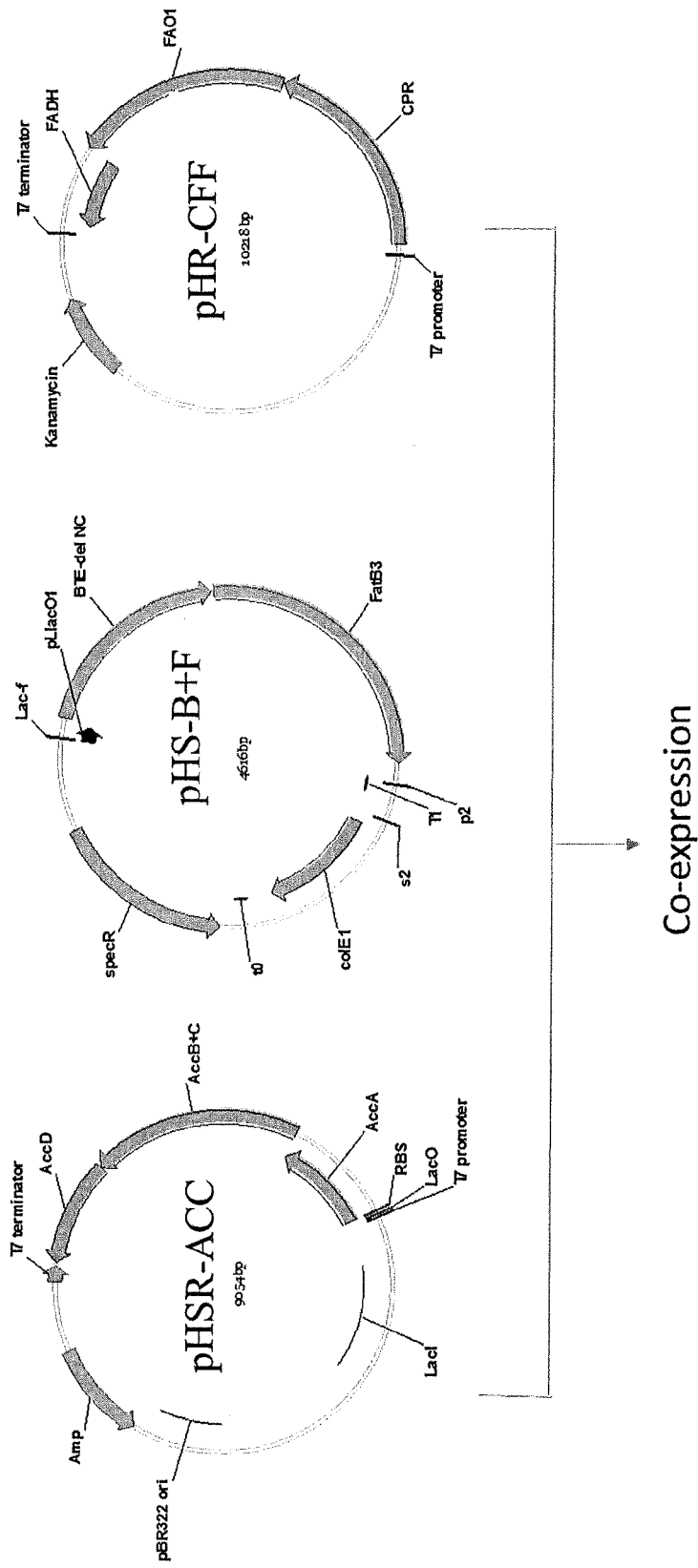
FIG. 13 is a schematic diagram showing expression constructs for generating modified *E. coli* strain E4.

Strain E4 (ΔfadD::ACC::BTEΔNC::FatB3::CPR::FAO::FADH) was constructed. See FIG. 13. Construct pHSR-ACC was generated by inserting the AccA, AccBC, and AccD genes into the NdeI/SpeI, SpeI/EagI, and EagI/XhoI sites of the pHSR vector, respectively. Constructs pHSR-ACC, pHS-B+F, and pHR-CFF were introduced into host *E. coli* cells to generate strain E4.

Figure 14:
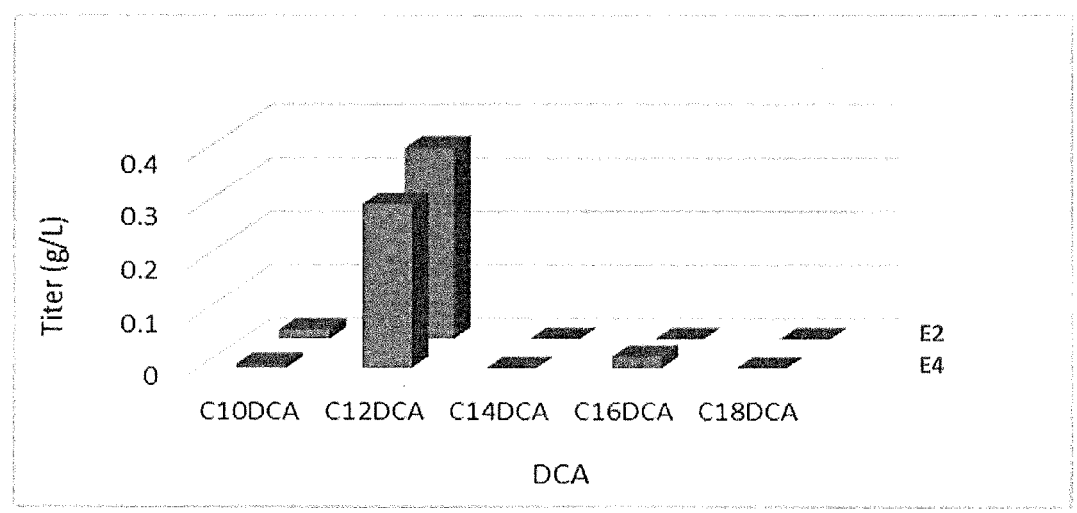
FIG. 14 is a bar graph showing dicarboxylic acid productions of strains E2 and E4.

Strain E2 and E4 were cultured in LB medium in a fermentor under 1 vvm aeration and at 300 rpm. The pH was maintained at 6.0 for 1 day. Every 6 hours thereafter, additional 1% glucose was added to maintain the pH at 7.5 for two days. Dicarboxylic acid production was measured. As shown in FIG. 14, C12DCA production reached 0.36 g/L.

Figure 15:
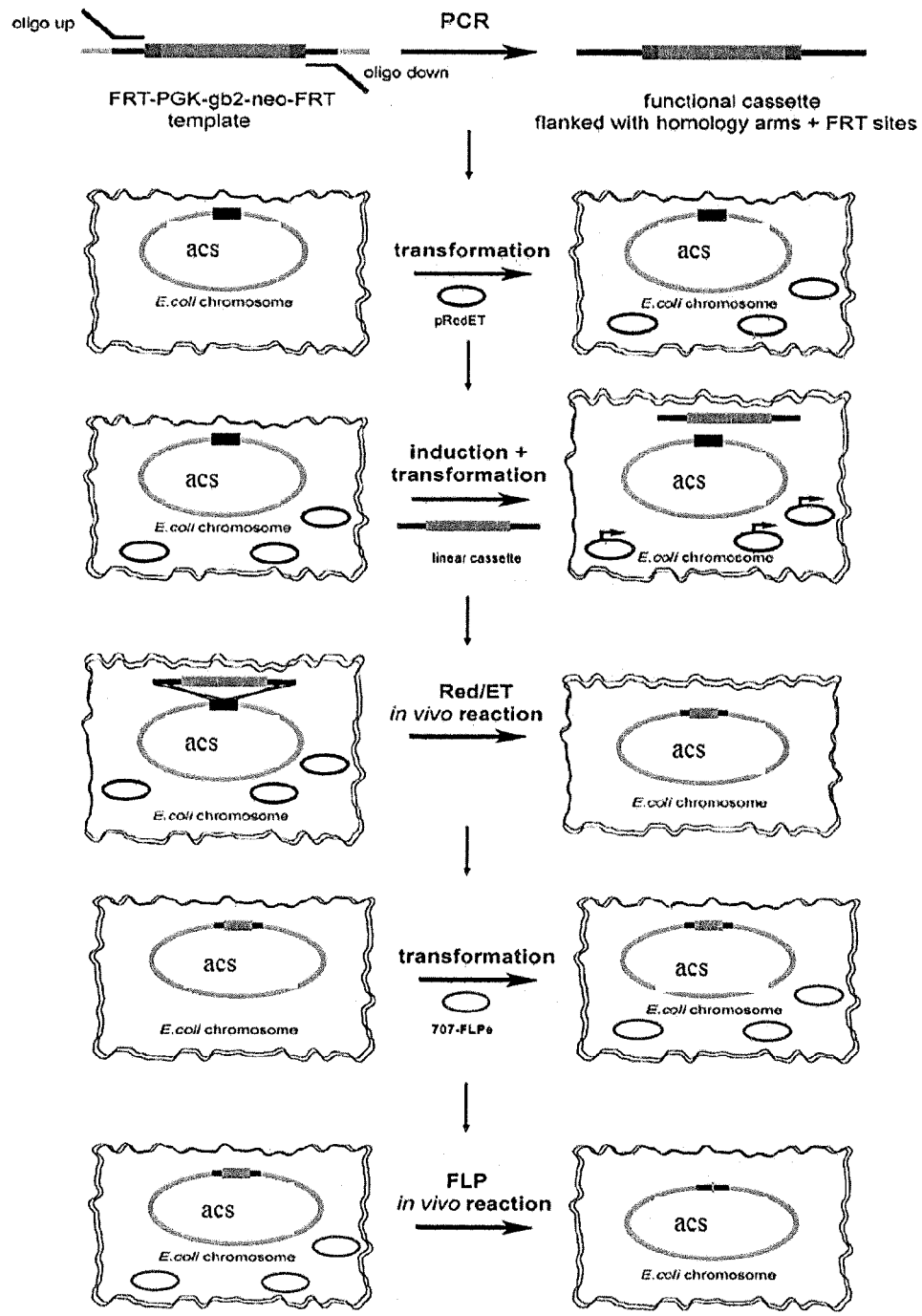
FIG. 15 is a schematic diagram showing construction of *E. coli* strain E5.

Strain E5 (ΔfadD::Δacs::CPR::FAO::FADH) was constructed. See FIG. 15. As shown in FIG. 15, a cassette (for knocking out the acs gene) including FRT sites flanked by homology arms were created using PCR using acs forward primer (SEQ ID NO:50) and reverse primer (SEQ ID NO:51). *E. coli* cells were transformed with pRedET followed by induction and transformation with the linear cassette. The linear cassette was then inserted into the target locus. Construct pHR-CFF was introduced into the Δacs strain.

Figure 16:
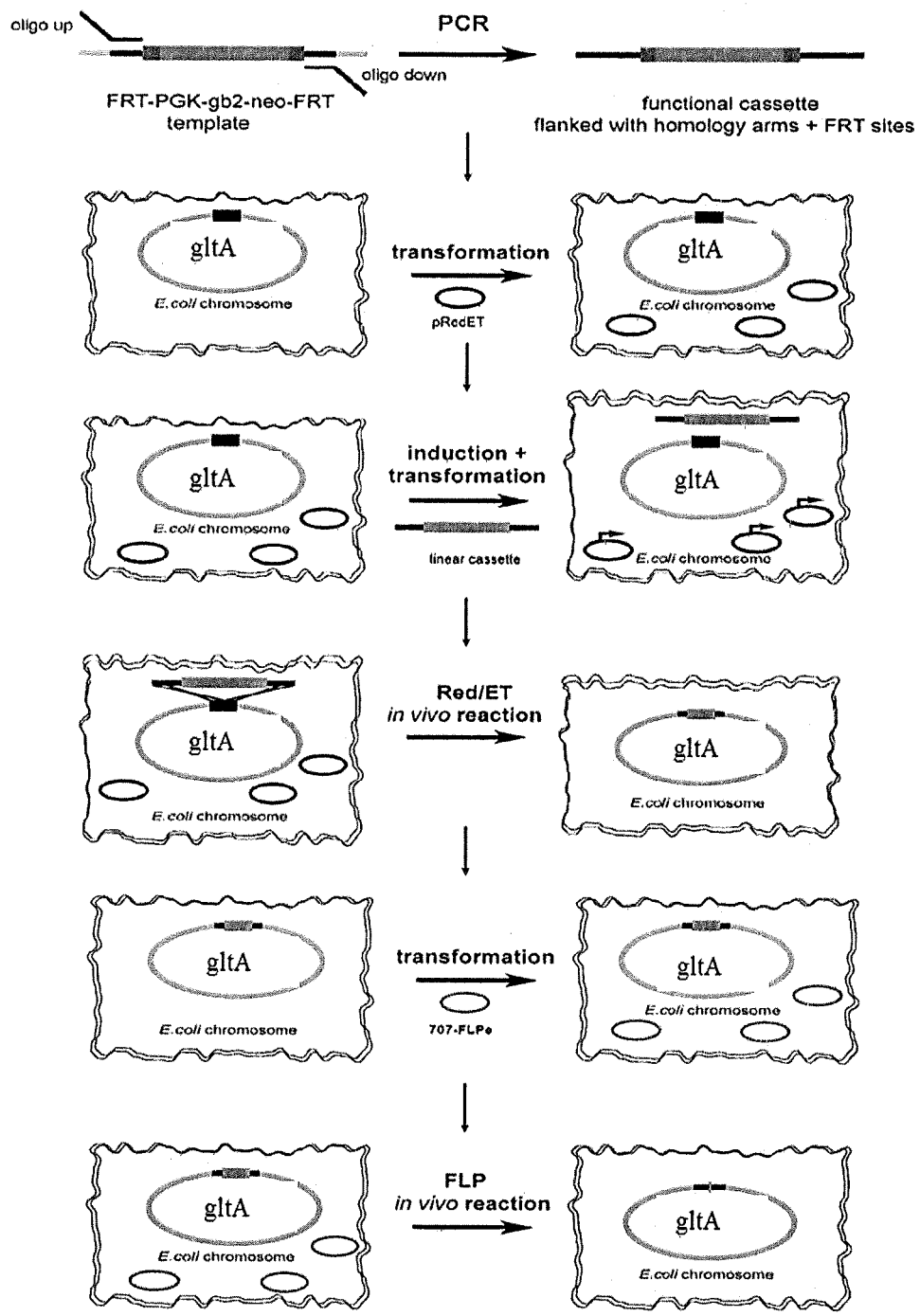
FIG. 16 is a schematic diagram showing construction of *E. coli* strain E6.

Strain E6 (ΔfadD::ΔgltA::CPR::FAO::FADH) was constructed using the same method. See FIG. 16. The functional cassette was generated using PCR using gltA forward primer (SEQ ID NO:52) and gltA reverse primer (SEQ ID NO:53). Construct pHR-CFF was introduced into the ΔgltA strain.

Figure 17:
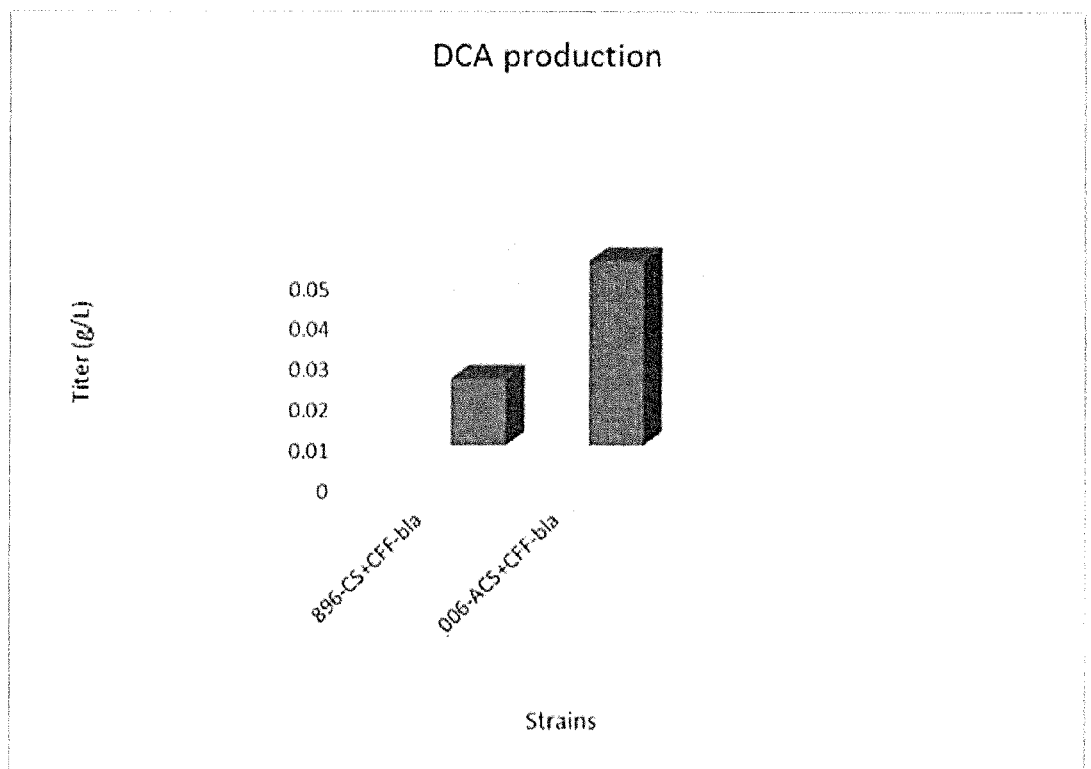
FIG. 17 is a bar graph showing dicarboxylic acid productions of strains E5 and E6.

Strains E5 and E6 were cultured in LB medium in a fermentor under 1 vvm aeration and at 300 rpm. The pH was maintained at 6.5 for 1 day. Every 6 hours thereafter, additional 1% glucose was added to maintain the pH at 7.5 for two days. Dicarboxylic acid production was measured. As shown in FIG. 17, C12DCA production reached 0.02 g/L and 0.05 g/L.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims. It will be apparent to those skilled in the art that various modifications and variations can be made to the disclosed embodiments. It is intended that the specification and examples be considered as exemplary only, with a true scope of the disclosure being indicated by the following claims and their equivalents

What is claimed is:

1. A genetically modified microorganism, comprising a first nucleic acid encoding an *Umbellularia californica* lauroyl acyl carrier protein (ACP) thioesterase (BTE) operably linked to a promoter, a second nucleic acid encoding a *Cocos nucifera* lauroyl ACP-thioesterase (FatB3) operably linked to a promoter, and one or more exogenous nucleic acids each operably linked to a promoter, each exogenous nucleic acid encoding a protein selected from the group consisting of an acetyl-CoA carboxylase (ACC), an acetyl-CoA carboxylase carboxyl transferase subunit a (AccA), an acetyl-CoA carboxylase biotin carboxyl carrier protein (AccB), an acetyl-CoA biotin carboxylase (AccC), an acetyl-CoA carboxylase transferase subunit β (AccD), a fatty acid synthase (FAS) subunit, a cytochrome P450 reductase (CPR), a long-chain alcohol oxidase (FAQ1), a long-chain alcohol dehydrogenase (FADH), and an adenosine monophosphate-forming acetyl-coenzyme A synthetase (AceCS), wherein the microorganism is *Escherichia coli* and produces an increased amount of long-chain dicarboxylic acids as compared to the unmodified parent of the microorganism, wherein the genetically modified microorganism further comprising a loss-of-function mutation in or expressing a lower level of one or more genes selected from the group consisting of a palmitoyl-acyl carrier protein (ACP) thioesterase gene, an acyl-coenzyme A oxidase gene, a citric synthetase (gltA) gene, or an acyl-coenzyme A synthetase (acs) gene.

2. A genetically modified microorganism comprising a first nucleic acid encoding an *Umbellularia californica* lauroyl ACP thioesterase (BTE) operably linked to a promoter, and a second nucleic acid encoding a *Cocos nucifera* lauroyl ACP thioesterase (FatB3) operably linked to a promoter, and further contains a loss-of-function mutation in or expresses a lower level of one or more genes selected from the group consisting of a palmitoyl-ACP thioesterase gene, an acyl-coenzyme A oxidase gene, a citric synthetase (gltA) gene, or an acyl-coenzyme A synthetase (acs) gene, wherein the microorganism is *Yarrowia lipolytica* and produces an increased amount of long-chain dicarboxylic acids as compared to the unmodified parent of the microorganism, wherein the microorganism (1) contains a loss-of-function mutation in or expresses a lower level of an acyl-coenzyme A oxidase gene and (2) further contains three exogenous nucleic acids each operably linked to a promoter and encoding a CPR, a FAO1, and a FADH, respectively.

3. The genetically modified microorganism of claim 2, wherein the microorganism contains a loss-of-function mutation in or expresses a lower level of an ACP thioesterase gene.

4. The genetically modified microorganism of claim 3, wherein the microorganism contains additional exogenous nucleic acids each operably linked to a promoter and encoding an AccD and a FAS subunit, respectively.

5. The genetically modified microorganism of claim 1, wherein the one or more exogenous nucleic acids include three nucleic acids each encoding a CPR, a FAO1, and a FADH, respectively.

6. The genetically modified microorganism of claim 5, wherein the one or more exogenous nucleic acids further include nucleic acids each encoding an AccA, an AccB, and an AccD.

7. The genetically modified microorganism of claim 5, further comprising a loss-of-function mutation in or expressing a lower level of an acs gene or a gltA gene.

8. The genetically modified microorganism of claim 5, wherein the BTE is BTEΔNC containing the sequence of SEQ ID NO:22 and the acyl-coenzyme A oxidase gene is fadD.

9. The genetically modified microorganism of claim 6, wherein the BTE is BTEΔNC containing the sequence of SEQ ID NO:22 and the acyl-coenzyme A oxidase gene is fadD.

10. The genetically modified organism of claim 2, wherein the acyl-coenzyme A oxidase gene is pox2 or pox5.

11. The genetically modified organism of claim 3, wherein the acyl-coenzyme A oxidase gene is pox2 or pox5.

12. The genetically modified organism of claim 4, wherein the acyl-coenzyme A oxidase gene is pox2 or pox5.

13. A method of producing a long-chain dicarboxylic acid, the method comprising:
providing the genetically-modified microorganism of claim 1; and
culturing the microorganism in a culture medium containing glucose or glycerol at pH 6 to 8 under conditions that allow production of a long-chain dicarboxylic acid; whereby the microorganism produces the long-chain dicarboxylic acid.

14. The method of claim 13, further comprising collecting the long-chain dicarboxylic acid.

15. The method of claim 14, wherein the long-chain dicarboxylic acid is C10-C18 dicarboxylic acid.

16. The method of claim 15, wherein the long-chain dicarboxylic acid is C12 dicarboxylic acid.

* * * * *

SEQUENCE LISTING

<160> NUMBER OF SEQ ID NOS: 53

<210> SEQ ID NO 1
<211> LENGTH: 6801
<212> TYPE: DNA
<213> ORGANISM: Yarrowia lipolytica
<220> FEATURE:
<221> NAME/KEY: misc_feature
<223> OTHER INFORMATION: biotin carboxylase

<400> SEQUENCE: 1

```
atgcgactgc aattgaggac actaacacgt cggtttttca gtatggcttc aggatcttca      60
acgccagatg tggctcccct tggtggacccc aacattcaca aaggtctcgc ctctcatttc     120
tttggactca attctgtcca cacagccaag ccctcaaaag tcaaggagtt tgtggcttct     180
cacggaggtc atacagttat caacaaggtc ctcatcgcta acaacggtat tgccgcagta     240
aaggagatcc gttcagtacg aaaatgggcc tacgagacct tggcgacga gcagcaatc      300
tcgttcaccg tcatggccac ccccgaagat ctcgctgcca cgccgacta cattagaatg     360
gccgatcagt acgtcgaggt gcccggagga accaacaaca acaactacgc caacgtcgag     420
ctgattgtcg acgtggctga gcgattcggc gtcgatgccg tgtgggccgg atggggccat     480
gccagtgaaa atcccctgct ccccgagtcg ctagcggcct ctccccgcaa gattgtcttc     540
atcggccctc ccggagctgc catgagatct ctgggagaca aaatttcttc taccattgtg     600
gcccagcacg caaaggtccc gtgtatcccg tggtctggaa ccggagtgga cgaggttgtg     660
gttgacaaga gcaccaacct cgtgtccgtg tccgaggagg tgtacaccaa gggctgcacc     720
accggtccca gcagggtct ggagaaggct aagcagattg gattccccgt gatgatcaag     780
gcttccgagg gaggaggagg aaagggtatt cgaaaggttg agcgagagga ggacttcgag     840
gctgcttacc accaggtcga gggagagatc cccggctcgc ccatcttcat tatgcagctt     900
gcaggcaatg cccggcattt ggaggtgcag cttctggctg atcagtacgg caacaatatt     960
tcactgtttg tcgagattg ttcggttcag cgacggcatc aaaagattat tgaggaggct    1020
cctgtgactg tggctggcca gcagaccttc actgccatgg agaaggctgc cgtgcgactc    1080
ggtaagcttg tcggatatgt ctctgcaggt accgttgaat atctgtattc ccatgaggac    1140
gacaagttct acttcttgga gctgaatcct cgtcttcagg tcgaacatcc taccaccgag    1200
atggtcaccg tgtcaacct gcccgctgcc cagcttcaga tcgccatggg tatccccctc    1260
gatcgaatca aggacattcg tctctttttac ggtgttaacc ctcaccaccac cactccaatt    1320
gatttcgact tctcgggcga ggatgctgat aagacacagc gacgtcccgt cccccgaggt    1380
cacaccactg cttgccgaat cacatccgag gaccctggag agggtttcaa gccctccgga    1440
ggtactatgc acgagctcaa cttccgatcc tcgtccaacg tgtggggtta cttctccgtt    1500
ggtaaccagg gaggtatcca ttcgttctcg gattcgcagt ttggtcacat cttcgccttc    1560
ggtgagaacc gaagtgcgtc tcgaaagcac atggttgttg ctttgaagga actatctatt    1620
cgaggtgact tccgaaccac cgtcgagtac ctcatcaagc tgctggagac accggacttc    1680
gaggacaaca ccatcaccac cggctggctg gatgagctta tctccaacaa gctgactgcc    1740
gagcgacccg actcgttcct cgctgttgtt tgtggtgctg ctaccaaggc ccatcgagct    1800
tccgaggact ctattgccac ctacatggct tcgctagaga agggccaggt ccctgctcga    1860
gacattctca gacccttttt ccccgttgac ttcatctacg agggccagcg gtacaagttc    1920
accgccaccc ggtcgtctga ggactcttac acgctgttca tcaacggttc tcgatgcgac    1980
attggagtta gacctctttc tgacggtggt attctgtgtc ttgtaggtgg gagatcccac    2040
aatgtctact ggaaggagga ggttggagcc acgcgactgt ctgttgactc caagacctgc    2100
cttctcgagg tggagaacga ccccactcag cttcgatctc cctctcccgg taagctggtt    2160
aagttcctgg tcgagaacgg cgaccacgtg cgagccaacc agcccatatgc cgagattgag    2220
gtcatgaaga tgtacatgac tctcactgct caggaggacg gtattgtcca gctgatgaag    2280
```

|  |  |  |  |  |  |
|---|---|---|---|---|---|
| cagcccggtt | ccaccatcga | ggctggcgac | atcctcggta | tcttggccct | tgatgatcct | 2340 |
| tccaaggtca | agcatgccaa | gcccttfgag | ggccagcttc | ccgagcttgg | accccccact | 2400 |
| ctcagcggta | acaagcctca | tcagcgatac | gagcactgcc | agaacgtgct | ccataacatt | 2460 |
| ctgcttggtt | tcgataacca | ggtggtgatg | aagtccactc | ttcaggagat | ggttggtctg | 2520 |
| ctccgaaacc | ctgagcttcc | ttatctccag | tgggctcatc | aggtgtcttc | tctgcacacc | 2580 |
| cgaatgagcg | ccaagctgga | tgctactctt | gctggtctca | ttgacaaggc | caagcagcga | 2640 |
| ggtggcgagt | tcctgccaa | gcagcttctg | cgagcccttg | agaaggaggc | gagctctggc | 2700 |
| gaggtcgatg | cgctcttcca | gcaaactctt | gctcctctgt | tgaccttgc | tcgagagtac | 2760 |
| caggacggtc | ttgctatcca | cgagcttcag | gttgctgcag | gccttctgca | ggcctactac | 2820 |
| gactctgagg | cccggttctg | cggacccaac | gtacgtgacg | aggatgtcat | tctcaagctt | 2880 |
| cgagaggaga | accgagattc | tcttcgaaag | gttgtgatgg | cccagctgtc | tcattctcga | 2940 |
| gtcggagcca | agaacaacct | tgtgctggcc | cttctcgatg | aatacaaggt | ggccgaccag | 3000 |
| gctggcaccg | actctcctgc | ctccaacgtg | cacgttgcaa | agtacttgcg | acctgtgctg | 3060 |
| cgaaagattg | tggagctgga | atctcgagct | tctgccaagg | tatctctgaa | agcccgagag | 3120 |
| attctcatcc | agtgcgctct | gccctctcta | aaggagcgaa | ctgaccagct | tgagcacatt | 3180 |
| ctgcgatctt | ctgtcgtcga | gtctcgatac | ggagaggttg | gtctggagca | ccgaactccc | 3240 |
| cgagccgata | ttctcaagga | ggttgtcgac | tccaagtaca | ttgtctttga | tgtgcttgcc | 3300 |
| cagttctttg | cccacgatga | tccctggatc | gtccttgctg | ccctggagct | gtacatccga | 3360 |
| cgagcttgca | aggcctactc | catcctggac | atcaactacc | accaggactc | ggacctgcct | 3420 |
| cccgtcatct | cgtggcgatt | tagactgcct | accatgtcgt | ctgctttgta | caactcagta | 3480 |
| gtgtcttctg | gctccaaaac | ccccacttcc | ccctcggtgt | ctcgagctga | ttccgtctcc | 3540 |
| gactttcgt | acaccgttga | gcgagactct | gctcccgctc | gaaccggagc | gattgttgcc | 3600 |
| gtgcctcatc | tggatgatct | ggaggatgct | ctgactcgtg | ttctggagaa | cctgcccaaa | 3660 |
| cggggcgctg | gtcttgccat | ctctgttggt | gctagcaaca | agagtgccgc | tgcttctgct | 3720 |
| cgtgacgctg | ctgctgctgc | cgcttcatcc | gttgacactg | gcctgtccaa | catttgcaac | 3780 |
| gttatgattg | gtcgggttga | tgagtctgat | gacgacgaca | ctctgattgc | ccgaatctcc | 3840 |
| caggtcattg | aggactttaa | ggaggacttt | gaggcctgtt | ctctgcgacg | aatcaccttc | 3900 |
| tccttcggca | actcccgagg | tacttatccc | aagtatttca | cgttccgagg | ccccgcatac | 3960 |
| gaggaggacc | ccactatccg | acacattgag | cctgctctgg | ccttccagct | ggagctcgcc | 4020 |
| cgtctgtcca | acttcgacat | caagcctgtc | cacaccgaca | accgaaacat | ccacgtgtac | 4080 |
| gaggctactg | gcaagaacgc | tgcttccgac | aagcggttct | tcacccgagg | tatcgtacga | 4140 |
| cctggtcgtc | ttcgagagaa | catccccacc | tcggagtatc | tcatttccga | ggctgaccgg | 4200 |
| ctcatgagcg | atattttgga | cgctctagag | gtgattggaa | ccaccaactc | ggatctcaac | 4260 |
| cacattttca | tcaacttctc | agccgtcttt | gctctgaagc | ccgaggaggt | tgaagctgcc | 4320 |
| tttggcggtt | tcctggagcg | atttggccga | cgtctgtggc | gacttcgagt | caccggtgcc | 4380 |
| gagatccgaa | tgatggtatc | cgaccccgaa | actggctctg | cttccctct | gcgagcaatg | 4440 |
| atcaacaacg | tctctggtta | cgttgtgcag | tctgagctgt | acgctgaggc | caagaacgac | 4500 |
| aagggccagt | ggattttcaa | gtctctgggc | aagcccggct | ccatgcacat | gcggtctatc | 4560 |
| aacactccct | accccaccaa | ggagtggctg | cagcccaagc | ggtacaaggc | ccatctgatg | 4620 |
| ggtaccacct | actgctatga | cttccccgag | ctgttccgac | agtccattga | gtcggactgg | 4680 |

```
aagaagtatg acggcaaggc tcccgacgat ctcatgactt gcaacgagct gattctcgat    4740
gaggactctg gcgagctgca ggaggtgaac cgagagcccg gcgccaacaa cgtcggtatg    4800
gttgcgtgga agtttgaggc caagaccccc gagtaccctc gaggccgatc tttcatcgtg    4860
gtggccaacg atatcacctt ccagattggt tcgtttggcc ctgctgagga ccagttcttc    4920
ttcaaggtga cggagctggc tcgaaagctc ggtattcctc gaatctatct gtctgccaac    4980
tctggtgctc gaatcggcat tgctgacgag ctcgttggca agtacaaggt tgcgtggaac    5040
gacgagactg accccctccaa gggcttcaag tacctttact caccccctga gtctcttgcc    5100
accctcaagc ccgacactgt tgtcaccact gagattgagg aggagggtcc caacggcgtg    5160
gagaagcgtc atgtgatcga ctacattgtc ggagagaagg acggtctcgg agtcgagtgt    5220
ctgcggggct ctggtctcat tgcaggcgcc acttctcgag cctacaagga tatcttcact    5280
ctcactcttg tcacctgtcg atccgttggt atcggtgctt accttgttcg tcttggtcaa    5340
cgagccatcc agattgaggg ccagcccatc attctcactg gtgccccgc catcaacaag    5400 ctgcttggtc gagaggtcta ctcttccaac ttgcagcttg gtggtactca gatcatgtac    5460
aacaacggtg tgtctcatct gactgcccga gatgatctca acggtgtcca caagatcatg    5520
cagtggctgt catacatccc tgcttctcga ggtcttccag tgcctgttct ccctcacaag    5580
accgatgtgt gggatcgaga cgtgacgttc cagcctgtcc gaggcgagca gtacgatgtt    5640
agatggctta tttctggccg aactctcgag gatggtgctt tcgagtctgg tctctttgac    5700
aaggactctt tccaggagac tctgtctggc tgggccaagg tgttgttgt tggtcgagct    5760 cgtcttggcg gcattcccttc cggtgtcatt ggtgtcgaga ctgcgaccgt cgacaatact    5820 accccctgccg atcccgccaa cccggactct attgagatga gcacctctga agccggccag    5880
gtttggtacc ccaactcggc cttcaagacc tctcaggcca tcaacgactt caaccatggt    5940
gaggcgcttc ctctcatgat tcttgctaac tggcgaggct tttctggtgg tcagcgagac    6000
atgtacaatg aggttctcaa gtacggatct ttcattgttg atgctctggt tgactacaag    6060
cagcccatca tggtgtacat ccctcccacc ggtgagctgc gaggtggttc ttgggttgtg    6120
gttgacccca ccatcaactc ggacatgatg gagatgtacg ctgacgtcga gtctcgaggt    6180
ggtgtgctgg agcccgaggg aatggtcggt atcaagtacc gacgagacaa gctactggac    6240
accatggctc gtctggatcc cgagtactcc tctctcaaga gcagcttga ggagtctccc    6300 gattctgagg agctcaaggt caagctcagc gtgcgagaga gtctctcat gcccatctac    6360 cagcagatct ccgtgcagtt tgccgacttg catgaccgag ctggccgaat ggaggccaag    6420
ggtgtcattc gtgaggctct tgtgtggaag gatgctcgtc gattcttctt ctggcgaatc    6480
cgacgacgat tagtcgagga gtacctcatt accaagatca atagcattct gccctcttgc    6540
actcggcttg agtgtctggc tcgaatcaag tcgtggaagc ctgccactct tgatcagggc    6600
tctgaccggg gtgttgccga gtggtttgac gagaactctg atgccgtctc tgctcgactc    6660
agcgagctca agaaggacgc ttctgcccag tcgtttgctt ctcaactgag aaaggaccga    6720
cagggtactc tccagggcat gaagcaggct ctcgcttctc tttctgaggc tgagcgggct    6780
gagctgctca agggggttgtg a                                              6801
```

<210> SEQ ID NO 2  
<211> LENGTH: 2266  
<212> TYPE: PRT  
<213> ORGANISM: Yarrowia lipolytica  
<220> FEATURE:

<221> NAME/KEY: MISC_FEATURE
<223> OTHER INFORMATION: biotin carboxylase

<400> SEQUENCE: 2

```
Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
            20                  25                  30

His Lys Gly Leu Ala Ser His Phe Phe Gly Leu Asn Ser Val His Thr
        35                  40                  45

Ala Lys Pro Ser Lys Val Lys Glu Phe Val Ala Ser His Gly Gly His
    50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110

Ala Asn Ala Asp Tyr Ile Arg Met Ala Asp Gln Tyr Val Glu Val Pro
        115                 120                 125

Gly Gly Thr Asn Asn Asn Tyr Ala Asn Val Glu Leu Ile Val Asp
    130                 135                 140

Val Ala Glu Arg Phe Gly Val Asp Ala Val Trp Ala Gly Trp Gly His
145                 150                 155                 160

Ala Ser Glu Asn Pro Leu Leu Pro Glu Ser Leu Ala Ala Ser Pro Arg
                165                 170                 175

Lys Ile Val Phe Ile Gly Pro Pro Gly Ala Ala Met Arg Ser Leu Gly
            180                 185                 190

Asp Lys Ile Ser Ser Thr Ile Val Ala Gln His Ala Lys Val Pro Cys
        195                 200                 205

Ile Pro Trp Ser Gly Thr Gly Val Asp Glu Val Val Val Asp Lys Ser
    210                 215                 220

Thr Asn Leu Val Ser Val Ser Glu Glu Val Tyr Thr Lys Gly Cys Thr
225                 230                 235                 240

Thr Gly Pro Lys Gln Gly Leu Glu Lys Ala Lys Gln Ile Gly Phe Pro
                245                 250                 255

Val Met Ile Lys Ala Ser Glu Gly Gly Gly Gly Lys Gly Ile Arg Lys
            260                 265                 270

Val Glu Arg Glu Glu Asp Phe Glu Ala Ala Tyr His Gln Val Glu Gly
        275                 280                 285

Glu Ile Pro Gly Ser Pro Ile Phe Ile Met Gln Leu Ala Gly Asn Ala
    290                 295                 300

Arg His Leu Glu Val Gln Leu Leu Ala Asp Gln Tyr Gly Asn Asn Ile
305                 310                 315                 320

Ser Leu Phe Gly Arg Asp Cys Ser Val Gln Arg Arg His Gln Lys Ile
                325                 330                 335

Ile Glu Glu Ala Pro Val Thr Val Ala Gly Gln Gln Thr Phe Thr Ala
            340                 345                 350

Met Glu Lys Ala Ala Val Arg Leu Gly Lys Leu Val Gly Tyr Val Ser
        355                 360                 365

Ala Gly Thr Val Glu Tyr Leu Tyr Ser His Glu Asp Asp Lys Phe Tyr
    370                 375                 380

Phe Leu Glu Leu Asn Pro Arg Leu Gln Val Glu His Pro Thr Thr Glu
385                 390                 395                 400
```

```
Met Val Thr Gly Val Asn Leu Pro Ala Ala Gln Leu Gln Ile Ala Met
            405                 410                 415

Gly Ile Pro Leu Asp Arg Ile Lys Asp Ile Arg Leu Phe Tyr Gly Val
            420                 425                 430

Asn Pro His Thr Thr Pro Ile Asp Phe Asp Phe Ser Gly Glu Asp
            435                 440             445

Ala Asp Lys Thr Gln Arg Arg Pro Val Pro Arg Gly His Thr Thr Ala
450                 455                 460

Cys Arg Ile Thr Ser Glu Asp Pro Gly Glu Gly Phe Lys Pro Ser Gly
465                 470                 475                 480

Gly Thr Met His Glu Leu Asn Phe Arg Ser Ser Asn Val Trp Gly
            485                 490                 495

Tyr Phe Ser Val Gly Asn Gln Gly Gly Ile His Ser Phe Ser Asp Ser
                500                 505                 510

Gln Phe Gly His Ile Phe Ala Phe Gly Glu Asn Arg Ser Ala Ser Arg
            515                 520                 525

Lys His Met Val Val Ala Leu Lys Glu Leu Ser Ile Arg Gly Asp Phe
    530                 535                 540

Arg Thr Thr Val Glu Tyr Leu Ile Lys Leu Leu Glu Thr Pro Asp Phe
545                 550                 555                 560

Glu Asp Asn Thr Ile Thr Thr Gly Trp Leu Asp Glu Leu Ile Ser Asn
                565                 570                 575

Lys Leu Thr Ala Glu Arg Pro Asp Ser Phe Leu Ala Val Val Cys Gly
            580                 585                 590

Ala Ala Thr Lys Ala His Arg Ala Ser Glu Asp Ser Ile Ala Thr Tyr
            595                 600                 605

Met Ala Ser Leu Glu Lys Gly Gln Val Pro Ala Arg Asp Ile Leu Lys
    610                 615                 620

Thr Leu Phe Pro Val Asp Phe Ile Tyr Glu Gly Gln Arg Tyr Lys Phe
625                 630                 635                 640

Thr Ala Thr Arg Ser Ser Glu Asp Ser Tyr Thr Leu Phe Ile Asn Gly
                645                 650                 655

Ser Arg Cys Asp Ile Gly Val Arg Pro Leu Ser Asp Gly Gly Ile Leu
            660                 665                 670

Cys Leu Val Gly Gly Arg Ser His Asn Val Tyr Trp Lys Glu Glu Val
    675                 680                 685

Gly Ala Thr Arg Leu Ser Val Asp Ser Lys Thr Cys Leu Leu Glu Val
    690                 695                 700

Glu Asn Asp Pro Thr Gln Leu Arg Ser Pro Ser Pro Gly Lys Leu Val
705                 710                 715                 720

Lys Phe Leu Val Glu Asn Gly Asp His Val Arg Ala Asn Gln Pro Tyr
                725                 730                 735

Ala Glu Ile Glu Val Met Lys Met Tyr Met Thr Leu Thr Ala Gln Glu
            740                 745                 750

Asp Gly Ile Val Gln Leu Met Lys Gln Pro Gly Ser Thr Ile Glu Ala
            755                 760                 765

Gly Asp Ile Leu Gly Ile Leu Ala Leu Asp Asp Pro Ser Lys Val Lys
770                 775                 780

His Ala Lys Pro Phe Glu Gly Gln Leu Pro Glu Leu Gly Pro Pro Thr
785                 790                 795                 800

Leu Ser Gly Asn Lys Pro His Gln Arg Tyr Glu His Cys Gln Asn Val
                805                 810                 815
```

-continued

Leu His Asn Ile Leu Leu Gly Phe Asp Asn Gln Val Val Met Lys Ser
            820                 825                 830

Thr Leu Gln Glu Met Val Gly Leu Leu Arg Asn Pro Glu Leu Pro Tyr
        835                 840                 845

Leu Gln Trp Ala His Gln Val Ser Ser Leu His Thr Arg Met Ser Ala
    850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Leu Arg Ala Leu Glu Lys Glu
                885                 890                 895

Ala Ser Ser Gly Glu Val Asp Ala Leu Phe Gln Gln Thr Leu Ala Pro
            900                 905                 910

Leu Phe Asp Leu Ala Arg Glu Tyr Gln Asp Gly Leu Ala Ile His Glu
        915                 920                 925

Leu Gln Val Ala Ala Gly Leu Leu Gln Ala Tyr Tyr Asp Ser Glu Ala
    930                 935                 940

Arg Phe Cys Gly Pro Asn Val Arg Asp Glu Asp Val Ile Leu Lys Leu
945                 950                 955                 960

Arg Glu Glu Asn Arg Asp Ser Leu Arg Lys Val Val Met Ala Gln Leu
                965                 970                 975

Ser His Ser Arg Val Gly Ala Lys Asn Asn Leu Val Leu Ala Leu Leu
            980                 985                 990

Asp Glu Tyr Lys Val Ala Asp Gln Ala Gly Thr Asp Ser Pro Ala Ser
        995                 1000                1005

Asn Val His Val Ala Lys Tyr Leu Arg Pro Val Leu Arg Lys Ile
    1010                1015                1020

Val Glu Leu Glu Ser Arg Ala Ser Ala Lys Val Ser Leu Lys Ala
    1025                1030                1035

Arg Glu Ile Leu Ile Gln Cys Ala Leu Pro Ser Leu Lys Glu Arg
    1040                1045                1050

Thr Asp Gln Leu Glu His Ile Leu Arg Ser Ser Val Val Glu Ser
    1055                1060                1065

Arg Tyr Gly Glu Val Gly Leu Glu His Arg Thr Pro Arg Ala Asp
    1070                1075                1080

Ile Leu Lys Glu Val Val Asp Ser Lys Tyr Ile Val Phe Asp Val
    1085                1090                1095

Leu Ala Gln Phe Phe Ala His Asp Asp Pro Trp Ile Val Leu Ala
    1100                1105                1110

Ala Leu Glu Leu Tyr Ile Arg Arg Ala Cys Lys Ala Tyr Ser Ile
    1115                1120                1125

Leu Asp Ile Asn Tyr His Gln Asp Ser Asp Leu Pro Pro Val Ile
    1130                1135                1140

Ser Trp Arg Phe Arg Leu Pro Thr Met Ser Ser Ala Leu Tyr Asn
    1145                1150                1155

Ser Val Val Ser Ser Gly Ser Lys Thr Pro Thr Ser Pro Ser Val
    1160                1165                1170

Ser Arg Ala Asp Ser Val Ser Asp Phe Ser Tyr Thr Val Glu Arg
    1175                1180                1185

Asp Ser Ala Pro Ala Arg Thr Gly Ala Ile Val Ala Val Pro His
    1190                1195                1200

Leu Asp Asp Leu Glu Asp Ala Leu Thr Arg Val Leu Glu Asn Leu
    1205                1210                1215

Pro Lys Arg Gly Ala Gly Leu Ala Ile Ser Val Gly Ala Ser Asn

-continued

|      | 1220 |      |      | 1225 |      |      |      | 1230 |      |      |
|------|------|------|------|------|------|------|------|------|------|------|
| Lys  | Ser  | Ala  | Ala  | Ala  | Ser  | Ala  | Arg  | Asp  | Ala  | Ala  | Ala Ala Ala
|      | 1235 |      |      |      | 1240 |      |      |      | 1245 |      |

Ser Ser Val Asp Thr Gly Leu Ser Asn Ile Cys Asn Val Met Ile
    1250                    1255                  1260

Gly Arg Val Asp Glu Ser Asp Asp Asp Thr Leu Ile Ala Arg
    1265                    1270                 1275

Ile Ser Gln Val Ile Glu Asp Phe Lys Glu Asp Phe Glu Ala Cys
    1280                    1285                 1290

Ser Leu Arg Arg Ile Thr Phe Ser Phe Gly Asn Ser Arg Gly Thr
    1295                    1300                 1305

Tyr Pro Lys Tyr Phe Thr Phe Arg Gly Pro Ala Tyr Glu Glu Asp
    1310                    1315                 1320

Pro Thr Ile Arg His Ile Glu Pro Ala Leu Ala Phe Gln Leu Glu
    1325                    1330                 1335

Leu Ala Arg Leu Ser Asn Phe Asp Ile Lys Pro Val His Thr Asp
    1340                    1345                 1350

Asn Arg Asn Ile His Val Tyr Glu Ala Thr Gly Lys Asn Ala Ala
    1355                    1360                 1365

Ser Asp Lys Arg Phe Phe Thr Arg Gly Ile Val Arg Pro Gly Arg
    1370                    1375                 1380

Leu Arg Glu Asn Ile Pro Thr Ser Glu Tyr Leu Ile Ser Glu Ala
    1385                    1390                 1395

Asp Arg Leu Met Ser Asp Ile Leu Asp Ala Leu Glu Val Ile Gly
    1400                    1405                 1410

Thr Thr Asn Ser Asp Leu Asn His Ile Phe Ile Asn Phe Ser Ala
    1415                    1420                 1425

Val Phe Ala Leu Lys Pro Glu Glu Val Glu Ala Ala Phe Gly Gly
    1430                    1435                 1440

Phe Leu Glu Arg Phe Gly Arg Arg Leu Trp Arg Leu Arg Val Thr
    1445                    1450                 1455

Gly Ala Glu Ile Arg Met Met Val Ser Asp Pro Glu Thr Gly Ser
    1460                    1465                 1470

Ala Phe Pro Leu Arg Ala Met Ile Asn Asn Val Ser Gly Tyr Val
    1475                    1480                 1485

Val Gln Ser Glu Leu Tyr Ala Glu Ala Lys Asn Asp Lys Gly Gln
    1490                    1495                 1500

Trp Ile Phe Lys Ser Leu Gly Lys Pro Gly Ser Met His Met Arg
    1505                    1510                 1515

Ser Ile Asn Thr Pro Tyr Pro Thr Lys Glu Trp Leu Gln Pro Lys
    1520                    1525                 1530

Arg Tyr Lys Ala His Leu Met Gly Thr Thr Tyr Cys Tyr Asp Phe
    1535                    1540                 1545

Pro Glu Leu Phe Arg Gln Ser Ile Glu Ser Asp Trp Lys Lys Tyr
    1550                    1555                 1560

Asp Gly Lys Ala Pro Asp Asp Leu Met Thr Cys Asn Glu Leu Ile
    1565                    1570                 1575

Leu Asp Glu Asp Ser Gly Glu Leu Gln Glu Val Asn Arg Glu Pro
    1580                    1585                 1590

Gly Ala Asn Asn Val Gly Met Val Ala Trp Lys Phe Glu Ala Lys
    1595                    1600                 1605

Thr Pro Glu Tyr Pro Arg Gly Arg Ser Phe Ile Val Val Ala Asn
    1610                    1615                 1620

```
Asp Ile Thr Phe Gln Ile Gly Ser Phe Gly Pro Ala Glu Asp Gln
1625                1630                1635

Phe Phe Phe Lys Val Thr Glu Leu Ala Arg Lys Leu Gly Ile Pro
1640                1645                1650

Arg Ile Tyr Leu Ser Ala Asn Ser Gly Ala Arg Ile Gly Ile Ala
1655                1660                1665

Asp Glu Leu Val Gly Lys Tyr Lys Val Ala Trp Asn Asp Glu Thr
1670                1675                1680

Asp Pro Ser Lys Gly Phe Lys Tyr Leu Tyr Phe Thr Pro Glu Ser
1685                1690                1695

Leu Ala Thr Leu Lys Pro Asp Thr Val Val Thr Thr Glu Ile Glu
1700                1705                1710

Glu Glu Gly Pro Asn Gly Val Glu Lys Arg His Val Ile Asp Tyr
1715                1720                1725

Ile Val Gly Glu Lys Asp Gly Leu Gly Val Glu Cys Leu Arg Gly
1730                1735                1740

Ser Gly Leu Ile Ala Gly Ala Thr Ser Arg Ala Tyr Lys Asp Ile
1745                1750                1755

Phe Thr Leu Thr Leu Val Thr Cys Arg Ser Val Gly Ile Gly Ala
1760                1765                1770

Tyr Leu Val Arg Leu Gly Gln Arg Ala Ile Gln Ile Glu Gly Gln
1775                1780                1785

Pro Ile Ile Leu Thr Gly Ala Pro Ala Ile Asn Lys Leu Leu Gly
1790                1795                1800

Arg Glu Val Tyr Ser Ser Asn Leu Gln Leu Gly Gly Thr Gln Ile
1805                1810                1815

Met Tyr Asn Asn Gly Val Ser His Leu Thr Ala Arg Asp Asp Leu
1820                1825                1830

Asn Gly Val His Lys Ile Met Gln Trp Leu Ser Tyr Ile Pro Ala
1835                1840                1845

Ser Arg Gly Leu Pro Val Pro Val Leu Pro His Lys Thr Asp Val
1850                1855                1860

Trp Asp Arg Asp Val Thr Phe Gln Pro Val Arg Gly Glu Gln Tyr
1865                1870                1875

Asp Val Arg Trp Leu Ile Ser Gly Arg Thr Leu Glu Asp Gly Ala
1880                1885                1890

Phe Glu Ser Gly Leu Phe Asp Lys Asp Ser Phe Gln Glu Thr Leu
1895                1900                1905

Ser Gly Trp Ala Lys Gly Val Val Gly Arg Ala Arg Leu Gly
1910                1915                1920

Gly Ile Pro Phe Gly Val Ile Gly Val Glu Thr Ala Thr Val Asp
1925                1930                1935

Asn Thr Thr Pro Ala Asp Pro Ala Asn Pro Asp Ser Ile Glu Met
1940                1945                1950

Ser Thr Ser Glu Ala Gly Gln Val Trp Tyr Pro Asn Ser Ala Phe
1955                1960                1965

Lys Thr Ser Gln Ala Ile Asn Asp Phe Asn His Gly Glu Ala Leu
1970                1975                1980

Pro Leu Met Ile Leu Ala Asn Trp Arg Gly Phe Ser Gly Gly Gln
1985                1990                1995

Arg Asp Met Tyr Asn Glu Val Leu Lys Tyr Gly Ser Phe Ile Val
2000                2005                2010
```

| | | | | | | | | | | |
|---|---|---|---|---|---|---|---|---|---|---|
| Asp | Ala | Leu | Val | Asp | Tyr | Lys | Gln | Pro | Ile | Met | Val | Tyr | Ile | Pro |
| | 2015 | | | | 2020 | | | | 2025 | |

Pro Thr Gly Glu Leu Arg Gly Gly Ser Trp Val Val Asp Pro
    2030              2035              2040

Thr Ile Asn Ser Asp Met Met Glu Met Tyr Ala Asp Val Glu Ser
    2045              2050              2055

Arg Gly Gly Val Leu Glu Pro Glu Gly Met Val Gly Ile Lys Tyr
    2060              2065              2070

Arg Arg Asp Lys Leu Leu Asp Thr Met Ala Arg Leu Asp Pro Glu
    2075              2080              2085

Tyr Ser Ser Leu Lys Lys Gln Leu Glu Glu Ser Pro Asp Ser Glu
    2090              2095              2100

Glu Leu Lys Val Lys Leu Ser Val Arg Glu Lys Ser Leu Met Pro
    2105              2110              2115

Ile Tyr Gln Gln Ile Ser Val Gln Phe Ala Asp Leu His Asp Arg
    2120              2125              2130

Ala Gly Arg Met Glu Ala Lys Gly Val Ile Arg Glu Ala Leu Val
    2135              2140              2145

Trp Lys Asp Ala Arg Arg Phe Phe Phe Trp Arg Ile Arg Arg Arg
    2150              2155              2160

Leu Val Glu Glu Tyr Leu Ile Thr Lys Ile Asn Ser Ile Leu Pro
    2165              2170              2175

Ser Cys Thr Arg Leu Glu Cys Leu Ala Arg Ile Lys Ser Trp Lys
    2180              2185              2190

Pro Ala Thr Leu Asp Gln Gly Ser Asp Arg Gly Val Ala Glu Trp
    2195              2200              2205

Phe Asp Glu Asn Ser Asp Ala Val Ser Ala Arg Leu Ser Glu Leu
    2210              2215              2220

Lys Lys Asp Ala Ser Ala Gln Ser Phe Ala Ser Gln Leu Arg Lys
    2225              2230              2235

Asp Arg Gln Gly Thr Leu Gln Gly Met Lys Gln Ala Leu Ala Ser
    2240              2245              2250

Leu Ser Glu Ala Glu Arg Ala Glu Leu Leu Lys Gly Leu
    2255              2260              2265

<210> SEQ ID NO 3
<211> LENGTH: 960
<212> TYPE: DNA
<213> ORGANISM: Escherichia coli
<220> FEATURE:
<221> NAME/KEY: misc_feature
<223> OTHER INFORMATION: Acetyl-CoA carboxylase carboxyl transferase
      subunit alpha

<400> SEQUENCE: 3
atgagtctga atttccttga ttttgaacag ccgattgcag agctggaagc gaaaatcgat      60
tctctgactg cggttagccg tcaggatgag aaactggata ttaacatcga tgaagaagtg     120
catcgtctgc gtgaaaaaag cgtagaactg acacgtaaaa tcttcgccga tctcggtgca     180
tggcagattg cgcaactggc acgccatcca cagcgtcctt ataccctgga ttacgttcgc     240
ctggcatttg atgaatttga cgaactggct ggcgaccgcg cgtatgcaga cgataaagct     300
atcgtcggtg gtatcgcccg tctcgatggt cgtccggtga tgatcattgg tcatcaaaaa     360
ggtcgtgaaa ccaaagaaaa aattcgccgt aactttggta tgccagcgcc agaaggttac     420
cgcaaagcac tgcgtctgat gcaaatggct gaacgcttta gatgcctat catcaccttt     480

```
atcgacaccc cggggggctta tcctggcgtg ggcgcagaag agcgtggtca gtctgaagcc    540
attgcacgca acctgcgtga aatgtctcgc ctcggcgtac cggtagtttg tacggttatc    600
ggtgaaggtg gttctggcgg tgcgctggcg attggcgtgg gcgataaagt gaatatgctg    660
caatacagca cctattccgt tatctcgccg gaaggttgtg cgtccattct gtggaagagc    720
gccgacaaag cgccgctggc ggctgaagcg atgggtatca ttgctccgcg tctgaaagaa    780
ctgaaactga tcgactccat catcccggaa ccactgggtg gtgctcaccg taacccggaa    840
gcgatggcgg catcgttgaa agcgcaactg ctggcggatc tggccgatct cgacgtgtta    900
agcactgaag atttaaaaaa tcgtcgttat cagcgcctga tgagctacgg ttacgcgtaa    960
```

<210> SEQ ID NO 4
<211> LENGTH: 319
<212> TYPE: PRT
<213> ORGANISM: Escherichia coli
<220> FEATURE:
<221> NAME/KEY: MISC_FEATURE
<223> OTHER INFORMATION: Acetyl-CoA carboxylase carboxyl transferase subunit alpha

<400> SEQUENCE: 4

```
Met Ser Leu Asn Phe Leu Asp Phe Glu Gln Pro Ile Ala Glu Leu Glu
1               5                   10                  15

Ala Lys Ile Asp Ser Leu Thr Ala Val Ser Arg Gln Asp Glu Lys Leu
            20                  25                  30

Asp Ile Asn Ile Asp Glu Glu Val His Arg Leu Arg Glu Lys Ser Val
        35                  40                  45

Glu Leu Thr Arg Lys Ile Phe Ala Asp Leu Gly Ala Trp Gln Ile Ala
    50                  55                  60

Gln Leu Ala Arg His Pro Gln Arg Pro Tyr Thr Leu Asp Tyr Val Arg
65                  70                  75                  80

Leu Ala Phe Asp Glu Phe Asp Glu Leu Ala Gly Asp Arg Ala Tyr Ala
                85                  90                  95

Asp Asp Lys Ala Ile Val Gly Gly Ile Ala Arg Leu Asp Gly Arg Pro
            100                 105                 110

Val Met Ile Ile Gly His Gln Lys Gly Arg Glu Thr Lys Glu Lys Ile
        115                 120                 125

Arg Arg Asn Phe Gly Met Pro Ala Pro Glu Gly Tyr Arg Lys Ala Leu
    130                 135                 140

Arg Leu Met Gln Met Ala Glu Arg Phe Lys Met Pro Ile Ile Thr Phe
145                 150                 155                 160

Ile Asp Thr Pro Gly Ala Tyr Pro Gly Val Gly Ala Glu Glu Arg Gly
                165                 170                 175

Gln Ser Glu Ala Ile Ala Arg Asn Leu Arg Glu Met Ser Arg Leu Gly
            180                 185                 190

Val Pro Val Val Cys Thr Val Ile Gly Glu Gly Gly Ser Gly Gly Ala
        195                 200                 205

Leu Ala Ile Gly Val Gly Asp Lys Val Asn Met Leu Gln Tyr Ser Thr
    210                 215                 220

Tyr Ser Val Ile Ser Pro Glu Gly Cys Ala Ser Ile Leu Trp Lys Ser
225                 230                 235                 240

Ala Asp Lys Ala Pro Leu Ala Ala Glu Ala Met Gly Ile Ile Ala Pro
                245                 250                 255

Arg Leu Lys Glu Leu Lys Leu Ile Asp Ser Ile Ile Pro Glu Pro Leu
            260                 265                 270
```

```
Gly Gly Ala His Arg Asn Pro Glu Ala Met Ala Ala Ser Leu Lys Ala
            275                 280                 285

Gln Leu Leu Ala Asp Leu Ala Asp Leu Asp Val Leu Ser Thr Glu Asp
        290                 295                 300

Leu Lys Asn Arg Arg Tyr Gln Arg Leu Met Ser Tyr Gly Tyr Ala
305                 310                 315

<210> SEQ ID NO 5
<211> LENGTH: 471
<212> TYPE: DNA
<213> ORGANISM: Escherichia coli
<220> FEATURE:
<221> NAME/KEY: misc_feature
<223> OTHER INFORMATION: Acetyl-CoA carboxylase biotin carboxyl carrier
      protein

<400> SEQUENCE: 5
atggatattc gtaagattaa aaaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt    240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a              471

<210> SEQ ID NO 6
<211> LENGTH: 156
<212> TYPE: PRT
<213> ORGANISM: Escherichia coli
<220> FEATURE:
<221> NAME/KEY: MISC_FEATURE
<223> OTHER INFORMATION: Acetyl-CoA carboxylase biotin carboxyl carrier
      protein

<400> SEQUENCE: 6

Met Asp Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 7
<211> LENGTH: 1350
<212> TYPE: DNA
<213> ORGANISM: Escherichia coli
<220> FEATURE:
<221> NAME/KEY: misc_feature
<223> OTHER INFORMATION: Acetyl-CoA biotin carboxylase

<400> SEQUENCE: 7

| | | | | | |
|---|---|---|---|---|---|
| atgctggata | aaattgttat | tgccaaccgc | ggcgagattg | cattgcgtat | tcttcgtgcc | 60 |
| tgtaaagaac | tgggcatcaa | gactgtcgct | gtgcactcca | gcgcggatcg | cgatctaaaa | 120 |
| cacgtattac | tggcagatga | aacggtctgt | attggccctg | ctccgtcagt | aaaaagttat | 180 |
| ctgaacatcc | cggcaatcat | cagcgccgct | gaaatcaccg | cgcagtagc | aatccatccg | 240 |
| ggttacggct | tcctctccga | aacgccaac | tttgccgagc | aggttgaacg | ctccggcttt | 300 |
| atcttcattg | gcccgaaagc | agaaaccatt | cgcctgatgg | gcgacaaagt | atccgcaatc | 360 |
| gcggcgatga | aaaagcggg | cgtcccttgc | gtaccgggtt | ctgacggccc | gctgggcgac | 420 |
| gatatggata | aaaccgtgc | cattgctaaa | cgcattggtt | atccggtgat | tatcaaagcc | 480 |
| tccggcggcg | gcggcggtcg | cggtatgcgc | gtagtgcgcg | cgacgctga | actggcacaa | 540 |
| tccatctcca | tgacccgtgc | ggaagcgaaa | gctgctttca | gcaacgatat | ggtttacatg | 600 |
| gagaaatacc | tggaaaatcc | tcgccacgtc | gagattcagg | tactggctga | cggtcagggc | 660 |
| aacgctatct | atctggcgga | acgtgactgc | tccatgcaac | gccgccacca | gaaagtggtc | 720 |
| gaagaagcgc | cagcaccggg | cattaccccg | gaactgcgtc | gctacatcgg | cgaacgttgc | 780 |
| gctaaagcgt | gtgttgatat | cggctatcgc | ggtgcaggta | ctttcgagtt | cctgttcgaa | 840 |
| aacggcgagt | ctatttcat | cgaaatgaac | accgtattc | aggtagaaca | cccggttaca | 900 |
| gaaatgatca | ccggcgttga | cctgatcaaa | gaacagctgc | gtatcgctgc | cggtcaaccg | 960 |
| ctgtcgatca | agcaagaaga | agttcacgtt | cgcggccatg | cggtggaatg | tcgtatcaac | 1020 |
| gccgaagatc | cgaacaccctt | cctgccaagt | ccgggcaaaa | tcacccgttt | ccacgcacct | 1080 |
| ggcggttttg | cgctacgttg | ggagtctcat | atctacgcgg | gctacaccgt | accgccgtac | 1140 |
| tatgactcaa | tgatcggtaa | gctgatttgc | tacggtgaaa | accgtgacgt | ggcgattgcc | 1200 |
| cgcatgaaga | atgcgctgca | ggagctgatc | atcgacggta | tcaaaaccaa | cgttgatctg | 1260 |
| cagatccgca | tcatgaatga | cgagaacttc | cagcatggtg | gcactaacat | ccactatctg | 1320 |
| gagaaaaaac | tcggtcttca | ggaaaaataa | | | | 1350 |

<210> SEQ ID NO 8
<211> LENGTH: 449
<212> TYPE: PRT
<213> ORGANISM: Escherichia coli
<220> FEATURE:
<221> NAME/KEY: MISC_FEATURE
<223> OTHER INFORMATION: Acetyl-CoA biotin carboxylase

<400> SEQUENCE: 8

Met Leu Asp Lys Ile Val Ile Ala Asn Arg Gly Glu Ile Ala Leu Arg
1               5                   10                  15

Ile Leu Arg Ala Cys Lys Glu Leu Gly Ile Lys Thr Val Ala Val His
            20                  25                  30

Ser Ser Ala Asp Arg Asp Leu Lys His Val Leu Leu Ala Asp Glu Thr
        35                  40                  45

Val Cys Ile Gly Pro Ala Pro Ser Val Lys Ser Tyr Leu Asn Ile Pro
    50                  55                  60

```
Ala Ile Ile Ser Ala Ala Glu Ile Thr Gly Ala Val Ala Ile His Pro
 65                  70                  75                  80

Gly Tyr Gly Phe Leu Ser Glu Asn Ala Asn Phe Ala Glu Gln Val Glu
             85                  90                  95

Arg Ser Gly Phe Ile Phe Ile Gly Pro Lys Ala Glu Thr Ile Arg Leu
            100                 105                 110

Met Gly Asp Lys Val Ser Ala Ile Ala Ala Met Lys Lys Ala Gly Val
        115                 120                 125

Pro Cys Val Pro Gly Ser Asp Gly Pro Leu Gly Asp Asp Met Asp Lys
    130                 135                 140

Asn Arg Ala Ile Ala Lys Arg Ile Gly Tyr Pro Val Ile Ile Lys Ala
145                 150                 155                 160

Ser Gly Gly Gly Gly Arg Gly Met Arg Val Val Arg Gly Asp Ala
                165                 170                 175

Glu Leu Ala Gln Ser Ile Ser Met Thr Arg Ala Glu Ala Lys Ala Ala
                180                 185                 190

Phe Ser Asn Asp Met Val Tyr Met Glu Lys Tyr Leu Glu Asn Pro Arg
            195                 200                 205

His Val Glu Ile Gln Val Leu Ala Asp Gly Gln Gly Asn Ala Ile Tyr
    210                 215                 220

Leu Ala Glu Arg Asp Cys Ser Met Gln Arg His Gln Lys Val Val
225                 230                 235                 240

Glu Glu Ala Pro Ala Pro Gly Ile Thr Pro Glu Leu Arg Arg Tyr Ile
                245                 250                 255

Gly Glu Arg Cys Ala Lys Ala Cys Val Asp Ile Gly Tyr Arg Gly Ala
            260                 265                 270

Gly Thr Phe Glu Phe Leu Phe Glu Asn Gly Glu Phe Tyr Phe Ile Glu
        275                 280                 285

Met Asn Thr Arg Ile Gln Val Glu His Pro Val Thr Glu Met Ile Thr
    290                 295                 300

Gly Val Asp Leu Ile Lys Glu Gln Leu Arg Ile Ala Ala Gly Gln Pro
305                 310                 315                 320

Leu Ser Ile Lys Gln Glu Glu Val His Val Arg Gly His Ala Val Glu
                325                 330                 335

Cys Arg Ile Asn Ala Glu Asp Pro Asn Thr Phe Leu Pro Ser Pro Gly
            340                 345                 350

Lys Ile Thr Arg Phe His Ala Pro Gly Gly Phe Gly Val Arg Trp Glu
        355                 360                 365

Ser His Ile Tyr Ala Gly Tyr Thr Val Pro Pro Tyr Tyr Asp Ser Met
    370                 375                 380

Ile Gly Lys Leu Ile Cys Tyr Gly Glu Asn Arg Asp Val Ala Ile Ala
385                 390                 395                 400

Arg Met Lys Asn Ala Leu Gln Glu Leu Ile Ile Asp Gly Ile Lys Thr
                405                 410                 415

Asn Val Asp Leu Gln Ile Arg Ile Met Asn Asp Glu Asn Phe Gln His
            420                 425                 430

Gly Gly Thr Asn Ile His Tyr Leu Glu Lys Lys Leu Gly Leu Gln Glu
        435                 440                 445

Lys
```

<210> SEQ ID NO 9
<211> LENGTH: 915
<212> TYPE: DNA

<213> ORGANISM: Escherichia coli
<220> FEATURE:
<221> NAME/KEY: misc_feature
<223> OTHER INFORMATION: Acetyl-CoA carboxylase transferase subunit beta

<400> SEQUENCE: 9

```
atgagctgga ttgaacgaat taaaagcaac attactccca cccgcaaggc gagcattcct      60
gaagggtgt ggactaagtg tgatagctgc ggtcaggttt ataccgcgc tgagctggaa      120
cgtaatcttg aggtctgtcc gaagtgtgac catcacatgc gtatgacagc gcgtaatcgc    180
ctgcatagcc tgttagatga aggaagcctt gtggagctgg gtagcgagct tgagccgaaa   240
gatgtgctga agtttcgtga ctccaagaag tataaagacc gtctggcatc tgcgcagaaa   300
gaaaccggcg aaaaagatgc gctggtggtg atgaaaggca ctctgtatgg aatgccggtt   360
gtcgctgcgg cattcgagtt cgcctttatg ggcggttcaa tggggtctgt tgtgggtgca   420
cgtttcgtgc gtgccgttga gcaggcgctg aagataact gcccgctgat ctgcttctcc    480
gcctctggtg gcgcacgtat gcaggaagca ctgatgtcgc tgatgcagat ggcgaaaacc   540
tctgcggcac tggcaaaaat gcaggagcgc ggcttgccgt acatctccgt gctgaccgac   600
ccgacgatgg gcggtgtttc tgcaagtttc gccatgctgg gcgatctcaa catcgctgaa   660
ccgaaagcgt taatcggctt gccggtccg cgtgttatcg aacagaccgt tcgcgaaaaa    720
ctgccgcctg gattccagcg cagtgaattc ctgatcgaga aaggcgcgat cgacatgatc   780
gtccgtcgtc cggaaatgcg cctgaaactg gcgagcattc tggcgaagtt gatgaatctg   840
ccagcgccga atcctgaagc gccgcgtgaa ggcgtagtgg tacccccggt accggatcag   900
gaacctgagg cctga                                                    915
```

<210> SEQ ID NO 10
<211> LENGTH: 304
<212> TYPE: PRT
<213> ORGANISM: Escherichia coli
<220> FEATURE:
<221> NAME/KEY: MISC_FEATURE
<223> OTHER INFORMATION: Acetyl-CoA carboxylase transferase subunit beta

<400> SEQUENCE: 10

```
Met Ser Trp Ile Glu Arg Ile Lys Ser Asn Ile Thr Pro Thr Arg Lys
1               5                   10                  15

Ala Ser Ile Pro Glu Gly Val Trp Thr Lys Cys Asp Ser Cys Gly Gln
            20                  25                  30

Val Leu Tyr Arg Ala Glu Leu Glu Arg Asn Leu Glu Val Cys Pro Lys
        35                  40                  45

Cys Asp His His Met Arg Met Thr Ala Arg Asn Arg Leu His Ser Leu
    50                  55                  60

Leu Asp Glu Gly Ser Leu Val Glu Leu Gly Ser Glu Leu Glu Pro Lys
65                  70                  75                  80

Asp Val Leu Lys Phe Arg Asp Ser Lys Lys Tyr Lys Asp Arg Leu Ala
                85                  90                  95

Ser Ala Gln Lys Glu Thr Gly Glu Lys Asp Ala Leu Val Val Met Lys
            100                 105                 110

Gly Thr Leu Tyr Gly Met Pro Val Val Ala Ala Phe Glu Phe Ala
        115                 120                 125

Phe Met Gly Gly Ser Met Gly Ser Val Val Gly Ala Arg Phe Val Arg
    130                 135                 140
```

```
Ala Val Glu Gln Ala Leu Glu Asp Asn Cys Pro Leu Ile Cys Phe Ser
145                 150                 155                 160

Ala Ser Gly Gly Ala Arg Met Gln Glu Ala Leu Met Ser Leu Met Gln
            165                 170                 175

Met Ala Lys Thr Ser Ala Ala Leu Ala Lys Met Gln Glu Arg Gly Leu
        180                 185                 190

Pro Tyr Ile Ser Val Leu Thr Asp Pro Thr Met Gly Gly Val Ser Ala
    195                 200                 205

Ser Phe Ala Met Leu Gly Asp Leu Asn Ile Ala Glu Pro Lys Ala Leu
210                 215                 220

Ile Gly Phe Ala Gly Pro Arg Val Ile Glu Gln Thr Val Arg Glu Lys
225                 230                 235                 240

Leu Pro Pro Gly Phe Gln Arg Ser Glu Phe Leu Ile Glu Lys Gly Ala
                245                 250                 255

Ile Asp Met Ile Val Arg Arg Pro Glu Met Arg Leu Lys Leu Ala Ser
            260                 265                 270

Ile Leu Ala Lys Leu Met Asn Leu Pro Ala Pro Asn Pro Glu Ala Pro
        275                 280                 285

Arg Glu Gly Val Val Val Pro Pro Val Pro Asp Gln Glu Pro Glu Ala
    290                 295                 300
```

<210> SEQ ID NO 11
<211> LENGTH: 5553
<212> TYPE: DNA
<213> ORGANISM: Yarrowia lipolytica
<220> FEATURE:
<221> NAME/KEY: misc_feature
<223> OTHER INFORMATION: fatty acid synthase subunit alpha

<400> SEQUENCE: 11

```
atgcaccccg aagtcgaaca agaactcgcc cacgtgctcc tgacggagct gctggcctac      60
caatttgcct cgcccgtgcg atggatcgag acccaggacg tgctgttcaa gcagttcaat     120
gtcgagcgag tcgtcgaagt cggcccatcc ccaactctcg ccggcatggc ccagcgaacc     180
cttaagtcca agtacgagtc atacgacgct gctctgtctc tgcagcgaga gatcctgtgt     240
tactccaagg accagaagga catctactac cttgccgatg aggccgatga agcccctgcc     300
cccgctgctg gtggtgatgc ccccgctgct cctgccgctg ccgctcctgc cgccgctgcc     360
gctcctgctg ccgctgccgc cccctctggc ccgttgcca  aggttgagga cgcccccgtc     420
aaggcccagg agattctcca cgccctggtc gcccataagc tcaagaagac ccccgagcag     480
gtgcccctgt ccaaggccat caaagacctt gttggtggta gtctaccat  ccagaacgag     540 attctcggtg atctcggaaa ggaatttggt gccacccctg agaagcccga ggatactccc     600
cttggcgagc tggctgagtc cttccaggcc tcctttgacg caagctcgg  taagcagtct     660 tcttctctca ttgcccgact catgtcctcc aagatgcccg agggttctc  tctcacctct     720 gctcgatcct acctcgacag cagatggggc ctggctgctg ccgacagga ctccgttctg     780 cttgttgctc tgatgaacga acccaagaac cgacttggct ctgaagccga ggccaaggcc     840
tacctcgacg agcagaccca gaagtatgct gcttctgccg tcttaacct  gtctgccccc     900 gctggtggtg ccgagggtgg caatggcggt ggcgccgtca ttgactccgc tgccttttgac    960 gctctcacca aggaccagcg ataccgtgtc cagcagcaac tcgagttgtt  tgccaactac    1020
ctgaagcagg atctgcgaca gggctccaag gtggctgctg cccagaagga ggccatggat    1080
attctgcaag ctgaactgga tctttggaac tccgagcacg cgcaggtcta cgctgagggc    1140
```

```
atcaagcccg ccttctctgc cctgaaggcc cgtgtctacg actcgtactg gaactgggct    1200
cgacaggact cgctctccat gtactttgac attgttttcg gtcgtctctc caccgttgac    1260
cgagagatta tggctaagtg tatccacctg atgaaccgaa ccaaccacaa cctgatcgac    1320
tacatgcagt accacatgga ccacgtcccc gttcacaagg gagccaccta cgagcttgcc    1380
aagcagctcg gtctgcagct cctcgagaac tgtaaggaga ctctcaccga ggcccccgtc    1440
tacaaggatg tctcttaccc cactggaccc cagaccacca ttgatgtcaa gggtaacatt    1500
gtttacaacg aggtgccccg acccaatgtc cgaaagctcg agcagtatgt ccacgagatg    1560
gcctgtggtg gtgagctgac caaggacccc tcttttgttg gagaaggtgt ccagggcgag    1620
ctcaagaagc tgtactctca gatctctgct cttgccaaga cccagaccgg ctctacccte    1680 gacatcgagg ctctgtactc cgacctggtc gctaagatct cccaggccga ggacgcgtcc    1740
aagcctgtcg ttgagaacaa ggctgtttct gcctccatca ctcccggcac tctccctttt    1800
ctccacatca agaagaagac cgaacttggt gcctggaatt acgacagcga gaccaccgcc    1860
acctacctcg atggtcttga ggttgctgcc cgtgatggtc tcactttcca gggcaagact    1920
gctctgatca ccggtgctgg tgctggctcc attggtgcct caatcctcca gggtctcatt    1980
tccggaggct gcaaagtcat tgtcacaacc tctcgatact cccgaaaggt gaccgagtac    2040
taccagtccc tctacaccaa gttcggtgct aagggttcca ctctgattgt tgtccccttc    2100
aaccaaggct ccaagaagga cgtggacgag ctggtgtcgt tcatctacaa cgaccccaag    2160
aacggcggtc ttggctggga tctggacttt gttgttccct ttgctgctct gcccgagaac    2220
ggtattgagc tggagcacat tgactcaaag tccgagcttg cccatcgaat catgctcacc    2280
aacctcctgc gtctgcttgg taacgtcaag aagcagaaag tggcccattc ctacgagact    2340
cgacccgccc aggtcatgct gcccctgtcg cccaaccatg gcaacttcgg ctccgatggt    2400
ctgtactccg agtccaagat ctctctcgag actctgttca accggtggca caccgagtcc    2460
tggggctctt atctcaccat tgttggtgtg gtgattggct ggacccgagg taccggtctg    2520
atgagcgcca acaacatcac cgccgagggt ctggagcagc tcggcgtccg aaccttctcc    2580
cagactgaga tggcctttc catcatgggt ctcatgacca aggacattgt gcgactggcc    2640
cagaactccc ccgtgtgggc cgatctcaac ggtggcttcc agtacattcc cgacctcaag    2700
ggagttgttg aaagatccg acgagacatt gtggagacct ccgagatccg acgggctgtg    2760
gctcaggaga ctgccattga acagaaggtg gtcaacggcc cccacgccga tcttccttac    2820
cagaaggtcg aggtcaagcc ccgagccaac ctcaagtttg acttccccac cctcaaatcc    2880
tacgccgagg tcaaggagct gtctcctgct ggtgatgctc tggagggtct tctggatctc    2940
tcttccgtca ttgttgtcac tggtttcgcc gaggtcggtc cttggggtaa cgcccgaacc    3000
cgatgggaca tggaggccaa cggtgtcttc tcccttgagg gtgccattga gatggcctgg    3060
atcatgggtc tgatcaagca ccacaatggt cccctgcccg gcatgcctca gtactctggc    3120
tggatcgata ccaagaccaa gcagcccgtc gatgaccgag atatcaagac caagtacgag    3180
gactacctgc ttgagcacgc cggtatccga ctcattgagc ctgagctgtt ccacggctac    3240
aaccccaaga gaagaccttt cctccaggag gttattgtgg agcacgatct cgagcccttt    3300
gaggcctcca aggagtctgc tgagcaattt gctctcgagc agggcgcgaa cgttgagatc    3360
ttcgccgtcc ccgagtccga ccagtggact gtgcgacttc tcaagggcgc caagctcctc    3420
attcccaagg ccctcaagtt tgaccgactt gtggccggcc agattcccac tggatgggat    3480
gcccgacgat acggtattcc cgaggacatt tgtgaccagg ttgaccccat cactctgtac    3540
```

-continued

```
gctcttgtct ccactgttga ggctctgttg gcctccggta ttaccgaccc ctacgagttc    3600
tacaagtacg tccacgtgtc cgaggtcggt aactgttccg gttccggtat gggtggtatc    3660
accgccctgc gaggcatgtt caaggaccgg ttcatggaca agcctgttca gaacgatatt    3720
ctccaggagt ccttcatcaa caccatgtct gcctgggtca acatgttgct gctctccctct   3780 tccggtccca tcaagacccc cgttggagct tgtgccactg ctgtcgagtc tgtggacatt    3840
ggttgcgaaa ccattctgtc cggcaaggcc agaatctgtc tggtcggtgg ttacgatgat    3900
ttccaggagg agtcttctca ggagtttgca acatgaacg caacatccaa cgctgagacc     3960
gagatcactc acggccgaac tccggccgag atgtctcgac ccatcacttc cacacgagcc    4020
ggtttcatgg aggctcaggg tgctggaacc caggtgctga tggccgccga cctcgccatc    4080
gccatgggtg tgcccatcta ctgtatcgtt ggttacgtca acactgccac cgacaagatt    4140
ggccgatctg tgcctgctcc cggtaagggt atcctgacca ctgctcgaga gcaccagact    4200
ctcaaacacg ccaaccctct cctcaacatc aagtaccgaa agcgacagct cgattctcga    4260
ctccgagaca ttaagcgatg ggctgagggc gaaatggagg ctattgacat tgagcttgac    4320
gacgtgtctg acgccgacaa ggagtccttc atccaggagc gatctgccca catccagtct    4380
cagtccgatc gaatgatccg agaggctaag aactcttggg gtaacgcctt tttcaagcag    4440
gacgcccgaa tctcccccat ccgaggagcg ctggcaacct acggtctcac cattgatgac    4500
atctccgtcg cttcttttcca tggtacatcc accaaggcca acgagaagaa cgagaccacc    4560
accgtcaacg ccatgctgga gcatctcggc agaacccggg gtaaccctgt ctacggtatc    4620
ttccagaagt accttactgg tcaccccaag ggagctgctg gtgcctggat gctcaacgga    4680
gccatccaat gcctcaactc tggtatcatc cctggtaacc gaaacgccga taacgtggat    4740
gcctactttg agcagtgcca gcacgtggtg ttcccctcgc gatctctgca gaccgatggc    4800
ctcaaggctg cttccgtgac ctcctttggt ttcggtcaga agggtgccca ggccattgtc    4860
atccaccccg actacctgta cgctgccctg acaccctccg agtactccga gtacaccacc    4920
cgagtcgccc agcgatacaa gaaggcttac cgatactacc acaacgccat tgccgaggag    4980
tccatgttcc aggccaagga caaggctccc tactctgctg agctggagca ggaggtctac    5040
ctggatcctc ttgtgcgagt ccaccagaac gaggacaccg agcagtactc cttcaacgcc    5100
aaggacctcg ctgcctccgc ctttgtcaag aactcccaca aggacaccgc caaggtgctt    5160
gccaacctca cctcccaggt gtccggttct ggtaagaacg ttggtgtcga cgttgaggcc    5220
atctccgcca tcaacattga taacgacacc ttccttgacc gaaacttcac cgccaacgag    5280
caggcctact gcttcaaggc cccctccccc cagtcttctt tcgctggcac ttggtctgcc    5340
aaggaggctg ttttcaagtc tctgggcgtc aagtcccagg gcggaggagc tgagctcaag    5400
tccattgaga tcactcgaga tggcaacgga gctcccgtcg tggttcttca cggagctgcc    5460
aaggacgctg ctgcttctaa gggtatctcc accgtcaagg tgtccatttc ccatgacgac    5520
tctcaggccg tggctgttgc tgttgccgag tag                                 5553
```

<210> SEQ ID NO 12
<211> LENGTH: 1850
<212> TYPE: PRT
<213> ORGANISM: Yarrowia lipolytica
<220> FEATURE:
<221> NAME/KEY: MISC_FEATURE
<223> OTHER INFORMATION: fatty acid synthase subunit alpha

<400> SEQUENCE: 12

```
Met His Pro Glu Val Glu Gln Glu Leu Ala His Val Leu Leu Thr Glu
1               5                   10                  15

Leu Leu Ala Tyr Gln Phe Ala Ser Pro Val Arg Trp Ile Glu Thr Gln
                20                  25                  30

Asp Val Leu Phe Lys Gln Phe Asn Val Glu Arg Val Glu Val Gly
            35                  40                  45

Pro Ser Pro Thr Leu Ala Gly Met Ala Gln Arg Thr Leu Lys Ser Lys
        50                  55                  60

Tyr Glu Ser Tyr Asp Ala Ala Leu Ser Leu Gln Arg Glu Ile Leu Cys
65                  70                  75                  80

Tyr Ser Lys Asp Gln Lys Asp Ile Tyr Tyr Leu Ala Asp Glu Ala Asp
                85                  90                  95

Glu Ala Pro Ala Pro Ala Ala Gly Gly Asp Ala Pro Ala Ala Pro Ala
            100                 105                 110

Ala Ala Ala Pro Ala Ala Ala Ala Ala Pro Ala Ala Ala Ala Ala Pro
        115                 120                 125

Ser Gly Pro Val Ala Lys Val Glu Asp Ala Pro Val Lys Ala Gln Glu
    130                 135                 140

Ile Leu His Ala Leu Val Ala His Lys Leu Lys Lys Thr Pro Glu Gln
145                 150                 155                 160

Val Pro Leu Ser Lys Ala Ile Lys Asp Leu Val Gly Gly Lys Ser Thr
                165                 170                 175

Ile Gln Asn Glu Ile Leu Gly Asp Leu Gly Lys Glu Phe Gly Ala Thr
            180                 185                 190

Pro Glu Lys Pro Glu Asp Thr Pro Leu Gly Glu Leu Ala Glu Ser Phe
        195                 200                 205

Gln Ala Ser Phe Asp Gly Lys Leu Gly Lys Gln Ser Ser Ser Leu Ile
    210                 215                 220

Ala Arg Leu Met Ser Ser Lys Met Pro Gly Gly Phe Ser Leu Thr Ser
225                 230                 235                 240

Ala Arg Ser Tyr Leu Asp Ser Arg Trp Gly Leu Ala Ala Gly Arg Gln
                245                 250                 255

Asp Ser Val Leu Leu Val Ala Leu Met Asn Glu Pro Lys Asn Arg Leu
            260                 265                 270

Gly Ser Glu Ala Glu Ala Lys Ala Tyr Leu Asp Glu Gln Thr Gln Lys
        275                 280                 285

Tyr Ala Ala Ser Ala Gly Leu Asn Leu Ser Pro Ala Gly Gly Ala
    290                 295                 300

Glu Gly Gly Asn Gly Gly Ala Val Ile Asp Ser Ala Ala Phe Asp
305                 310                 315                 320

Ala Leu Thr Lys Asp Gln Arg Tyr Leu Val Gln Gln Leu Glu Leu
                325                 330                 335

Phe Ala Asn Tyr Leu Lys Gln Asp Leu Arg Gln Gly Ser Lys Val Ala
            340                 345                 350

Ala Ala Gln Lys Glu Ala Met Asp Ile Leu Gln Ala Glu Leu Asp Leu
        355                 360                 365

Trp Asn Ser Glu His Gly Glu Val Tyr Ala Glu Gly Ile Lys Pro Ala
    370                 375                 380

Phe Ser Ala Leu Lys Ala Arg Val Tyr Asp Ser Tyr Trp Asn Trp Ala
385                 390                 395                 400

Arg Gln Asp Ser Leu Ser Met Tyr Phe Asp Ile Val Phe Gly Arg Leu
                405                 410                 415
```

-continued

```
Ser Thr Val Asp Arg Glu Ile Met Ala Lys Cys Ile His Leu Met Asn
                420                 425                 430

Arg Thr Asn His Asn Leu Ile Asp Tyr Met Gln Tyr His Met Asp His
            435                 440                 445

Val Pro Val His Lys Gly Ala Thr Tyr Glu Leu Ala Lys Gln Leu Gly
        450                 455                 460

Leu Gln Leu Leu Glu Asn Cys Lys Glu Thr Leu Thr Glu Ala Pro Val
465                 470                 475                 480

Tyr Lys Asp Val Ser Tyr Pro Thr Gly Pro Gln Thr Thr Ile Asp Val
                485                 490                 495

Lys Gly Asn Ile Val Tyr Asn Glu Val Pro Arg Pro Asn Val Arg Lys
            500                 505                 510

Leu Glu Gln Tyr Val His Glu Met Ala Cys Gly Gly Glu Leu Thr Lys
        515                 520                 525

Asp Pro Ser Phe Val Gly Glu Gly Val Gln Gly Glu Leu Lys Lys Leu
    530                 535                 540

Tyr Ser Gln Ile Ser Ala Leu Ala Lys Thr Gln Thr Gly Ser Thr Leu
545                 550                 555                 560

Asp Ile Glu Ala Leu Tyr Ser Asp Leu Val Ala Lys Ile Ser Gln Ala
                565                 570                 575

Glu Asp Ala Ser Lys Pro Val Val Glu Asn Lys Ala Val Ser Ala Ser
            580                 585                 590

Ile Thr Pro Gly Thr Leu Pro Phe Leu His Ile Lys Lys Lys Thr Glu
        595                 600                 605

Leu Gly Ala Trp Asn Tyr Asp Ser Glu Thr Thr Ala Thr Tyr Leu Asp
    610                 615                 620

Gly Leu Glu Val Ala Ala Arg Asp Gly Leu Thr Phe Gln Gly Lys Thr
625                 630                 635                 640

Ala Leu Ile Thr Gly Ala Gly Ala Gly Ser Ile Gly Ala Ser Ile Leu
                645                 650                 655

Gln Gly Leu Ile Ser Gly Gly Cys Lys Val Ile Val Thr Thr Ser Arg
            660                 665                 670

Tyr Ser Arg Lys Val Thr Glu Tyr Tyr Gln Ser Leu Tyr Thr Lys Phe
        675                 680                 685

Gly Ala Lys Gly Ser Thr Leu Ile Val Val Pro Phe Asn Gln Gly Ser
    690                 695                 700

Lys Lys Asp Val Asp Glu Leu Val Ser Phe Ile Tyr Asn Asp Pro Lys
705                 710                 715                 720

Asn Gly Gly Leu Gly Trp Asp Leu Asp Phe Val Val Pro Phe Ala Ala
                725                 730                 735

Leu Pro Glu Asn Gly Ile Glu Leu Glu His Ile Asp Ser Lys Ser Glu
            740                 745                 750

Leu Ala His Arg Ile Met Leu Thr Asn Leu Leu Arg Leu Leu Gly Asn
        755                 760                 765

Val Lys Lys Gln Lys Val Ala His Ser Tyr Glu Thr Arg Pro Ala Gln
    770                 775                 780

Val Met Leu Pro Leu Ser Pro Asn His Gly Asn Phe Gly Ser Asp Gly
785                 790                 795                 800

Leu Tyr Ser Glu Ser Lys Ile Ser Leu Glu Thr Leu Phe Asn Arg Trp
                805                 810                 815

His Thr Glu Ser Trp Gly Ser Tyr Leu Thr Ile Val Gly Val Val Ile
            820                 825                 830

Gly Trp Thr Arg Gly Thr Gly Leu Met Ser Ala Asn Asn Ile Thr Ala
```

-continued

```
            835                 840                 845
Glu Gly Leu Glu Gln Leu Gly Val Arg Thr Phe Ser Gln Thr Glu Met
            850                 855                 860
Ala Phe Ser Ile Met Gly Leu Met Thr Lys Asp Ile Val Arg Leu Ala
865                 870                 875                 880
Gln Asn Ser Pro Val Trp Ala Asp Leu Asn Gly Gly Phe Gln Tyr Ile
                    885                 890                 895
Pro Asp Leu Lys Gly Val Val Gly Lys Ile Arg Arg Asp Ile Val Glu
                900                 905                 910
Thr Ser Glu Ile Arg Arg Ala Val Ala Gln Glu Thr Ala Ile Glu Gln
                915                 920                 925
Lys Val Val Asn Gly Pro His Ala Asp Leu Pro Tyr Gln Lys Val Glu
            930                 935                 940
Val Lys Pro Arg Ala Asn Leu Lys Phe Asp Phe Pro Thr Leu Lys Ser
945                 950                 955                 960
Tyr Ala Glu Val Lys Glu Leu Ser Pro Ala Gly Asp Ala Leu Glu Gly
                    965                 970                 975
Leu Leu Asp Leu Ser Ser Val Ile Val Val Thr Gly Phe Ala Glu Val
                980                 985                 990
Gly Pro Trp Gly Asn Ala Arg Thr Arg Trp Asp Met Glu Ala Asn Gly
                995                 1000                1005
Val Phe Ser Leu Glu Gly Ala Ile Glu Met Ala Trp Ile Met Gly
    1010                1015                1020
Leu Ile Lys His His Asn Gly Pro Leu Pro Gly Met Pro Gln Tyr
    1025                1030                1035
Ser Gly Trp Ile Asp Thr Lys Thr Lys Gln Pro Val Asp Asp Arg
    1040                1045                1050
Asp Ile Lys Thr Lys Tyr Glu Asp Tyr Leu Leu Glu His Ala Gly
    1055                1060                1065
Ile Arg Leu Ile Glu Pro Glu Leu Phe His Gly Tyr Asn Pro Lys
    1070                1075                1080
Lys Lys Thr Phe Leu Gln Glu Val Ile Val Glu His Asp Leu Glu
    1085                1090                1095
Pro Phe Glu Ala Ser Lys Glu Ser Ala Glu Gln Phe Ala Leu Glu
    1100                1105                1110
Gln Gly Ala Asn Val Glu Ile Phe Ala Val Pro Glu Ser Asp Gln
    1115                1120                1125
Trp Thr Val Arg Leu Leu Lys Gly Ala Lys Leu Leu Ile Pro Lys
    1130                1135                1140
Ala Leu Lys Phe Asp Arg Leu Val Ala Gly Gln Ile Pro Thr Gly
    1145                1150                1155
Trp Asp Ala Arg Arg Tyr Gly Ile Pro Glu Asp Ile Cys Asp Gln
    1160                1165                1170
Val Asp Pro Ile Thr Leu Tyr Ala Leu Val Ser Thr Val Glu Ala
    1175                1180                1185
Leu Leu Ala Ser Gly Ile Thr Asp Pro Tyr Glu Phe Tyr Lys Tyr
    1190                1195                1200
Val His Val Ser Glu Val Gly Asn Cys Ser Gly Ser Gly Met Gly
    1205                1210                1215
Gly Ile Thr Ala Leu Arg Gly Met Phe Lys Asp Arg Phe Met Asp
    1220                1225                1230
Lys Pro Val Gln Asn Asp Ile Leu Gln Glu Ser Phe Ile Asn Thr
    1235                1240                1245
```

```
Met Ser Ala Trp Val Asn Met Leu Leu Leu Ser Ser Ser Gly Pro
    1250                1255                1260

Ile Lys Thr Pro Val Gly Ala Cys Ala Thr Ala Val Glu Ser Val
    1265                1270                1275

Asp Ile Gly Cys Glu Thr Ile Leu Ser Gly Lys Ala Arg Ile Cys
    1280                1285                1290

Leu Val Gly Gly Tyr Asp Asp Phe Gln Glu Ser Ser Gln Glu
    1295                1300                1305

Phe Ala Asn Met Asn Ala Thr Ser Asn Ala Glu Thr Glu Ile Thr
    1310                1315                1320

His Gly Arg Thr Pro Ala Glu Met Ser Arg Pro Ile Thr Ser Thr
    1325                1330                1335

Arg Ala Gly Phe Met Glu Ala Gln Gly Ala Gly Thr Gln Val Leu
    1340                1345                1350

Met Ala Ala Asp Leu Ala Ile Ala Met Gly Val Pro Ile Tyr Cys
    1355                1360                1365

Ile Val Gly Tyr Val Asn Thr Ala Thr Asp Lys Ile Gly Arg Ser
    1370                1375                1380

Val Pro Ala Pro Gly Lys Gly Ile Leu Thr Thr Ala Arg Glu His
    1385                1390                1395

Gln Thr Leu Lys His Ala Asn Pro Leu Leu Asn Ile Lys Tyr Arg
    1400                1405                1410

Lys Arg Gln Leu Asp Ser Arg Leu Arg Asp Ile Lys Arg Trp Ala
    1415                1420                1425

Glu Gly Glu Met Glu Ala Ile Asp Ile Glu Leu Asp Asp Val Ser
    1430                1435                1440

Asp Ala Asp Lys Glu Ser Phe Ile Gln Glu Arg Ser Ala His Ile
    1445                1450                1455

Gln Ser Gln Ser Asp Arg Met Ile Arg Glu Ala Lys Asn Ser Trp
    1460                1465                1470

Gly Asn Ala Phe Phe Lys Gln Asp Ala Arg Ile Ser Pro Ile Arg
    1475                1480                1485

Gly Ala Leu Ala Thr Tyr Gly Leu Thr Ile Asp Asp Ile Ser Val
    1490                1495                1500

Ala Ser Phe His Gly Thr Ser Thr Lys Ala Asn Glu Lys Asn Glu
    1505                1510                1515

Thr Thr Thr Val Asn Ala Met Leu Glu His Leu Gly Arg Thr Arg
    1520                1525                1530

Gly Asn Pro Val Tyr Gly Ile Phe Gln Lys Tyr Leu Thr Gly His
    1535                1540                1545

Pro Lys Gly Ala Ala Gly Ala Trp Met Leu Asn Gly Ala Ile Gln
    1550                1555                1560

Cys Leu Asn Ser Gly Ile Ile Pro Gly Asn Arg Asn Ala Asp Asn
    1565                1570                1575

Val Asp Ala Tyr Phe Glu Gln Cys Gln His Val Val Phe Pro Ser
    1580                1585                1590

Arg Ser Leu Gln Thr Asp Gly Leu Lys Ala Ala Ser Val Thr Ser
    1595                1600                1605

Phe Gly Phe Gly Gln Lys Gly Ala Gln Ala Ile Val Ile His Pro
    1610                1615                1620

Asp Tyr Leu Tyr Ala Ala Leu Thr Pro Ser Glu Tyr Ser Glu Tyr
    1625                1630                1635
```

| | | | | | | | | | | | |
|---|---|---|---|---|---|---|---|---|---|---|---|
|Thr|Thr|Arg|Val|Ala|Gln|Arg|Tyr|Lys|Lys|Ala|Tyr|Arg|Tyr|Tyr|
| |1640| | | |1645| | | |1650| | | | | |

Thr Thr Arg Val Ala Gln Arg Tyr Lys Lys Ala Tyr Arg Tyr Tyr
            1640                1645                1650

His Asn Ala Ile Ala Glu Glu Ser Met Phe Gln Ala Lys Asp Lys
    1655                1660                1665

Ala Pro Tyr Ser Ala Glu Leu Glu Gln Glu Val Tyr Leu Asp Pro
    1670                1675                1680

Leu Val Arg Val His Gln Asn Glu Asp Thr Glu Gln Tyr Ser Phe
    1685                1690                1695

Asn Ala Lys Asp Leu Ala Ala Ser Ala Phe Val Lys Asn Ser His
    1700                1705                1710

Lys Asp Thr Ala Lys Val Leu Ala Asn Leu Thr Ser Gln Val Ser
    1715                1720                1725

Gly Ser Gly Lys Asn Val Gly Val Asp Val Glu Ala Ile Ser Ala
    1730                1735                1740

Ile Asn Ile Asp Asn Asp Thr Phe Leu Asp Arg Asn Phe Thr Ala
    1745                1750                1755

Asn Glu Gln Ala Tyr Cys Phe Lys Ala Pro Ser Pro Gln Ser Ser
    1760                1765                1770

Phe Ala Gly Thr Trp Ser Ala Lys Glu Ala Val Phe Lys Ser Leu
    1775                1780                1785

Gly Val Lys Ser Gln Gly Gly Ala Glu Leu Lys Ser Ile Glu
    1790                1795                1800

Ile Thr Arg Asp Gly Asn Gly Ala Pro Val Val Val Leu His Gly
    1805                1810                1815

Ala Ala Lys Asp Ala Ala Ala Ser Lys Gly Ile Ser Thr Val Lys
    1820                1825                1830

Val Ser Ile Ser His Asp Asp Ser Gln Ala Val Ala Val Ala Val
    1835                1840                1845

Ala Glu
    1850

```
<210> SEQ ID NO 13
<211> LENGTH: 6261
<212> TYPE: DNA
<213> ORGANISM: Yarrowia lipolytica
<220> FEATURE:
<221> NAME/KEY: misc_feature
<223> OTHER INFORMATION: fatty acid synthase subunit beta

<400> SEQUENCE: 13
atgtacccta ccacaggtgt caacaccccc cagagcgccg cctcattaag accactggtg      60
ctatcgcacg gccaaactga gcactcgctg ctggtgccca cctctctgta catcaactgc     120
accacgctcc gagaccagtt ctacgcctct ctacctccag ccactgaaga caaggccgac     180
gatgatgagc cctcctcctc cacagagctt ctagctgcct tcctgggatt tactgccaag     240
accgtcgagg aagagcccgg accatacgac gacgttctct ctctcgtgct taacgagttt     300
gagacccggt acttgcgagg taacgacatc cacgctgtgg cctcctcctt gttacaagac     360
gaggacgtgc ctaccaccgt tggtaagatc aagagggtga ttcgagccta ctacgccgca     420
cgaattgcct gcaacggccc catcaaggcc cactcgtcgg ctctgttccg agccgcatct     480
gaagactcgg acaacgtctc tctgtacgcc atcttcggtg ccagggaaa caccgaggac     540 tactttgagg aactgcggga gatttacgac atctaccagg ggctggtcgg cgacttcatt     600
cgggaatgtg gagcccagct tctggcgctg tctcgagatc acattgctgc tgagaaaatt     660
tataccaagg gctttgatat cgtcaagtgg ctggaacacc ccgagaccat cccgactttt     720
```

```
gagtacctaa tttctgctcc catctctgta cccatcatcg gtgttatcca gctggcacac    780
tacgctgtca cctgtcgagt tttgggtctt aatcctggcc aggtccgaga caacctcaag    840
ggtgccactg gccattctca gggtctgatc accgcaattg ccatctctgc ctccgactcg    900
tgggacgagt tctataactc tgcctctcga attctcaaga tcttcttctt catcggtgtc    960
cgtgtccaac aggcttaccc ctccactttc ctgcctccct ccactctgga agacagtgtc   1020
aagcagggtg agggcaagcc cactcccatg ctgtccatcc gagacctgtc tctcaaccag   1080
gttcaggagt tcgtcgatgc caccaacttg catttgcccg aagataagca gatcgtcgtg   1140
tctctgatca atggtcctcg aaacgttgtc gttactggcc ccccccagtc tctgtatggt   1200
ctgtgtcttg tgcttcgaaa acagaaggcc gagaccggtc tggaccaaag ccgagtgccc   1260
cacagtcagc gaaagctcaa attcacacat cgtttcctgc ccatcacctc tcctttccac   1320
tcgtacctgc tggagaagag cacggatctg atcatcaacg acctggagtc ttccggtgtg   1380
gagtttgtgt cctccgagct caaggtgcct gtttacgaca cctttgatgg ctccgtgctg   1440
tctcagctac ccaagggtat cgtcagccgt ctggtcaacc tcatcactca tctgcccgtc   1500
aagtgggaga aggccactca gtttcaggcc tcccacattg tggactttgg tcccggtggc   1560
gcttctggtc ttggtctgtt gacccacaag aacaaggatg aactggagt gcgaactatt    1620 cttgctggtg tcattgacca gcccctcgag ttcggcttca agcaggagct gtttgaccga   1680
caggagtcgt ccattgtttt tgctcaaaac tgggccaagg agttttctcc caagctcgtc   1740
aagatctcct ccaccaacga ggtctatgtc gacaccaaat tctctcgtct gactggccga   1800
gcccccatca tggtcgctgg tatgaccccct accactgtca accccaaatt tgtggctgcc   1860
actatgaact ccggctacca catcgagctt ggtggtggag gctactttgc ccccggtatg   1920
atgaccaagg cccttgaaca cattgagaag aacactcctc ccggatccgg tatcaccatc   1980
aacctgatct acgtcaaccc ctcgactgatt caatggggta ttcctctgat tcaggagctt   2040
cgacagaagg gtttccccat tgaaggtctc accattggtg ccggtgtgcc ctctctggag   2100
gttgctaacg agtggattca ggatctgggc gtcaagcaca tcgccttcaa gcctggatcc   2160
atcgaggcca tctcctcggt gattcgaatc gccaaggcca acccagactt tcctatcatc   2220
cttcagtgga ccggaggtcg aggaggagga catcattcgt ttgaggactt ccacgctccc   2280
attctgcaga tgtactccaa gatccgacga tgcagcaaca ttgtgctgat tgccggatct   2340
ggtttcggtg cttctaccga ctcctaccca tacctcaccg gttcatggtc ccgagacttt   2400
gactaccctc ccatgccctt tgacggtatc ctggttggtt ctcgagtcat ggttgccaag   2460
gaggctttca cttctctggg agccaagcag ctcattgttg actctccggg tgttgaggat   2520
tctgagtggg agaaaaccta cgacaagccc actggtggcg tcatcaccgt tctctccgag   2580
atgggtgagc ctatccacaa gctcgccact cgaggtgtgc tcttctggca cgagatggac   2640
aagaccgtgt tctccctgcc caagaagaag cgtctggaag tgctcaagtc caagcgagcc   2700
tacatcatca gcgtctcaa cgacgacttc agaagacttg gtttgccaa gaacgcccag    2760 ggacaggtgt gtgatctcga agacctcacc tacgcggagg tcatccagcg acttgttgac   2820
ctcatgtacg tgaagaagga aagccgatgg atcgatgtca ctctccgaaa tcttgccggc   2880
actttcattc gacgagttga ggagcgattc tccaccgaga caggtgcctc ttctgtgttg   2940
cagagctttt ccgagctgga ttccgagccc gagaaggttg tcgagcgggt gtttgagctc   3000
ttccctgcct ctactaccca gatcatcaac gctcaagaca aggaccactt cctcatgctg   3060
```

```
tgtctcaacc ccatgcagaa gcccgtgccc ttcatccctg ttctggatga caactttgag    3120
ttcttcttca agaaggactc tctgtggcag tgcgaggacc tcgcagctgt tgtggacgaa    3180
gacgttggac gaatctgtat tcttcagggt cccgttgctg tcaagcactc caagattgtc    3240
aacgagcccg tcaaggagat tctcgactcc atgcacgaag gtcacatcaa gcagctgctt    3300
gaggatggcg agtacgctgg caacatggcc aacatccccc aggtcgaatg ctttggtgga    3360
aagcctgctc agaacttcgg tgacgttgct ctcgactctg tcatggttct tgatgacctc    3420
aacaagaccg tgttcaagat tgagaccggc acctctgctc tgccttctgc tgcagattgg    3480
ttctctctgc tggccggtga caagaactct tggcgacagg tcttcctgtc cactgacacc    3540
attgtgcaga ccaccaagat gatctccaac cctctgcatc gacttctgga gcccatcgca    3600
ggtttgcagg ttgagattga gcaccctgat gagcccgaga caccgtcat ctctgctttc     3660
gagcccatca acggcaaggt caccaaggtg ctggagctgc gaaagggtgc cggagacgtc    3720
atttcgctgc agctgatcga agcgcgtggc gttgaccgag tccccgttgc tcttcctctg    3780
gaattcaagt accagcccca gattggctac gctcccattg ttgaggttat gaccgacagg    3840
aacacccgaa tcaaggagtt ctactggaag ctgtggtttg gccaggactc caagtttgag    3900
attgacaccg acatcaccga ggaaatcatt ggcgatgacg ttaccatctc tggcaaggcc    3960
attgccgact ttgtccacgc tgttggcaac aagggcgagg cctttgttgg tcgatctacc    4020
tctgctggta ctgtcttcgc tcccatggac tttgccattg ttttgggctg gaaggccatt    4080
atcaaggcaa tctttccccg agcaattgat gctgacattc tgcgtctggt acatctgtcc    4140
aacggcttca agatgatgcc tggcgccgac cctctgcaga tgggtgatgt tgtttccgcc    4200
actgccaaga tcgacactgt caagaactcc gctaccggca agactgttgc tgttcgaggt    4260
cttctcaccc gagacggcaa gcctgtcatg gaggttgttt ccgaattctt ctaccgaggc    4320
gaattctccg acttccagaa cactttgag cgacgagagg aggtacccat gcaactgacc    4380
ctcaaggacg ccaaggccgt ggccattctc tgctccaagg agtggttga gtacaatggc    4440
gacgatacca aggacctcga gggcaagacc attgtgttcc gaaactcgtc attcatcaag    4500
tacaagaatg agaccgtctt ctcttctgtg cacaccaccg gtaaggtatt gatggagctg    4560
ccctccaagg aggtcattga gattgccact gttaactacc aggctggcga gtctcatggc    4620
aatcccgtca ttgattacct ggagcgaaat ggaaccacca ttgagcagcc tgttgagttt    4680
gagaagccca tccctctgtc caaggcagat gatcttctct ccttcaaggc tccttcttcc    4740
aacgagccct acgctggtgt gtccggtgac tacaatccca tccacgtgtc tcgagccttt    4800
gcttcctatg catcccttcc tggaaccatc acccacggta tgtactcttc tgctgctgtt    4860
cgatctctga ttgaggtctg ggctgccgag aacaatgtgt ctcgagttcg agccttctcc    4920
tgtcagttcc agggcatggt tttgcccaac gacgagattg tgactcgact ggagcacgtt    4980
ggcatgatca acggtcgaaa gatcatcaag gttacctcca ccaaccggga gaccgaggct    5040
gttgttctgt ctgctcgaggc tgaggtcgag cagcccatct ccacctttgt ctttactggc    5100
cagggctctc aggagcaggg catgggtatg gacctgtacg cctcttccga ggtggccaag    5160
aaggtctggg acaaggctga cgagcacttc ttgcagaact acggtttctc catcatcaag    5220
atcgttgtgg agaaccccaa ggagctggat attcattttg gaggccccaa gggtaagaag    5280
atccgagaca actatatctc tatgatgttc gagaccattg atgagaagac cggcaacctc    5340
atttccgaga agatcttcaa ggagattgac gagaccaccg actctttcac cttcaagtcc    5400
cccaccggtc tgctttctgc tacccagttc actcagcccg ctctgaccct catggagaag    5460
```

```
gcgtcctttg aggacatgaa ggctaagggt cttgtcccg tggatgcaac ctttgctggt    5520
cactcccttg gtgagtactc cgctcttgct tctcttggtg atgtcatgcc catcgagtct    5580
cttgttgatg tcgtcttcta ccgaggtatg actatgcagg ttgctgttcc ccgagatgcc    5640
cagggtcggt ccaattacgg tatgtgcgct gtcaaccct ctcgaatctc taccaccttc    5700
aacgacgctg ctcttcggtt tgtcgttgac cacatctccg agcagaccaa gtggctgctt    5760
gagattgtca actacaacgt tgagaactct cagtacgtga ctgccggtga cctgcgagct    5820
ctcgacaccc tcaccaatgt gctcaacgtg ctcaaactcg agaagatcaa cattgacaag    5880
ctgctcgagt ctctgcctct ggagaaggtc aaggagcacc tttctgagat cgtcaccgag    5940
gtggccaaga agtccgttgc taagcctcag cccattgagc tggaacgagg ctttgccgtg    6000
atccctctca agggcatctc tgtgcctttc cactcttcgt acctgcgaaa tggtgtcaag    6060
cccttccaaa acttcctggt gaagaaggtg cccaagaacg ctgtcaaacc tgccaacctc    6120
attggcaagt acatccccaa cctcactgcc aagcccttg agatcaccaa ggagtacttt    6180
gaagaggttt acaagctcac cggttccgag aaggtcaaga gcatcatcaa caactgggag    6240
tcttatgagt ccaagcagta a                                               6261
```

<210> SEQ ID NO 14
<211> LENGTH: 2086
<212> TYPE: PRT
<213> ORGANISM: Yarrowia lipolytica
<220> FEATURE:
<221> NAME/KEY: MISC_FEATURE
<223> OTHER INFORMATION: fatty acid synthase subunit beta

<400> SEQUENCE: 14

```
Met Tyr Pro Thr Thr Gly Val Asn Thr Pro Gln Ser Ala Ala Ser Leu
1               5                   10                  15

Arg Pro Leu Val Leu Ser His Gly Gln Thr Glu His Ser Leu Leu Val
            20                  25                  30

Pro Thr Ser Leu Tyr Ile Asn Cys Thr Thr Leu Arg Asp Gln Phe Tyr
        35                  40                  45

Ala Ser Leu Pro Pro Ala Thr Glu Asp Lys Ala Asp Asp Glu Pro
    50                  55                  60

Ser Ser Ser Thr Glu Leu Leu Ala Ala Phe Leu Gly Phe Thr Ala Lys
65                  70                  75                  80

Thr Val Glu Glu Glu Pro Gly Pro Tyr Asp Asp Val Leu Ser Leu Val
                85                  90                  95

Leu Asn Glu Phe Glu Thr Arg Tyr Leu Arg Gly Asn Asp Ile His Ala
            100                 105                 110

Val Ala Ser Ser Leu Leu Gln Asp Glu Asp Val Pro Thr Thr Val Gly
        115                 120                 125

Lys Ile Lys Arg Val Ile Arg Ala Tyr Ala Ala Arg Ile Ala Cys
    130                 135                 140

Asn Arg Pro Ile Lys Ala His Ser Ser Ala Leu Phe Arg Ala Ala Ser
145                 150                 155                 160

Glu Asp Ser Asp Asn Val Ser Leu Tyr Ala Ile Phe Gly Gly Gln Gly
                165                 170                 175

Asn Thr Glu Asp Tyr Phe Glu Glu Leu Arg Glu Ile Tyr Asp Ile Tyr
            180                 185                 190

Gln Gly Leu Val Gly Asp Phe Ile Arg Glu Cys Gly Ala Gln Leu Leu
        195                 200                 205
```

-continued

```
Ala Leu Ser Arg Asp His Ile Ala Ala Glu Lys Ile Tyr Thr Lys Gly
210                 215                 220
Phe Asp Ile Val Lys Trp Leu Glu His Pro Glu Thr Ile Pro Asp Phe
225                 230                 235                 240
Glu Tyr Leu Ile Ser Ala Pro Ile Ser Val Pro Ile Ile Gly Val Ile
            245                 250                 255
Gln Leu Ala His Tyr Ala Val Thr Cys Arg Val Leu Gly Leu Asn Pro
                260                 265                 270
Gly Gln Val Arg Asp Asn Leu Lys Gly Ala Thr Gly His Ser Gln Gly
            275                 280                 285
Leu Ile Thr Ala Ile Ala Ile Ser Ala Ser Asp Ser Trp Asp Glu Phe
290                 295                 300
Tyr Asn Ser Ala Ser Arg Ile Leu Lys Ile Phe Phe Phe Ile Gly Val
305                 310                 315                 320
Arg Val Gln Gln Ala Tyr Pro Ser Thr Phe Leu Pro Pro Ser Thr Leu
                325                 330                 335
Glu Asp Ser Val Lys Gln Gly Glu Gly Lys Pro Thr Pro Met Leu Ser
            340                 345                 350
Ile Arg Asp Leu Ser Leu Asn Gln Val Gln Glu Phe Val Asp Ala Thr
355                 360                 365
Asn Leu His Leu Pro Glu Asp Lys Gln Ile Val Val Ser Leu Ile Asn
370                 375                 380
Gly Pro Arg Asn Val Val Val Thr Gly Pro Pro Gln Ser Leu Tyr Gly
385                 390                 395                 400
Leu Cys Leu Val Leu Arg Lys Gln Lys Ala Glu Thr Gly Leu Asp Gln
                405                 410                 415
Ser Arg Val Pro His Ser Gln Arg Lys Leu Lys Phe Thr His Arg Phe
            420                 425                 430
Leu Pro Ile Thr Ser Pro Phe His Ser Tyr Leu Leu Glu Lys Ser Thr
            435                 440                 445
Asp Leu Ile Ile Asn Asp Leu Glu Ser Ser Gly Val Glu Phe Val Ser
450                 455                 460
Ser Glu Leu Lys Val Pro Val Tyr Asp Thr Phe Asp Gly Ser Val Leu
465                 470                 475                 480
Ser Gln Leu Pro Lys Gly Ile Val Ser Arg Leu Val Asn Leu Ile Thr
                485                 490                 495
His Leu Pro Val Lys Trp Glu Lys Ala Thr Gln Phe Gln Ala Ser His
            500                 505                 510
Ile Val Asp Phe Gly Pro Gly Gly Ala Ser Gly Leu Gly Leu Leu Thr
            515                 520                 525
His Lys Asn Lys Asp Gly Thr Gly Val Arg Thr Ile Leu Ala Gly Val
530                 535                 540
Ile Asp Gln Pro Leu Glu Phe Gly Phe Lys Gln Glu Leu Phe Asp Arg
545                 550                 555                 560
Gln Glu Ser Ser Ile Val Phe Ala Gln Asn Trp Ala Lys Glu Phe Ser
                565                 570                 575
Pro Lys Leu Val Lys Ile Ser Ser Thr Asn Glu Val Tyr Val Asp Thr
            580                 585                 590
Lys Phe Ser Arg Leu Thr Gly Arg Ala Pro Ile Met Val Ala Gly Met
            595                 600                 605
Thr Pro Thr Thr Val Asn Pro Lys Phe Val Ala Ala Thr Met Asn Ser
610                 615                 620
Gly Tyr His Ile Glu Leu Gly Gly Gly Gly Tyr Phe Ala Pro Gly Met
```

-continued

```
            625                 630                 635                 640
        Met Thr Lys Ala Leu Glu His Ile Glu Lys Asn Thr Pro Pro Gly Ser
                        645                 650                 655
        Gly Ile Thr Ile Asn Leu Ile Tyr Val Asn Pro Arg Leu Ile Gln Trp
                        660                 665                 670
        Gly Ile Pro Leu Ile Gln Glu Leu Arg Gln Lys Gly Phe Pro Ile Glu
                        675                 680                 685
        Gly Leu Thr Ile Gly Ala Gly Val Pro Ser Leu Glu Val Ala Asn Glu
                        690                 695                 700
        Trp Ile Gln Asp Leu Gly Val Lys His Ile Ala Phe Lys Pro Gly Ser
        705                 710                 715                 720
        Ile Glu Ala Ile Ser Ser Val Ile Arg Ile Ala Lys Ala Asn Pro Asp
                        725                 730                 735
        Phe Pro Ile Ile Leu Gln Trp Thr Gly Arg Gly Gly Gly His His
                        740                 745                 750
        Ser Phe Glu Asp Phe His Ala Pro Ile Leu Gln Met Tyr Ser Lys Ile
                        755                 760                 765
        Arg Arg Cys Ser Asn Ile Val Leu Ile Ala Gly Ser Gly Phe Gly Ala
        770                 775                 780
        Ser Thr Asp Ser Tyr Pro Tyr Leu Thr Gly Ser Trp Ser Arg Asp Phe
        785                 790                 795                 800
        Asp Tyr Pro Pro Met Pro Phe Asp Gly Ile Leu Val Gly Ser Arg Val
                        805                 810                 815
        Met Val Ala Lys Glu Ala Phe Thr Ser Leu Gly Ala Lys Gln Leu Ile
                        820                 825                 830
        Val Asp Ser Pro Gly Val Glu Asp Ser Glu Trp Glu Lys Thr Tyr Asp
                        835                 840                 845
        Lys Pro Thr Gly Gly Val Ile Thr Val Leu Ser Glu Met Gly Glu Pro
                        850                 855                 860
        Ile His Lys Leu Ala Thr Arg Gly Val Leu Phe Trp His Glu Met Asp
        865                 870                 875                 880
        Lys Thr Val Phe Ser Leu Pro Lys Lys Lys Arg Leu Glu Val Leu Lys
                        885                 890                 895
        Ser Lys Arg Ala Tyr Ile Ile Lys Arg Leu Asn Asp Asp Phe Gln Lys
                        900                 905                 910
        Thr Trp Phe Ala Lys Asn Ala Gln Gly Gln Val Cys Asp Leu Glu Asp
                        915                 920                 925
        Leu Thr Tyr Ala Glu Val Ile Gln Arg Leu Val Asp Leu Met Tyr Val
                        930                 935                 940
        Lys Lys Glu Ser Arg Trp Ile Asp Val Thr Leu Arg Asn Leu Ala Gly
        945                 950                 955                 960
        Thr Phe Ile Arg Arg Val Glu Glu Arg Phe Ser Glu Thr Gly Ala
                        965                 970                 975
        Ser Ser Val Leu Gln Ser Phe Ser Glu Leu Asp Ser Glu Pro Glu Lys
                        980                 985                 990
        Val Val Glu Arg Val Phe Glu Leu Phe Pro Ala Ser Thr Thr Gln Ile
                        995                1000                1005
        Ile Asn Ala Gln Asp Lys Asp His Phe Leu Met Leu Cys Leu Asn
                       1010                1015                1020
        Pro Met Gln Lys Pro Val Pro Phe Ile Pro Val Leu Asp Asp Asn
                       1025                1030                1035
        Phe Glu Phe Phe Phe Lys Lys Asp Ser Leu Trp Gln Cys Glu Asp
                       1040                1045                1050
```

```
Leu Ala Ala Val Val Asp Glu Asp Val Gly Arg Ile Cys Ile Leu
    1055            1060            1065

Gln Gly Pro Val Ala Val Lys His Ser Lys Ile Val Asn Glu Pro
    1070            1075            1080

Val Lys Glu Ile Leu Asp Ser Met His Glu Gly His Ile Lys Gln
    1085            1090            1095

Leu Leu Glu Asp Gly Glu Tyr Ala Gly Asn Met Ala Asn Ile Pro
    1100            1105            1110

Gln Val Glu Cys Phe Gly Gly Lys Pro Ala Gln Asn Phe Gly Asp
    1115            1120            1125

Val Ala Leu Asp Ser Val Met Val Leu Asp Leu Asn Lys Thr
    1130            1135            1140

Val Phe Lys Ile Glu Thr Gly Thr Ser Ala Leu Pro Ser Ala Ala
    1145            1150            1155

Asp Trp Phe Ser Leu Leu Ala Gly Asp Lys Asn Ser Trp Arg Gln
    1160            1165            1170

Val Phe Leu Ser Thr Asp Thr Ile Val Gln Thr Thr Lys Met Ile
    1175            1180            1185

Ser Asn Pro Leu His Arg Leu Leu Glu Pro Ile Ala Gly Leu Gln
    1190            1195            1200

Val Glu Ile Glu His Pro Asp Glu Pro Glu Asn Thr Val Ile Ser
    1205            1210            1215

Ala Phe Glu Pro Ile Asn Gly Lys Val Thr Lys Val Leu Glu Leu
    1220            1225            1230

Arg Lys Gly Ala Gly Asp Val Ile Ser Leu Gln Leu Ile Glu Ala
    1235            1240            1245

Arg Gly Val Asp Arg Val Pro Val Ala Leu Pro Leu Glu Phe Lys
    1250            1255            1260

Tyr Gln Pro Gln Ile Gly Tyr Ala Pro Ile Val Glu Val Met Thr
    1265            1270            1275

Asp Arg Asn Thr Arg Ile Lys Glu Phe Tyr Trp Lys Leu Trp Phe
    1280            1285            1290

Gly Gln Asp Ser Lys Phe Glu Ile Asp Thr Asp Ile Thr Glu Glu
    1295            1300            1305

Ile Ile Gly Asp Asp Val Thr Ile Ser Gly Lys Ala Ile Ala Asp
    1310            1315            1320

Phe Val His Ala Val Gly Asn Lys Gly Glu Ala Phe Val Gly Arg
    1325            1330            1335

Ser Thr Ser Ala Gly Thr Val Phe Ala Pro Met Asp Phe Ala Ile
    1340            1345            1350

Val Leu Gly Trp Lys Ala Ile Ile Lys Ala Ile Phe Pro Arg Ala
    1355            1360            1365

Ile Asp Ala Asp Ile Leu Arg Leu Val His Leu Ser Asn Gly Phe
    1370            1375            1380

Lys Met Met Pro Gly Ala Asp Pro Leu Gln Met Gly Asp Val Val
    1385            1390            1395

Ser Ala Thr Ala Lys Ile Asp Thr Val Lys Asn Ser Ala Thr Gly
    1400            1405            1410

Lys Thr Val Ala Val Arg Gly Leu Leu Thr Arg Asp Gly Lys Pro
    1415            1420            1425

Val Met Glu Val Val Ser Glu Phe Phe Tyr Arg Gly Glu Phe Ser
    1430            1435            1440
```

```
Asp Phe Gln Asn Thr Phe Glu Arg Arg Glu Glu Val Pro Met Gln
1445                1450                1455

Leu Thr Leu Lys Asp Ala Lys Ala Val Ala Ile Leu Cys Ser Lys
1460                1465                1470

Glu Trp Phe Glu Tyr Asn Gly Asp Asp Thr Lys Asp Leu Glu Gly
1475                1480                1485

Lys Thr Ile Val Phe Arg Asn Ser Ser Phe Ile Lys Tyr Lys Asn
1490                1495                1500

Glu Thr Val Phe Ser Ser Val His Thr Thr Gly Lys Val Leu Met
1505                1510                1515

Glu Leu Pro Ser Lys Glu Val Ile Glu Ile Ala Thr Val Asn Tyr
1520                1525                1530

Gln Ala Gly Glu Ser His Gly Asn Pro Val Ile Asp Tyr Leu Glu
1535                1540                1545

Arg Asn Gly Thr Thr Ile Glu Gln Pro Val Glu Phe Glu Lys Pro
1550                1555                1560

Ile Pro Leu Ser Lys Ala Asp Asp Leu Leu Ser Phe Lys Ala Pro
1565                1570                1575

Ser Ser Asn Glu Pro Tyr Ala Gly Val Ser Gly Asp Tyr Asn Pro
1580                1585                1590

Ile His Val Ser Arg Ala Phe Ala Ser Tyr Ala Ser Leu Pro Gly
1595                1600                1605

Thr Ile Thr His Gly Met Tyr Ser Ser Ala Ala Val Arg Ser Leu
1610                1615                1620

Ile Glu Val Trp Ala Ala Glu Asn Asn Val Ser Arg Val Arg Ala
1625                1630                1635

Phe Ser Cys Gln Phe Gln Gly Met Val Leu Pro Asn Asp Glu Ile
1640                1645                1650

Val Thr Arg Leu Glu His Val Gly Met Ile Asn Gly Arg Lys Ile
1655                1660                1665

Ile Lys Val Thr Ser Thr Asn Arg Glu Thr Glu Ala Val Val Leu
1670                1675                1680

Ser Gly Glu Ala Glu Val Glu Gln Pro Ile Ser Thr Phe Val Phe
1685                1690                1695

Thr Gly Gln Gly Ser Gln Glu Gln Gly Met Gly Met Asp Leu Tyr
1700                1705                1710

Ala Ser Ser Glu Val Ala Lys Lys Val Trp Asp Lys Ala Asp Glu
1715                1720                1725

His Phe Leu Gln Asn Tyr Gly Phe Ser Ile Ile Lys Ile Val Val
1730                1735                1740

Glu Asn Pro Lys Glu Leu Asp Ile His Phe Gly Gly Pro Lys Gly
1745                1750                1755

Lys Lys Ile Arg Asp Asn Tyr Ile Ser Met Met Phe Glu Thr Ile
1760                1765                1770

Asp Glu Lys Thr Gly Asn Leu Ile Ser Glu Lys Ile Phe Lys Glu
1775                1780                1785

Ile Asp Glu Thr Thr Asp Ser Phe Thr Phe Lys Ser Pro Thr Gly
1790                1795                1800

Leu Leu Ser Ala Thr Gln Phe Thr Gln Pro Ala Leu Thr Leu Met
1805                1810                1815

Glu Lys Ala Ser Phe Glu Asp Met Lys Ala Lys Gly Leu Val Pro
1820                1825                1830

Val Asp Ala Thr Phe Ala Gly His Ser Leu Gly Glu Tyr Ser Ala
```

| | | | | | | | | | |
|---|---|---|---|---|---|---|---|---|---|
| | | 1835 | | | 1840 | | | 1845 | |
| Leu | Ala | Ser | Leu | Gly | Asp | Val | Met | Pro | Ile | Glu | Ser | Leu | Val | Asp |
| | | 1850 | | | | 1855 | | | 1860 | |
| Val | Val | Phe | Tyr | Arg | Gly | Met | Thr | Met | Gln | Val | Ala | Val | Pro | Arg |
| | | 1865 | | | | 1870 | | | 1875 | |
| Asp | Ala | Gln | Gly | Arg | Ser | Asn | Tyr | Gly | Met | Cys | Ala | Val | Asn | Pro |
| | | 1880 | | | | 1885 | | | 1890 | |
| Ser | Arg | Ile | Ser | Thr | Thr | Phe | Asn | Asp | Ala | Ala | Leu | Arg | Phe | Val |
| | | 1895 | | | | 1900 | | | 1905 | |
| Val | Asp | His | Ile | Ser | Glu | Gln | Thr | Lys | Trp | Leu | Leu | Glu | Ile | Val |
| | | 1910 | | | | 1915 | | | 1920 | |
| Asn | Tyr | Asn | Val | Glu | Asn | Ser | Gln | Tyr | Val | Thr | Ala | Gly | Asp | Leu |
| | | 1925 | | | | 1930 | | | 1935 | |
| Arg | Ala | Leu | Asp | Thr | Leu | Thr | Asn | Val | Leu | Asn | Val | Leu | Lys | Leu |
| | | 1940 | | | | 1945 | | | 1950 | |
| Glu | Lys | Ile | Asn | Ile | Asp | Lys | Leu | Leu | Glu | Ser | Leu | Pro | Leu | Glu |
| | | 1955 | | | | 1960 | | | 1965 | |
| Lys | Val | Lys | Glu | His | Leu | Ser | Glu | Ile | Val | Thr | Glu | Val | Ala | Lys |
| | | 1970 | | | | 1975 | | | 1980 | |
| Lys | Ser | Val | Ala | Lys | Pro | Gln | Pro | Ile | Glu | Leu | Glu | Arg | Gly | Phe |
| | | 1985 | | | | 1990 | | | 1995 | |
| Ala | Val | Ile | Pro | Leu | Lys | Gly | Ile | Ser | Val | Pro | Phe | His | Ser | Ser |
| | | 2000 | | | | 2005 | | | 2010 | |
| Tyr | Leu | Arg | Asn | Gly | Val | Lys | Pro | Phe | Gln | Asn | Phe | Leu | Val | Lys |
| | | 2015 | | | | 2020 | | | 2025 | |
| Lys | Val | Pro | Lys | Asn | Ala | Val | Lys | Pro | Ala | Asn | Leu | Ile | Gly | Lys |
| | | 2030 | | | | 2035 | | | 2040 | |
| Tyr | Ile | Pro | Asn | Leu | Thr | Ala | Lys | Pro | Phe | Glu | Ile | Thr | Lys | Glu |
| | | 2045 | | | | 2050 | | | 2055 | |
| Tyr | Phe | Glu | Glu | Val | Tyr | Lys | Leu | Thr | Gly | Ser | Glu | Lys | Val | Lys |
| | | 2060 | | | | 2065 | | | 2070 | |
| Ser | Ile | Ile | Asn | Asn | Trp | Glu | Ser | Tyr | Glu | Ser | Lys | Gln | | |
| | | 2075 | | | | 2080 | | | 2085 | |

<210> SEQ ID NO 15
<211> LENGTH: 1635
<212> TYPE: DNA
<213> ORGANISM: Yarrowia lipolytica
<220> FEATURE:
<221> NAME/KEY: misc_feature
<223> OTHER INFORMATION: Acetyl-CoA carboxylase transferase subunit beta

<400> SEQUENCE: 15

```
atgcccgagt accctcgagg ccgatctttc atcgtggtgg ccaacgatat caccttccag    60
attggttcgt ttggccctgc tgaggaccag ttcttcttca aggtgacgga gctggctcga   120
aagctcggta ttcctcgaat ctatctgtct gccaactctg gtgctcgaat cggcattgct   180
gacgagctcg ttggcaagta caaggttgcg tggaacgacg agactgaccc ctccaagggc   240
ttcaagtacc tttacttcac ccctgagtct cttgccaccc tcaagcccga cactgttgtc   300
accactgaga ttgaggagga gggtcccaac ggcgtggaga gcgtcatgt gatcgactac   360 attgtcggag agaaggacgg tctcggagtc gagtgtctgc ggggctctgg tctcattgca   420
ggcgccactt tcgagcccta caaggatatc ttcactctca ctcttgtcac ctgtcgatcc   480
gttggtatcg gtgcttacct tgttcgtctt ggtcaacgag ccatccagat tgagggccag   540
```

```
cccatcattc tcactggtgc ccccgccatc aacaagctgc ttggtcgaga ggtctactct    600
tccaacttgc agcttggtgg tactcagatc atgtacaaca acggtgtgtc tcatctgact    660
gcccgagatg atctcaacgg tgtccacaag atcatgcagt ggctgtcata catccctgct    720
tctcgaggtc ttccagtgcc tgttctccct cacaagaccg atgtgtggga tcgagacgtg    780
acgttccagc ctgtccgagg cgagcagtac gatgttagat ggcttatttc tggccgaact    840
ctcgaggatg tgctttcga gtctggtctc tttgacaagg actcttcca ggagactctg    900 tctggctggg ccaagggtgt tgttgttggt cgagctcgtc ttggcggcat tcccttcggt    960
gtcattggtg tcgagactgc gaccgtcgac aatactaccc ctgccgatcc cgccaacccg   1020
gactctattg agatgagcac ctctgaagcc ggccaggttt ggtaccccaa ctcggccttc   1080
aagacctctc aggccatcaa cgacttcaac catggtgagg cgcttcctct catgattctt   1140
gctaactggc gaggctttc tggtggtcag cgagacatgt acaatgaggt tctcaagtac   1200
ggatctttca ttgttgatgc tctggttgac tacaagcagc catcatggt gtacatccct   1260 cccaccggtg agctgcgagg tggttcttgg gttgtggttg accccaccat caactcggac   1320
atgatggaga tgtacgctga cgtcgagtct cgaggtggtg tgctggagcc cgagggaatg   1380
gtcggtatca agtaccgacg agacaagcta ctggacacca tggctcgtct ggatcccgag   1440
tactcctctc tcaagaagca gcttgaggag tctcccgatt ctgaggagct caaggtcaag   1500
ctcagcgtgc gagagaagtc tctcatgccc atctaccagc agatctccgt gcagtttgcc   1560
gacttgcatg accgagctgg ccgaatggag gccaagggtg tcattcgtga ggctcttgtg   1620
tggaaggatg cttga                                                    1635
```

<210> SEQ ID NO 16
<211> LENGTH: 544
<212> TYPE: PRT
<213> ORGANISM: Yarrowia lipolytica
<220> FEATURE:
<221> NAME/KEY: MISC_FEATURE
<223> OTHER INFORMATION: Acetyl-CoA carboxylase transferase subunit beta

<400> SEQUENCE: 16

```
Met Pro Glu Tyr Pro Arg Gly Arg Ser Phe Ile Val Val Ala Asn Asp
1               5                   10                  15

Ile Thr Phe Gln Ile Gly Ser Phe Gly Pro Ala Glu Asp Gln Phe Phe
            20                  25                  30

Phe Lys Val Thr Glu Leu Ala Arg Lys Leu Gly Ile Pro Arg Ile Tyr
        35                  40                  45

Leu Ser Ala Asn Ser Gly Ala Arg Ile Gly Ile Ala Asp Glu Leu Val
    50                  55                  60

Gly Lys Tyr Lys Val Ala Trp Asn Asp Glu Thr Asp Pro Ser Lys Gly
65                  70                  75                  80

Phe Lys Tyr Leu Tyr Phe Thr Pro Glu Ser Leu Ala Thr Leu Lys Pro
                85                  90                  95

Asp Thr Val Val Thr Thr Glu Ile Glu Glu Gly Pro Asn Gly Val
            100                 105                 110

Glu Lys Arg His Val Ile Asp Tyr Ile Val Gly Glu Lys Asp Gly Leu
        115                 120                 125

Gly Val Glu Cys Leu Arg Gly Ser Gly Leu Ile Ala Gly Ala Thr Ser
    130                 135                 140

Arg Ala Tyr Lys Asp Ile Phe Thr Leu Thr Leu Val Thr Cys Arg Ser
145                 150                 155                 160
```

Val Gly Ile Gly Ala Tyr Leu Val Arg Leu Gly Gln Arg Ala Ile Gln
                        165                 170                 175

Ile Glu Gly Gln Pro Ile Ile Leu Thr Gly Ala Pro Ala Ile Asn Lys
            180                 185                 190

Leu Leu Gly Arg Glu Val Tyr Ser Ser Asn Leu Gln Leu Gly Gly Thr
        195                 200                 205

Gln Ile Met Tyr Asn Asn Gly Val Ser His Leu Thr Ala Arg Asp Asp
    210                 215                 220

Leu Asn Gly Val His Lys Ile Met Gln Trp Leu Ser Tyr Ile Pro Ala
225                 230                 235                 240

Ser Arg Gly Leu Pro Val Pro Val Leu Pro His Lys Thr Asp Val Trp
                245                 250                 255

Asp Arg Asp Val Thr Phe Gln Pro Val Arg Gly Glu Gln Tyr Asp Val
            260                 265                 270

Arg Trp Leu Ile Ser Gly Arg Thr Leu Glu Asp Gly Ala Phe Glu Ser
        275                 280                 285

Gly Leu Phe Asp Lys Asp Ser Phe Gln Glu Thr Leu Ser Gly Trp Ala
    290                 295                 300

Lys Gly Val Val Gly Arg Ala Arg Leu Gly Gly Ile Pro Phe Gly
305                 310                 315                 320

Val Ile Gly Val Glu Thr Ala Thr Val Asp Asn Thr Thr Pro Ala Asp
                325                 330                 335

Pro Ala Asn Pro Asp Ser Ile Glu Met Ser Thr Ser Glu Ala Gly Gln
            340                 345                 350

Val Trp Tyr Pro Asn Ser Ala Phe Lys Thr Ser Gln Ala Ile Asn Asp
        355                 360                 365

Phe Asn His Gly Glu Ala Leu Pro Leu Met Ile Leu Ala Asn Trp Arg
    370                 375                 380

Gly Phe Ser Gly Gly Gln Arg Asp Met Tyr Asn Glu Val Leu Lys Tyr
385                 390                 395                 400

Gly Ser Phe Ile Val Asp Ala Leu Val Asp Tyr Lys Gln Pro Ile Met
                405                 410                 415

Val Tyr Ile Pro Pro Thr Gly Glu Leu Arg Gly Gly Ser Trp Val Val
            420                 425                 430

Val Asp Pro Thr Ile Asn Ser Asp Met Met Glu Met Tyr Ala Asp Val
        435                 440                 445

Glu Ser Arg Gly Gly Val Leu Glu Pro Glu Gly Met Val Gly Ile Lys
    450                 455                 460

Tyr Arg Arg Asp Lys Leu Leu Asp Thr Met Ala Arg Leu Asp Pro Glu
465                 470                 475                 480

Tyr Ser Ser Leu Lys Lys Gln Leu Glu Glu Ser Pro Asp Ser Glu Glu
                485                 490                 495

Leu Lys Val Lys Leu Ser Val Arg Glu Lys Ser Leu Met Pro Ile Tyr
            500                 505                 510

Gln Gln Ile Ser Val Gln Phe Ala Asp Leu His Asp Arg Ala Gly Arg
        515                 520                 525

Met Glu Ala Lys Gly Val Ile Arg Glu Ala Leu Val Trp Lys Asp Ala
    530                 535                 540

<210> SEQ ID NO 17
<211> LENGTH: 792
<212> TYPE: DNA
<213> ORGANISM: Yarrowia lipolytica
<220> FEATURE:
<221> NAME/KEY: misc_feature
<223> OTHER INFORMATION: fatty acid synthase subunit alpha-active site 1

<400> SEQUENCE: 17

```
atggatggtc tcactttcca gggcaagact gctctgatca ccggtgctgg tgctggctcc      60
attggtgcct caatcctcca gggtctcatt tccggaggct gcaaagtcat tgtcacaacc     120
tctcgatact cccgaaaggt gaccgagtac taccagtccc tctacaccaa gttcggtgct     180
aagggttcca ctctgattgt tgtccccttc aaccaaggct ccaagaagga cgtggacgag     240
ctggtgtcgt tcatctacaa cgaccccaag aacggcggtc ttggctggga tctggacttt     300
gttgttccct tgctgctct gcccgagaac ggtattgagc tggagcacat tgactcaaag     360
tccgagcttg cccatcgaat catgctcacc aacctcctgc gtctgcttgg taacgtcaag     420
aagcagaaag tggcccattc ctacgagact cgacccgccc aggtcatgct gcccctgtcg     480
cccaaccatg gcaacttcgg ctccgatggt ctgtactccg agtccaagat ctctctcgag     540
actctgttca accggtggca caccgagtcc tggggctctt atctcaccat tgttggtgtg     600
gtgattggct ggacccgagg taccggtctg atgagcgcca acaacatcac cgccgagggt     660
ctggagcagc tcggcgtccg aaccttctcc cagactgaga tggccttttc catcatgggt     720
ctcatgacca aggacattgt gcgactggcc cagaactccc ccgtgtgggc cgatctcaac     780
ggtggcttct ga                                                        792
```

<210> SEQ ID NO 18
<211> LENGTH: 263
<212> TYPE: PRT
<213> ORGANISM: Yarrowia lipolytica
<220> FEATURE:
<221> NAME/KEY: MISC_FEATURE
<223> OTHER INFORMATION: fatty acid synthase subunit alpha-active site 1

<400> SEQUENCE: 18

```
Met Asp Gly Leu Thr Phe Gln Gly Lys Thr Ala Leu Ile Thr Gly Ala
1               5                   10                  15

Gly Ala Gly Ser Ile Gly Ala Ser Ile Leu Gln Gly Leu Ile Ser Gly
            20                  25                  30

Gly Cys Lys Val Ile Val Thr Thr Ser Arg Tyr Ser Arg Lys Val Thr
        35                  40                  45

Glu Tyr Tyr Gln Ser Leu Tyr Thr Lys Phe Gly Ala Lys Gly Ser Thr
    50                  55                  60

Leu Ile Val Val Pro Phe Asn Gln Gly Ser Lys Lys Asp Val Asp Glu
65                  70                  75                  80

Leu Val Ser Phe Ile Tyr Asn Asp Pro Lys Asn Gly Gly Leu Gly Trp
                85                  90                  95

Asp Leu Asp Phe Val Val Pro Phe Ala Ala Leu Pro Glu Asn Gly Ile
            100                 105                 110

Glu Leu Glu His Ile Asp Ser Lys Ser Glu Leu Ala His Arg Ile Met
        115                 120                 125

Leu Thr Asn Leu Leu Arg Leu Leu Gly Asn Val Lys Lys Gln Lys Val
    130                 135                 140

Ala His Ser Tyr Glu Thr Arg Pro Ala Gln Val Met Leu Pro Leu Ser
145                 150                 155                 160

Pro Asn His Gly Asn Phe Gly Ser Asp Gly Leu Tyr Ser Glu Ser Lys
                165                 170                 175

Ile Ser Leu Glu Thr Leu Phe Asn Arg Trp His Thr Glu Ser Trp Gly
            180                 185                 190
```

```
Ser Tyr Leu Thr Ile Val Gly Val Ile Gly Trp Thr Arg Gly Thr
            195                 200                 205

Gly Leu Met Ser Ala Asn Asn Ile Thr Ala Glu Gly Leu Glu Gln Leu
        210                 215                 220

Gly Val Arg Thr Phe Ser Gln Thr Glu Met Ala Phe Ser Ile Met Gly
225                 230                 235                 240

Leu Met Thr Lys Asp Ile Val Arg Leu Ala Gln Asn Ser Pro Val Trp
                245                 250                 255

Ala Asp Leu Asn Gly Gly Phe
            260
```

```
<210> SEQ ID NO 19
<211> LENGTH: 903
<212> TYPE: DNA
<213> ORGANISM: Artificial sequence
<220> FEATURE:
<223> OTHER INFORMATION: Synthetic polynucleotide

<400> SEQUENCE: 19
atgctcgagt ggaagcctaa gcctaagctc cctcagctcc tggacgatca ttttggtctg      60
cacggtctgg ttttccgacg aacttttgcc atccgatcct acgaggttgg acccgaccga     120
tctacctcga ttctggctgt catgaaccac atgcaggaag ccactctgaa ccatgctaag     180
tccgttggca tcctcggcga cggttttgga accactctgg agatgtctaa gcagatctcc     240
atgtgggtcg tgcgacgaac ccacgttgcc gtcgagcgat accctacctg gggtgacact     300
gtggaggttg agtgctggat tggcgcttct ggtaacaacg gaatgcgacg agactttctg     360
gtgcgagatt gcaagaccgg agagatcctc accgatgta cttccctgtc tgtcctcatg     420
aacacccgaa ctcgacgact ctccaccatt cccgacgagg tgcgaggcga gatcggtcct     480
gccttcattg ataacgtcgc tgtgaaggac gatgagatca gaagctgca gaagctcaac     540
gactctaccg ccgattacat tcagggcggt ctgactcccc gatggaacga cctcgatgtg     600
aaccagcacg ttaacaacct gaagtacgtt gcttgggtct tcgagaccgt ccctgactcg     660
atctttgagt cccaccatat ttcctctttc acccctcgagt accgacgaga gtgcactcga     720
gactctgtcc tgcgatcgct caccactgtg tcggaggct cgtctgaggc tggactggtg     780
tgtgaccatc tgctccagct ggagggtgga tctgaggttc tccgagctcg aaccgagtgg     840
cgacccaagc tgaccgattc tttccgaggc atctctgtga ttcccgctga gccccgagtt     900
tag                                                                   903
```

```
<210> SEQ ID NO 20
<211> LENGTH: 300
<212> TYPE: PRT
<213> ORGANISM: Umbellularia californica
<220> FEATURE:
<221> NAME/KEY: MISC_FEATURE
<223> OTHER INFORMATION: lauroyl ACP- thioesterase

<400> SEQUENCE: 20

Met Leu Glu Trp Lys Pro Lys Pro Lys Leu Pro Gln Leu Leu Asp Asp
1               5                   10                  15

His Phe Gly Leu His Gly Leu Val Phe Arg Arg Thr Phe Ala Ile Arg
            20                  25                  30

Ser Tyr Glu Val Gly Pro Asp Arg Ser Thr Ser Ile Leu Ala Val Met
        35                  40                  45

Asn His Met Gln Glu Ala Thr Leu Asn His Ala Lys Ser Val Gly Ile
    50                  55                  60
```

```
Leu Gly Asp Gly Phe Gly Thr Thr Leu Glu Met Ser Lys Arg Asp Leu
 65                  70                  75                  80

Met Trp Val Val Arg Thr His Val Ala Val Glu Arg Tyr Pro Thr
             85                  90                  95

Trp Gly Asp Thr Val Glu Val Cys Trp Ile Gly Ala Ser Gly Asn
            100                 105                 110

Asn Gly Met Arg Arg Asp Phe Leu Val Arg Asp Cys Lys Thr Gly Glu
            115                 120                 125

Ile Leu Thr Arg Cys Thr Ser Leu Ser Val Leu Met Asn Thr Arg Thr
130                 135                 140

Arg Arg Leu Ser Thr Ile Pro Asp Glu Val Arg Gly Glu Ile Gly Pro
145                 150                 155                 160

Ala Phe Ile Asp Asn Val Ala Val Lys Asp Asp Glu Ile Lys Lys Leu
                165                 170                 175

Gln Lys Leu Asn Asp Ser Thr Ala Asp Tyr Ile Gln Gly Gly Leu Thr
            180                 185                 190

Pro Arg Trp Asn Asp Leu Asp Val Asn Gln His Val Asn Asn Leu Lys
        195                 200                 205

Tyr Val Ala Trp Val Phe Glu Thr Val Pro Asp Ser Ile Phe Glu Ser
210                 215                 220

His His Ile Ser Ser Phe Thr Leu Glu Tyr Arg Arg Glu Cys Thr Arg
225                 230                 235                 240

Asp Ser Val Leu Arg Ser Leu Thr Thr Val Ser Gly Ser Ser Glu
                245                 250                 255

Ala Gly Leu Val Cys Asp His Leu Leu Gln Leu Glu Gly Ser Glu
            260                 265                 270

Val Leu Arg Ala Arg Thr Glu Trp Arg Pro Lys Leu Thr Asp Ser Phe
275                 280                 285

Arg Gly Ile Ser Val Ile Pro Ala Glu Pro Arg Val
        290                 295                 300

<210> SEQ ID NO 21
<211> LENGTH: 831
<212> TYPE: DNA
<213> ORGANISM: Artificial sequence
<220> FEATURE:
<223> OTHER INFORMATION: Synthetic polynucleotide

<400> SEQUENCE: 21
ggcctggtgt atcgtcagaa tttcagtatt cgctcctacg aaatcggtgt ggataaacgt      60
gcatcggttg aagctctgat gaaccatttt caagaaacca gcctgaatca ctgcaaatgt     120
attggcctga tgcatggcgg tttcggttgc accccggaaa tgacgcgtcg caatctgatc     180
tgggtggttg ccaaaatgct ggtgcacgtt gaacgctatc cgtggtgggg cgatgtcgtg     240
cagattaaca cctggatctc ctcatcgggt aaaaatggca tgggtcgtga ctggcatgtg     300
cacgattgtc aaaccggcct gccgattatg cgcggcacgt ctgtctgggt gatgatggat     360
aaacacaccc gtcgcctgag taaactgccg gaagaagttc gtgccgaaat cacgccgttt     420
ttctcggaac gtgatgcagt gctggatgac aacggccgca aactgccgaa atttgatgac     480
gattcagcag ctcatgttcg tcgcggtctg accccgcgct ggcatgactt cgatgtcaat     540
cagcacgtga acaatgttaa atacgtcggc tggatcctgg aatccgttcc ggtctggatg     600
ctggacggtt atgaagttgc gaccatgtca ctggaatacc gtcgcgaatg ccgtatggat     660
tcagttgtcc agtcgctgac ggcagtcagc tctgaccacg cggatggtag cccgattgtg     720
```
tgtcagcatc tgctgcgcct ggaagatggc accgaaatcg tgcgtggtca aacggaatgg    780
cgcccggcaa ttgaaggtcg cgctcatcac caccatcatc accatcacta a             831

<210> SEQ ID NO 22
<211> LENGTH: 276
<212> TYPE: PRT
<213> ORGANISM: Artificial sequence
<220> FEATURE:
<223> OTHER INFORMATION: Synthetic polypeptide

<400> SEQUENCE: 22

Gly Leu Val Tyr Arg Gln Asn Phe Ser Ile Arg Ser Tyr Glu Ile Gly
1               5                   10                  15

Val Asp Lys Arg Ala Ser Val Glu Ala Leu Met Asn His Phe Gln Glu
            20                  25                  30

Thr Ser Leu Asn His Cys Lys Cys Ile Gly Leu Met His Gly Gly Phe
        35                  40                  45

Gly Cys Thr Pro Glu Met Thr Arg Arg Asn Leu Ile Trp Val Val Ala
    50                  55                  60

Lys Met Leu Val His Val Glu Arg Tyr Pro Trp Trp Gly Asp Val Val
65                  70                  75                  80

Gln Ile Asn Thr Trp Ile Ser Ser Gly Lys Asn Gly Met Gly Arg
                85                  90                  95

Asp Trp His Val His Asp Cys Gln Thr Gly Leu Pro Ile Met Arg Gly
            100                 105                 110

Thr Ser Val Trp Val Met Met Asp Lys His Thr Arg Arg Leu Ser Lys
        115                 120                 125

Leu Pro Glu Glu Val Arg Ala Glu Ile Thr Pro Phe Phe Ser Glu Arg
    130                 135                 140

Asp Ala Val Leu Asp Asp Asn Gly Arg Lys Leu Pro Lys Phe Asp Asp
145                 150                 155                 160

Asp Ser Ala Ala His Val Arg Arg Gly Leu Thr Pro Arg Trp His Asp
                165                 170                 175

Phe Asp Val Asn Gln His Val Asn Asn Val Lys Tyr Val Gly Trp Ile
            180                 185                 190

Leu Glu Ser Val Pro Val Trp Met Leu Asp Gly Tyr Glu Val Ala Thr
        195                 200                 205

Met Ser Leu Glu Tyr Arg Arg Glu Cys Arg Met Asp Ser Val Val Gln
    210                 215                 220

Ser Leu Thr Ala Val Ser Ser Asp His Ala Asp Gly Ser Pro Ile Val
225                 230                 235                 240

Cys Gln His Leu Leu Arg Leu Glu Asp Gly Thr Glu Ile Val Arg Gly
                245                 250                 255

Gln Thr Glu Trp Arg Pro Ala Ile Glu Gly Arg Ala His His His
            260                 265                 270

His His His His
        275

<210> SEQ ID NO 23
<211> LENGTH: 1245
<212> TYPE: DNA
<213> ORGANISM: Artificial sequence
<220> FEATURE:
<223> OTHER INFORMATION: Synthetic polynucleotide

<400> SEQUENCE: 23

-continued

| | |
|---|---|
| atggttgctt cggttgctgc ttcttcttct ttcttccctg ttccttcgtc ttcttcttcc | 60 |
| gcttctgcta aggcttctcg aggcatcccc gatggcctgg acgtccgagg tatcgtggcc | 120 |
| aagcctgctt cctcttcggg ttggatgcag gccaaggctt ctgcccgagc tatccccaag | 180 |
| attgacgata ccaaggtcgg actgcgaact gatgttgagg aagacgccgc ttccaccgcc | 240 |
| cgacgaactt cttacaacca gctccctgac tggtcgatgc tgctcgccgc tatccgaacc | 300 |
| attttctccg ccgctgagaa gcagtggact ctgctcgact ctaagaagcg aggcgccgat | 360 |
| gctgttgccg acgcttccgg agttggcaag atggtcaaga acggcctggt ctaccgacag | 420 |
| aacttctcga tccgatccta cgagattggt gtggacaagc gagcctcggt ggaggctctc | 480 |
| atgaaccact tccaggagac ctccctgaac cattgcaagt gtatcggcct catgcacggc | 540 |
| ggttttggtt gcacccccga gatgactcga cgaaacctga tttgggtcgt ggccaagatg | 600 |
| ctcgtccacg tggagcgata cccttggtgg ggagacgttg tccagatcaa cacctggatt | 660 |
| tcctcttcgg gcaagaacgg tatgggacga gattggcacg tgcatgactg tcagaccgga | 720 |
| ctgcccatca tgcgaggcac ttctgtttgg gtcatgatgg acaagcatac ccgacgactg | 780 |
| tcgaagctcc ccgaggaagt ccgagccgag attactcctt tcttttctga gcgagacgct | 840 |
| gtgctggacg ataacggacg aaagctcccc aagttcgacg atgactctgc tgctcacgtg | 900 |
| cgacgaggac tcacccctcg atggcacgat tttgacgtta accagcatgt caacaacgtg | 960 |
| aagtacgttg gttggattct ggagtctgtg cccgttggta tgctcgatgg atacgaggtg | 1020 |
| gccaccatgt ccctggagta ccgacgagag tgccgaatgg actctgtggt tcagtcgctc | 1080 |
| accgccgttt cctctgatca tgctgacggt tctcctatcg tctgtcagca cctgctccga | 1140 |
| ctggaggacg gtaccgagat tgtccgagga cagactgagt ggcgacctaa gcagcaggcc | 1200 |
| cgagatctgg gaaacatggg tctccaccct accgagtcca agtaa | 1245 |

<210> SEQ ID NO 24
<211> LENGTH: 414
<212> TYPE: PRT
<213> ORGANISM: Cocos nucifera
<220> FEATURE:
<221> NAME/KEY: MISC_FEATURE
<223> OTHER INFORMATION: lauroyl ACP- thioesterase

<400> SEQUENCE: 24

Met Val Ala Ser Val Ala Ala Ser Ser Phe Phe Pro Val Pro Ser
1               5                   10                  15

Ser Ser Ser Ala Ser Ala Lys Ala Ser Arg Gly Ile Pro Asp Gly
            20                  25                  30

Leu Asp Val Arg Gly Ile Val Ala Lys Pro Ala Ser Ser Gly Trp
        35                  40                  45

Met Gln Ala Lys Ala Ser Ala Arg Ala Ile Pro Lys Ile Asp Asp Thr
    50                  55                  60

Lys Val Gly Leu Arg Thr Asp Val Glu Glu Asp Ala Ala Ser Thr Ala
65                  70                  75                  80

Arg Arg Thr Ser Tyr Asn Gln Leu Pro Asp Trp Ser Met Leu Leu Ala
                85                  90                  95

Ala Ile Arg Thr Ile Phe Ser Ala Ala Glu Lys Gln Trp Thr Leu Leu
            100                 105                 110

Asp Ser Lys Lys Arg Gly Ala Asp Ala Val Ala Asp Ala Ser Gly Val
        115                 120                 125

Gly Lys Met Val Lys Asn Gly Leu Val Tyr Arg Gln Asn Phe Ser Ile
    130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
            165                 170                 175

Leu Met His Gly Gly Phe Gly Cys Thr Pro Glu Met Thr Arg Arg Asn
        180                 185                 190

Leu Ile Trp Val Val Ala Lys Met Leu Val His Val Glu Arg Tyr Pro
    195                 200                 205

Trp Trp Gly Asp Val Val Gln Ile Asn Thr Trp Ile Ser Ser Ser Gly
210                 215                 220

Lys Asn Gly Met Gly Arg Asp Trp His Val His Asp Cys Gln Thr Gly
225                 230                 235                 240

Leu Pro Ile Met Arg Gly Thr Ser Val Trp Val Met Met Asp Lys His
            245                 250                 255

Thr Arg Arg Leu Ser Lys Leu Pro Glu Glu Val Arg Ala Glu Ile Thr
        260                 265                 270

Pro Phe Phe Ser Glu Arg Asp Ala Val Leu Asp Asp Asn Gly Arg Lys
    275                 280                 285

Leu Pro Lys Phe Asp Asp Ser Ala Ala His Val Arg Arg Gly Leu
290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
            325                 330                 335

Gly Tyr Glu Val Ala Thr Met Ser Leu Glu Tyr Arg Arg Glu Cys Arg
        340                 345                 350

Met Asp Ser Val Val Gln Ser Leu Thr Ala Val Ser Ser Asp His Ala
    355                 360                 365

Asp Gly Ser Pro Ile Val Cys Gln His Leu Leu Arg Leu Glu Asp Gly
370                 375                 380

Thr Glu Ile Val Arg Gly Gln Thr Glu Trp Arg Pro Lys Gln Gln Ala
385                 390                 395                 400

Arg Asp Leu Gly Asn Met Gly Leu His Pro Thr Glu Ser Lys
            405                 410

<210> SEQ ID NO 25
<211> LENGTH: 894
<212> TYPE: DNA
<213> ORGANISM: Artificial sequence
<220> FEATURE:
<223> OTHER INFORMATION: Synthetic polynucleotide

<400> SEQUENCE: 25
catatgcatt ttggtctgca tggtctggtt tttcgccgca cctttgctat tcgtagttat     60
gaagttggcc cggaccgctc aacctcgatt ctggcggtta tgaaccacat gcaggaagcg    120
accctgaatc acgccaaaag cgtcggcatc ctgggcgatg gtttcggcac acgctggaa    180 atgtctaaac gtgacctgat gtgggtggtt cgtcgcaccc atgtcgcagt ggaacgctat    240
ccgacctggg gcgatacggt tgaagtcgaa tgctggattg tgctagtgg caacaatggt    300 atgcgtcgcg atttcctggt gcgtgactgc aaaaccggtg aaatcctgac ccgctgtacg    360
tcactgtcgg tgctgatgaa cacccgtacg cgtcgcctgt ctacgattcc ggatgaagtt    420
cgcggcgaaa tcggtccggc gtttattgac aacgtggccg ttaaagatga cgaaatcaaa    480
aaactgcaga aactgaacga tagcaccgca gactatattc aaggcggtct gacgccgcgt    540

```
tggaacgatc tggacgttaa tcagcatgtc aacaatctga aatacgtcgc gtgggtgttt      600
gaaaccgtgc cggatagcat cttcgaatct catcacatta gctcttttac cctggaatac      660
cgtcgcgaat gcacgcgtga tagtgtgctg cgctccctga ccaccgttag tggcggtagt      720
tccgaagcgg gtctggtctg tgaccacctg ctgcaactgg aaggtggttc cgaagtgctg      780
cgtgcacgta ccgaatggcg tccgaaactg acggattcat ttcgcggcat ttcggttatc      840
ccggcaattg aaggtcgcgc tcatcaccac catcatcacc atcaccatca ctaa            894
```

<210> SEQ ID NO 26
<211> LENGTH: 297
<212> TYPE: PRT
<213> ORGANISM: Artificial sequence
<220> FEATURE:
<223> OTHER INFORMATION: Synthetic polypeptide

<400> SEQUENCE: 26

```
His Met His Phe Gly Leu His Gly Leu Val Phe Arg Arg Thr Phe Ala
1               5                   10                  15

Ile Arg Ser Tyr Glu Val Gly Pro Asp Arg Ser Thr Ser Ile Leu Ala
            20                  25                  30

Val Met Asn His Met Gln Glu Ala Thr Leu Asn His Ala Lys Ser Val
        35                  40                  45

Gly Ile Leu Gly Asp Gly Phe Gly Thr Thr Leu Glu Met Ser Lys Arg
    50                  55                  60

Asp Leu Met Trp Val Val Arg Arg Thr His Val Ala Val Glu Arg Tyr
65                  70                  75                  80

Pro Thr Trp Gly Asp Thr Val Glu Val Glu Cys Trp Ile Gly Ala Ser
                85                  90                  95

Gly Asn Asn Gly Met Arg Arg Asp Phe Leu Val Arg Asp Cys Lys Thr
            100                 105                 110

Gly Glu Ile Leu Thr Arg Cys Thr Ser Leu Ser Val Leu Met Asn Thr
        115                 120                 125

Arg Thr Arg Arg Leu Ser Thr Ile Pro Asp Glu Val Arg Gly Glu Ile
    130                 135                 140

Gly Pro Ala Phe Ile Asp Asn Val Ala Val Lys Asp Asp Glu Ile Lys
145                 150                 155                 160

Lys Leu Gln Lys Leu Asn Asp Ser Thr Ala Asp Tyr Ile Gln Gly Gly
                165                 170                 175

Leu Thr Pro Arg Trp Asn Asp Leu Asp Val Asn Gln His Val Asn Asn
            180                 185                 190

Leu Lys Tyr Val Ala Trp Val Phe Glu Thr Val Pro Asp Ser Ile Phe
        195                 200                 205

Glu Ser His His Ile Ser Ser Phe Thr Leu Glu Tyr Arg Arg Glu Cys
    210                 215                 220

Thr Arg Asp Ser Val Leu Arg Ser Leu Thr Thr Val Ser Gly Gly Ser
225                 230                 235                 240

Ser Glu Ala Gly Leu Val Cys Asp His Leu Leu Gln Leu Glu Gly Gly
                245                 250                 255

Ser Glu Val Leu Arg Ala Arg Thr Glu Trp Arg Pro Lys Leu Thr Asp
            260                 265                 270

Ser Phe Arg Gly Ile Ser Val Ile Pro Ala Ile Glu Gly Arg Ala His
        275                 280                 285

His His His His His His His
    290                 295
```

<210> SEQ ID NO 27
<211> LENGTH: 930
<212> TYPE: DNA
<213> ORGANISM: Yarrowia lipolytica
<220> FEATURE:
<221> NAME/KEY: misc_feature
<223> OTHER INFORMATION: palmitoyl-acyl carrier protein

<400> SEQUENCE: 27

```
atgaaactcg ttactctggc aatccagcta tccacagtgc tagccactac cccagtggtt      60
ctctggcatg gtctcggcga cagatatgac tctccaggaa tgaccggtgt ggcggaccaa     120
atccgcgaca tttaccctga catttacgtg cattcagtcg gactctctga agacggcgga     180
aaagatcagc aaatgggtct tctaggcaac gtaagagagc aagttgagag tgtctgcgac     240
cagctggcag caataccaga gttgaagggc gggttcaatg ccatcggatt ttcccaagga     300
ggtctgtttc ttcgttcata cgccgagttg tgtcccttga caaacgcctc agctcctgtt     360
ctccgaaagc tcatcacatt tggctcccct cataacggaa ttgctgatat gccgctctgt     420
gggcccagcg acttcctttg caagtctcgt aacaagctgt tcaagagtca ggtgtggact     480
aagaactctc aaacgaatgt ggtagtggca cagtattatc gggaccctaa ccacatggac     540
gtgtacctgg agaagtctgg atttctggca gacatcaaca acgagaggca acaaaagaac     600
aagacctacg acctgtctta tttggagaag tttgtcatgg tcatgttctc ggaggatacc     660
acagtagtgc ctatggagag tgcatggttc aagaggtgg atctcgaaag tgggcaagtc     720
acccaccttg aagacagaga gatataccaa gaggactgga ttggacttaa gaagcttgga     780
aagcgtggtg atcttgagtt ccacacggtc catggacagc acatggagat caacgacgac     840
gtgattgaaa cgtttgcctt gagatattta ggcgacgatg acgatatcaa ggccggtgac     900
gactttgtgt ttgtaaacca agctaaatag                                      930
```

<210> SEQ ID NO 28
<211> LENGTH: 309
<212> TYPE: PRT
<213> ORGANISM: Yarrowia lipolytica
<220> FEATURE:
<221> NAME/KEY: MISC_FEATURE
<223> OTHER INFORMATION: palmitoyl-acyl carrier protein

<400> SEQUENCE: 28

```
Met Lys Leu Val Thr Leu Ala Ile Gln Leu Ser Thr Val Leu Ala Thr
1               5                   10                  15

Thr Pro Val Val Leu Trp His Gly Leu Gly Asp Arg Tyr Asp Ser Pro
            20                  25                  30

Gly Met Thr Gly Val Ala Asp Gln Ile Arg Asp Ile Tyr Pro Asp Ile
        35                  40                  45

Tyr Val His Ser Val Gly Leu Ser Glu Asp Gly Gly Lys Asp Gln Gln
    50                  55                  60

Met Gly Leu Leu Gly Asn Val Arg Glu Gln Val Glu Ser Val Cys Asp
65                  70                  75                  80

Gln Leu Ala Ala Ile Pro Glu Leu Lys Gly Gly Phe Asn Ala Ile Gly
                85                  90                  95

Phe Ser Gln Gly Gly Leu Phe Leu Arg Ser Tyr Ala Glu Leu Cys Pro
            100                 105                 110

Leu Thr Asn Ala Ser Ala Pro Val Leu Arg Lys Leu Ile Thr Phe Gly
        115                 120                 125
```

```
Ser Pro His Asn Gly Ile Ala Asp Met Pro Leu Cys Gly Pro Ser Asp
    130                 135                 140
Phe Leu Cys Lys Ser Arg Asn Lys Leu Phe Lys Ser Gln Val Trp Thr
145                 150                 155                 160
Lys Asn Ser Gln Thr Asn Val Val Ala Gln Tyr Tyr Arg Asp Pro
                165                 170                 175
Asn His Met Asp Val Tyr Leu Glu Lys Ser Gly Phe Leu Ala Asp Ile
                180                 185                 190
Asn Asn Glu Arg Gln Gln Lys Asn Lys Thr Tyr Asp Leu Ser Tyr Leu
            195                 200                 205
Glu Lys Phe Val Met Val Met Phe Ser Glu Thr Thr Val Val Pro
    210                 215                 220
Met Glu Ser Ala Trp Phe Gln Glu Val Asp Leu Glu Ser Gly Gln Val
225                 230                 235                 240
Thr His Leu Glu Asp Arg Glu Ile Tyr Gln Glu Asp Trp Ile Gly Leu
                245                 250                 255
Lys Lys Leu Gly Lys Arg Gly Asp Leu Glu Phe His Thr Val His Gly
                260                 265                 270
Gln His Met Glu Ile Asn Asp Asp Val Ile Glu Thr Phe Ala Leu Arg
    275                 280                 285
Tyr Leu Gly Asp Asp Asp Ile Lys Ala Gly Asp Asp Phe Val Phe
    290                 295                 300
Val Asn Gln Ala Lys
305

<210> SEQ ID NO 29
<211> LENGTH: 2043
<212> TYPE: DNA
<213> ORGANISM: Candida tropicalis
<220> FEATURE:
<221> NAME/KEY: misc_feature
<223> OTHER INFORMATION: cytochrome P450 reductase

<400> SEQUENCE: 29
atggcattag ataagttaga tttatatgtt attataacat tggtggttgc aattgcagct      60
tattttgcaa agaatcagtt tcttgaccaa caacaagata ccgggttcct taatactgat     120
agtggagatg gtaattcaag agatatctta caagctttga agaagaacaa taaaaatacg     180
ttattattat ttggatccca aacaggtaca gcagaagatt atgccaacaa attgtcaaga     240
gaattgcatt caagatttgg tttgaaaacc atggttgctg atttcgctga ttatgatttc     300
gaaaacttcg gagatattac tgaagatatc ttggttttct ttattgttgc tacttatggt     360
gaaggtgaac caaccgataa tgctgacgaa tttcacactt ggttgactga agaagctgac     420
accttgagta ctttgaaata tactgttttt ggtttgggta attcaactta tgaattcttc     480
aatgctattg gtagaaaatt tgacagattg ttgggagaaa aggtggtga cagatttgct     540
gaatacggtg aaggtgacga tggtactggt actttagatg aagatttctt ggcctggaag     600
gataacgtgt tgattccttt aaagaatgat tgaattttg aagaaaaga gttgaaatac     660
gaaccaaatg ttaaattgac tgaaagagat gatttatctg caatgatcc agaagtctcc     720
ttgggtgaac aaatgtcaa atacattaaa tctgaaggtg ttgacttaac taaaggtcca     780
tttgatcata ctcatccatt tttggctaga attgttaaaa ctaaagaatt gtttacttct     840
gaagacagac attgtgttca tgttgaattt gatatttctg aatcaaactt gaaatatacc     900
accggtgatc atcttgcaat ctggccatct aactctgatg aaaacattaa gcaatttgcc     960
```

-continued

```
aaatgttttg gtttagaaga caaacttgat actgttattg aattgaaagc tttggattcc    1020
acttattcca tcccattccc taatccaatc acttatggag ctgttattag acaccatttg    1080
gaaatttcag gtcctgtttc tagacaattt ttcttatcta ttgctggatt tgcccctgat    1140
gaagaaacta aaaagtcatt tactagaatt ggtggtgata agcaagaatt tgctagtaaa    1200
gtcacccgta gaaaattcaa cattgccgat gctttattat ttgcttccaa caacagacca    1260
tggtccgatg ttccattcga attccttatt gaaaatgtcc aacacttaac tcctcgttat    1320
tactccattt cttcttcctc attaagtgaa aagcaaacca ttaatgttac tgctgttgtt    1380
gaagccgaag aagaagctga tggaagacca gttactggtg ttgtcaccaa cttgttgaag    1440
aatattgaaa ttgaacaaaa caaaactggt gaaaccccaa tggttcatta tgatttgaat    1500
ggtccaagag gcaaatttag caagttcaga ttgccagttc acgttagaag atctaatttc    1560
aaattaccaa agaatagcac taccccagtt attttgattg gtccaggtac cggtgttgca    1620
ccattgagag gttttgttag agaaagagtt caacaagtta aaaatggtgt taatgttggt    1680
aagactgtat tgttttatgg atgtagaaat tccgaacaag atttcttgta caaacaagaa    1740
tggagtgaat atgcctcagt attgggagaa aatttcgaaa tgtttaatgc cttctcaaga    1800
caagatccaa ctaagaaagt ttatgttcaa gataagattt tagaaaatag tgctcttgtt    1860
gatgagttat tatctagtgg agcaattatt tatgtttgtg gtgatgccag tagaatggct    1920
agagatgttc aagctgcaat tgccaagatt gttgccaaaa gtagagatat ccacgaagat    1980
aaagctgctg aattggttaa atcttggaaa gttcaaaata gataccaaga agatgtctgg    2040
taa                                                                 2043
```

<210> SEQ ID NO 30
<211> LENGTH: 680
<212> TYPE: PRT
<213> ORGANISM: Candida tropicalis
<220> FEATURE:
<221> NAME/KEY: MISC_FEATURE
<223> OTHER INFORMATION: cytochrome P450 reductase

<400> SEQUENCE: 30

```
Met Ala Leu Asp Lys Leu Asp Leu Tyr Val Ile Ile Thr Leu Val Val
1               5                   10                  15

Ala Ile Ala Ala Tyr Phe Ala Lys Asn Gln Phe Leu Asp Gln Gln Gln
                20                  25                  30

Asp Thr Gly Phe Leu Asn Thr Asp Ser Gly Asp Gly Asn Ser Arg Asp
            35                  40                  45

Ile Leu Gln Ala Leu Lys Lys Asn Asn Lys Asn Thr Leu Leu Leu Phe
        50                  55                  60

Gly Ser Gln Thr Gly Thr Ala Glu Asp Tyr Ala Asn Lys Leu Ser Arg
65                  70                  75                  80

Glu Leu His Ser Arg Phe Gly Leu Lys Thr Met Val Ala Asp Phe Ala
                85                  90                  95

Asp Tyr Asp Phe Glu Asn Phe Gly Asp Ile Thr Glu Asp Ile Leu Val
            100                 105                 110

Phe Phe Ile Val Ala Thr Tyr Gly Glu Gly Glu Pro Thr Asp Asn Ala
        115                 120                 125

Asp Glu Phe His Thr Trp Leu Thr Glu Glu Ala Asp Thr Leu Ser Thr
    130                 135                 140

Leu Lys Tyr Thr Val Phe Gly Leu Gly Asn Ser Thr Tyr Glu Phe Phe
145                 150                 155                 160
```

-continued

```
Asn Ala Ile Gly Arg Lys Phe Asp Arg Leu Leu Gly Glu Lys Gly Gly
                165                 170                 175
Asp Arg Phe Ala Glu Tyr Gly Glu Gly Asp Asp Gly Thr Gly Thr Leu
            180                 185                 190
Asp Glu Asp Phe Leu Ala Trp Lys Asp Asn Val Phe Asp Ser Leu Lys
        195                 200                 205
Asn Asp Leu Asn Phe Glu Glu Lys Glu Leu Lys Tyr Glu Pro Asn Val
    210                 215                 220
Lys Leu Thr Glu Arg Asp Asp Leu Ser Gly Asn Asp Pro Glu Val Ser
225                 230                 235                 240
Leu Gly Glu Pro Asn Val Lys Tyr Ile Lys Ser Glu Gly Val Asp Leu
                245                 250                 255
Thr Lys Gly Pro Phe Asp His Thr His Pro Phe Leu Ala Arg Ile Val
            260                 265                 270
Lys Thr Lys Glu Leu Phe Thr Ser Glu Asp Arg His Cys Val His Val
        275                 280                 285
Glu Phe Asp Ile Ser Glu Ser Asn Leu Lys Tyr Thr Thr Gly Asp His
    290                 295                 300
Leu Ala Ile Trp Pro Ser Asn Ser Asp Glu Asn Ile Lys Gln Phe Ala
305                 310                 315                 320
Lys Cys Phe Gly Leu Glu Asp Lys Leu Asp Thr Val Ile Glu Leu Lys
                325                 330                 335
Ala Leu Asp Ser Thr Tyr Ser Ile Pro Phe Pro Asn Pro Ile Thr Tyr
            340                 345                 350
Gly Ala Val Ile Arg His His Leu Glu Ile Ser Gly Pro Val Ser Arg
        355                 360                 365
Gln Phe Phe Leu Ser Ile Ala Gly Phe Ala Pro Asp Glu Glu Thr Lys
    370                 375                 380
Lys Ser Phe Thr Arg Ile Gly Gly Asp Lys Gln Glu Phe Ala Ser Lys
385                 390                 395                 400
Val Thr Arg Arg Lys Phe Asn Ile Ala Asp Ala Leu Leu Phe Ala Ser
                405                 410                 415
Asn Asn Arg Pro Trp Ser Asp Val Pro Phe Glu Phe Leu Ile Glu Asn
            420                 425                 430
Val Gln His Leu Thr Pro Arg Tyr Tyr Ser Ile Ser Ser Ser Ser Leu
        435                 440                 445
Ser Glu Lys Gln Thr Ile Asn Val Thr Ala Val Val Glu Ala Glu Glu
    450                 455                 460
Glu Ala Asp Gly Arg Pro Val Thr Gly Val Val Thr Asn Leu Leu Lys
465                 470                 475                 480
Asn Ile Glu Ile Glu Gln Asn Lys Thr Gly Glu Thr Pro Met Val His
                485                 490                 495
Tyr Asp Leu Asn Gly Pro Arg Gly Lys Phe Ser Lys Phe Arg Leu Pro
            500                 505                 510
Val His Val Arg Arg Ser Asn Phe Lys Leu Pro Lys Asn Ser Thr Thr
        515                 520                 525
Pro Val Ile Leu Ile Gly Pro Gly Thr Gly Val Ala Pro Leu Arg Gly
    530                 535                 540
Phe Val Arg Glu Arg Val Gln Gln Val Lys Asn Gly Val Asn Val Gly
545                 550                 555                 560
Lys Thr Val Leu Phe Tyr Gly Cys Arg Asn Ser Glu Gln Asp Phe Leu
                565                 570                 575
Tyr Lys Gln Glu Trp Ser Glu Tyr Ala Ser Val Leu Gly Glu Asn Phe
```

```
                580             585             590
Glu Met Phe Asn Ala Phe Ser Arg Gln Asp Pro Thr Lys Lys Val Tyr
                        595             600             605
Val Gln Asp Lys Ile Leu Glu Asn Ser Ala Leu Val Asp Glu Leu Leu
            610             615             620
Ser Ser Gly Ala Ile Ile Tyr Val Cys Gly Asp Ala Ser Arg Met Ala
625             630             635             640
Arg Asp Val Gln Ala Ala Ile Ala Lys Ile Val Ala Lys Ser Arg Asp
                645             650             655
Ile His Glu Asp Lys Ala Ala Glu Leu Val Lys Ser Trp Lys Val Gln
                660             665             670
Asn Arg Tyr Gln Glu Asp Val Trp
            675             680

<210> SEQ ID NO 31
<211> LENGTH: 2043
<212> TYPE: DNA
<213> ORGANISM: Artificial sequence
<220> FEATURE:
<223> OTHER INFORMATION: Synthetic polynucleotide

<400> SEQUENCE: 31
atggctctgg ataaactgga cctgtatgtc atcatcacgc tggtcgtcgc aatcgctgcc      60
tacttcgcaa aaatcaatt cctggaccag caacaggata ccggttttct gaacacggat     120
tcaggcgacg gtaattcgcg tgatattctg caagccctga gaaaaacaa taaaaacacc     180 ctgctgctgt tggtagcca gaccggcacg gcggaagatt atgccaataa actgagccgt     240
gaactgcatt ctcgcttcgg tctgaaaacg atggtggcgg attttgccga ttatgacttt     300
gaaaacttcg gcgatattac cgaagacatc ctggtctttt tcattgtggc tacctacggc     360
gaaggtgaac cgacggataa tgcggacgaa tttcacacct ggctgacgga agaagccgat     420
accctgtcaa cgctgaaata ccgttttttc ggcctgggta ctcgacgta cgaattttttc     480 aatgcgatcg gtcgtaaatt tgatcgcctg ctgggcgaaa aaggcggtga ccgtttcgcc     540
gaatatggcg aaggtgatga cggcaccggt acgctggatg aagacttcct ggcatggaaa     600
gataacgtct ttgacagcct gaaaaacgat ctgaacttcg aagaaaaaga actgaaatac     660
gaaccgaacg ttaaactgac cgaacgcgat gacctgagcg gtaacgatcc ggaagtttcg     720
ctgggcgaac cgaatgtcaa atacattaaa agtgagggtg tggatctgac caaaggcccg     780
ttcgaccata cgcaccccgtt tctggcgcgt attgttaaaa cgaaagaact gtttacgagc     840
gaagatcgcc attgcgttca cgtcgaattt gacatcagcg aatctaacct gaaatatacc     900
acgggtgatc atctggcgat ttggccgagt aactccgacg aaaatatcaa acagttcgcc     960
aaatgttttg gcctggaaga taaactggac accgtgattg aactgaaagc actggattca    1020
acgtattcga ttccgtttcc gaatccgatc acctacggtg ctgtgattcg tcatcacctg    1080
gaaatcagcg gcccggtttc tcgccaattt ttcctgagca ttgcaggctt cgctccggat    1140
gaagaaacca aaaatctttt acgcgtatc ggcggtgaca acaggaatt tgccagtaaa    1200 gtgacccgtc gcaaattcaa cattgcagat gctctgctgt ttgcaagtaa caatcgtccg    1260
tggtccgacg ttccgtttga atttctgatc gaaaacgtcc aacacctgac cccgcgctat    1320
tacagcatta gctctagttc cctgtctgaa aaacagacca tcaatgttac ggcagtggtt    1380
gaagctgaag aagaagcgga tggtcgtccg gtcaccggtg tcgtgacgaa cctgctgaaa    1440
aacatcgaaa tcgaacagaa caaaaccggt gaaacgccga tggtgcatta tgatctgaat    1500
```

```
ggtccgcgtg gcaaattttc caaattccgc ctgccggtgc acgttcgtcg cagtaacttt      1560
aaactgccga aaaattccac cacgccggtt attctgatcg gtccgggtac cggtgtggca      1620
ccgctgcgtg gttttgttcg tgaacgcgtg caacaggtta aaaacggtgt caatgtgggc      1680
aaaaccgtgc tgttttacgg ttgccgcaac tctgaacaag atttcctgta taaacaggaa      1740
tggagtgaat acgcatccgt tctgggcgaa aactttgaaa tgttcaatgc ttttcgcgt       1800 caagatccga ccaagaaagt gtatgtccag gacaaaattc tggaaaattc tgccctggtc      1860
gatgaactgc tgtcatcggg tgcaattatc tacgtgtgtg gcgatgcctc ccgtatggca      1920
cgcgacgtcc aggcagccat tgctaaaatc gtggcgaaat cacgcgatat ccatgaagac      1980
aaagcggcag aactggtcaa atcgtggaaa gtgcagaatc gttatcagga gatgtgtgg      2040 taa                                                                    2043

<210> SEQ ID NO 32
<211> LENGTH: 2115
<212> TYPE: DNA
<213> ORGANISM: Candida albicans
<220> FEATURE:
<221> NAME/KEY: misc_feature
<223> OTHER INFORMATION: fatty alcohol oxgenase

<400> SEQUENCE: 32
atggctccat ttttgcccga ccaggtcgac tacaaacacg tcgacaccct tatgttatta       60
tgtgacggga tcatccacga aaccaccgtg gacgaaatca agacgtcat tgcccctgac       120 ttccccgccg acaaatacga ggagtacgtc aggacattca ccaaaccctc cgaaaccccca      180 gggttcaggg aaaccgtcta caaccaccgtc aacgcaaaca ccatggatgc aatccaccag     240
ttcattatct tgaccaatgt tttgggatca agggtcttgg caccagcttt gaccaactcg      300
ttgactccta tcaaggacat gagcttggaa gaccgtgaaa agttgttagc ctcgtggcgt      360 gactcccccta ttgctgctaa aaggaagttg ttcaggttgg tttctacgct taccttggtc     420
acgttcacga gattggccaa tgagttgcat ttgaaagcca ttcattatcc aggaagagaa      480
gaccgtgaaa aggcttatga aacccaggag attgaccctt taagtacca gttttttggaa     540 aaaccgaagt tttacggcgc tgagttgtac ttgccagata ttgatgtgat cattattgga      600
tctggggccg gtgctggtgt cgtggcccac actttgacca acgacggctt caagagtttg      660
gttttggaaa agggcagata ctttagcaac tccgagttga actttgatga caaggacggg      720
gttcaagaat taccaaaag tggaggtact ttgaccaccg tcaaccagca gttgtttgtt       780
cttgctggtt ccacttttgg tggtggtacc actgtcaatt ggtcggcctg tcttaaaacg      840
ccattcaagg tgcgtaagga atggtatgat gagtttggcg ttgactttgc tgccgatgaa      900
gcctacgaca agcacagga ttatgttttgg cagcaaatgg gagcttctac cgaaggcatc      960
acccactctt tggctaacga gattatt g aaggtggca agaaattagg ttacaaggcc         1020
aaggtattag accaaaacag cggtggtcat cctcatcaca gatgcggttt ctgttatttg      1080
ggttgtaagc acggtatcaa gcagggctct gttaataact ggtttagaga cgcagctgcc      1140
cacggttctc agttcatgca acaggttaga gttttgcaaa tccttaacaa gaagggcatc      1200
gcttatggta tcttgtgtga ggatgttgta accggtgcca agttcaccat tactggcccc      1260
aaaaagtttg ttgttgccgc cggcgcctta aacactccat ctgtgttggt caactccgga      1320
ttcaagaaca agaacatcgg taagaactta actttgcatc cagtttctgt cgtgtttggt      1380
gattttggca aagacgttca agcagatcac ttccacaact ccatcatgac tgctctttgt      1440
```

-continued

```
tcagaagccg ctgatttaga cggcaagggt catggatgca gaattgaaac catcttgaac    1500
gctccattca tccaggcttc attcttacca tggagaggta gtaacgaggc tagacgagac    1560
ttgttgcgtt acaacaacat ggtggccatg ttacttctta gtcgtgatac caccagtggt    1620
tccgtttcgt cccatccaac taaacctgaa gcattagttg tcgagtacga cgtgaacaag    1680
tttgacagaa actccatctt gcaggcattg ttggtcactg ctgacttgtt gtacattcaa    1740
ggtgccaaga gaatccttag tccccaacca tgggtgccaa ttttgaatc cgacaagcca     1800
aaggataaga gatcaatcaa ggacgaggac tatgtcgaat ggagagccaa ggttgccaag    1860
attcctttg acacctacgg ctcgccttat ggttcggcgc atcaaatgtc ttcttgtcgt    1920
atgtcaggta agggtcctaa atacggtgct gttgataccg atggtagatt gtttgaatgt    1980
tcgaatgttt atgttgctga cgctagtctt ttgccaactg ctagcggtgc taatcctatg    2040
gtcaccacca tgactcttgc aagacatgtt gcgttaggtt tggcagactc cttgaagacc    2100
aaggccaagt tgtag                                                     2115
```

<210> SEQ ID NO 33
<211> LENGTH: 704
<212> TYPE: PRT
<213> ORGANISM: Candida albicans
<220> FEATURE:
<221> NAME/KEY: MISC_FEATURE
<223> OTHER INFORMATION: fatty alcohol oxgenase

<400> SEQUENCE: 33

```
Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Gly Ser Gly Ala Gly Ala Gly Val Val
        195                 200                 205

Ala His Thr Leu Thr Asn Asp Gly Phe Lys Ser Leu Val Leu Glu Lys
    210                 215                 220

Gly Arg Tyr Phe Ser Asn Ser Glu Leu Asn Phe Asp Asp Lys Asp Gly
```

```
            225                 230                 235                 240
Val Gln Glu Leu Tyr Gln Ser Gly Gly Thr Leu Thr Thr Val Asn Gln
                    245                 250                 255

Gln Leu Phe Val Leu Ala Gly Ser Thr Phe Gly Gly Thr Thr Val
                260                 265                 270

Asn Trp Ser Ala Cys Leu Lys Thr Pro Phe Lys Val Arg Lys Glu Trp
            275                 280                 285

Tyr Asp Glu Phe Gly Val Asp Phe Ala Ala Asp Glu Ala Tyr Asp Lys
        290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Lys Lys Leu
                325                 330                 335

Gly Tyr Lys Ala Lys Val Leu Asp Gln Asn Ser Gly His Pro His
                340                 345                 350

His Arg Cys Gly Phe Cys Tyr Leu Gly Cys Lys His Gly Ile Lys Gln
        355                 360                 365

Gly Ser Val Asn Asn Trp Phe Arg Asp Ala Ala His Gly Ser Gln
        370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
                405                 410                 415

Ile Thr Gly Pro Lys Lys Phe Val Val Ala Ala Gly Ala Leu Asn Thr
                420                 425                 430

Pro Ser Val Leu Val Asn Ser Gly Phe Lys Asn Lys Asn Ile Gly Lys
            435                 440                 445

Asn Leu Thr Leu His Pro Val Ser Val Val Phe Gly Asp Phe Gly Lys
        450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
                500                 505                 510

Gly Ser Asn Glu Ala Arg Arg Asp Leu Leu Arg Tyr Asn Asn Met Val
            515                 520                 525

Ala Met Leu Leu Leu Ser Arg Asp Thr Thr Ser Gly Ser Val Ser Ser
        530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Pro Trp Val
                580                 585                 590

Pro Ile Phe Glu Ser Asp Lys Pro Lys Asp Lys Arg Ser Ile Lys Asp
            595                 600                 605

Glu Asp Tyr Val Glu Trp Arg Ala Lys Val Ala Lys Ile Pro Phe Asp
        610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655
```

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
    690                 695                 700

<210> SEQ ID NO 34
<211> LENGTH: 2115
<212> TYPE: DNA
<213> ORGANISM: Artificial sequence
<220> FEATURE:
<223> OTHER INFORMATION: Synthetic polynucleotide

<400> SEQUENCE: 34

| | |
|---|---|
| atggctccat ttttgcccga ccaggtcgac tacaaacacg tcgacaccct tatgttatta | 60 |
| tgtgacggga tcatccacga aaccaccgtg gacgaaatca agacgtcat tgcccctgac | 120 |
| ttccccgccg acaaatacga ggagtacgtc aggacattca ccaaaccctc cgaaacccca | 180 |
| gggttcaggg aaaccgtcta caacaccgtc aacgcaaaca ccatggatgc aatccaccag | 240 |
| ttcattatct tgaccaatgt tttgggatca agggtcttgg caccagcttt gaccaactcg | 300 |
| ttgactccta tcaaggacat gagcttggaa gaccgtgaaa agttgttagc ctcgtggcgt | 360 |
| gactcccta ttgctgctaa aggaagttg ttcaggttgg tttctacgct taccttggtc | 420 |
| acgttcacga gattggccaa tgagttgcat ttgaaagcca ttcattatcc aggaagagaa | 480 |
| gaccgtgaaa aggcttatga aacccaggag attgacccctt taagtacca gttttggaa | 540 |
| aaaccgaagt tttacggcgc tgagttgtac ttgccagata ttgatgtgat cattattgga | 600 |
| tctggggccg gtgctggtgt cgtggcccac actttgacca cgacggctt caagagtttg | 660 |
| gttttggaaa agggcagata ctttagcaac tccgagttga cttgatga caaggacggg | 720 |
| gttcaagaat tataccaaag tggaggtact ttgaccaccg tcaaccagca gttgtttgtt | 780 |
| cttgctggtt ccacttttgg tggtggtacc actgtcaatt ggtcggcctg tcttaaaacg | 840 |
| ccattcaagg tgcgtaagga atggtatgat gagtttggcg ttgactttgc tgccgatgaa | 900 |
| gcctacgaca agcacagga ttatgtttgg cagcaaatgg gagcttctac cgaaggcatc | 960 |
| acccactctt tggctaacga gattattatt gaagtggca agaaattagg ttacaaggcc | 1020 |
| aaggtattag accaaaacag cggtggtcat cctcatcaca gatgcggttt ctgttatttg | 1080 |
| ggttgtaagc acggtatcaa gcagggctct gttaataact ggtttagaga cgcagctgcc | 1140 |
| cacggttctc agttcatgca acaggttaga gttttgcaaa tccttaacaa gaagggcatc | 1200 |
| gcttatggta tcttgtgtga ggatgttgta accggtgcca agttcaccat tactggcccc | 1260 |
| aaaaagtttg ttgttgccgc cggcgcctta aacactccat ctgtgttggt caactccgga | 1320 |
| ttcaagaaca gaacatcgg taagaactta actttgcatc cagtttctgt cgtgtttggt | 1380 |
| gattttggca aagacgttca agcagatcac ttccacaact ccatcatgac tgctctttgt | 1440 |
| tcagaagccg ctgatttaga cggcaagggt catggatgca gaattgaaac catcttgaac | 1500 |
| gctccattca tccaggcttc attcttacca tggagaggta gtaacgaggc tagacgagac | 1560 |
| ttgttgcgtt acaacaacat ggtggccatg ttacttctta gtcgtgatac caccagtggt | 1620 |
| tccgtttcgt cccatccaac taaacctgaa gcattagttg tcgagtacga cgtgaacaag | 1680 |
| tttgacagaa actccatctt gcaggcattg ttggtcactg ctgacttgtt gtacattcaa | 1740 |
| ggtgccaaga gaatccttag tccccaacca tgggtgccaa ttttgaatc cgacaagcca | 1800 |

```
aaggataaga gatcaatcaa ggacgaggac tatgtcgaat ggagagccaa ggttgccaag    1860
attccttttg acacctacgg ctcgccttat ggttcggcgc atcaaatgtc ttcttgtcgt    1920
atgtcaggta agggtcctaa atacggtgct gttgataccg atggtagatt gtttgaatgt    1980
tcgaatgttt atgttgctga cgctagtctt ttgccaactg ctagcggtgc taatcctatg    2040
gtcaccacca tgactcttgc aagacatgtt gcgttaggtt tggcagactc cttgaagacc    2100
aaggccaagt tgtag                                                    2115

<210> SEQ ID NO 35
<211> LENGTH: 768
<212> TYPE: DNA
<213> ORGANISM: Candida albicans
<220> FEATURE:
<221> NAME/KEY: misc_feature
<223> OTHER INFORMATION: fatty aldehyde hydrogenase

<400> SEQUENCE: 35
atgccagatg gtactccaag attcacatgt aaaggtaaag aaattcttca tttcatgggt      60
tgctctacct tctcccaata cactgttgtt gctgatattt ctgtcgttgc cattaatgaa     120
aaagctgagt tgaaaaagc ttgtttgtta ggatgtggta ttactactgg ttacggtgcg     180
gccaccatta ctgcaaatgt ccaagaaggt gataatgttg ctgtctttgg tggtggttgt     240
gttggtttat ctgttatcca aggttgtaaa gaaagaaaag tcaacaagat catttttggtt    300 gatataaacg acaaaaaaga gaatggggt aaacaatttg gtgccactga ttttgtcaac     360
tcaactaaat tgccagaggg gactaccatt gtcgataaat taattgaaat gaccgatggt     420
ggttgtgact acactttga ttgtactggt aacgtcaacg tcatgagaaa tgcattagaa     480
gcttgtcaca aggttgggg tacttctatt atcattgggg ttgctgctgc tggtaaagaa     540
atctctacca gaccatttca attagttacc ggtagggtgt ggaaaggtgc tgcctttggt     600
ggtgttaaag gtagatctca attgccaggt atagttgaag attacttgga tggtaaactc     660
aaggttgaag aattcatcac ccacagagaa ccattggaca agatcaacac tgctttcgat     720
gaaatgcacg gaggcgactg tattagagct gttgtttctt tatggtga                  768

<210> SEQ ID NO 36
<211> LENGTH: 255
<212> TYPE: PRT
<213> ORGANISM: Candida albicans
<220> FEATURE:
<221> NAME/KEY: MISC_FEATURE
<223> OTHER INFORMATION: fatty aldehyde hydrogenase

<400> SEQUENCE: 36

Met Pro Asp Gly Thr Pro Arg Phe Thr Cys Lys Gly Lys Glu Ile Leu
1               5                   10                  15

His Phe Met Gly Cys Ser Thr Phe Ser Gln Tyr Thr Val Val Ala Asp
            20                  25                  30

Ile Ser Val Val Ala Ile Asn Glu Lys Ala Glu Phe Glu Lys Ala Cys
        35                  40                  45

Leu Leu Gly Cys Gly Ile Thr Thr Gly Tyr Gly Ala Ala Thr Ile Thr
    50                  55                  60

Ala Asn Val Gln Glu Gly Asp Asn Val Ala Val Phe Gly Gly Gly Cys
65                  70                  75                  80

Val Gly Leu Ser Val Ile Gln Gly Cys Lys Glu Arg Lys Val Asn Lys
                85                  90                  95
```

Ile Ile Leu Val Asp Ile Asn Asp Lys Lys Glu Glu Trp Gly Lys Gln
            100                 105                 110

Phe Gly Ala Thr Asp Phe Val Asn Ser Thr Lys Leu Pro Glu Gly Thr
        115                 120                 125

Thr Ile Val Asp Lys Leu Ile Glu Met Thr Asp Gly Gly Cys Asp Tyr
    130                 135                 140

Thr Phe Asp Cys Thr Gly Asn Val Asn Val Met Arg Asn Ala Leu Glu
145                 150                 155                 160

Ala Cys His Lys Gly Trp Gly Thr Ser Ile Ile Gly Val Ala Ala
                165                 170                 175

Ala Gly Lys Glu Ile Ser Thr Arg Pro Phe Gln Leu Val Thr Gly Arg
            180                 185                 190

Val Trp Lys Gly Ala Ala Phe Gly Gly Val Lys Gly Arg Ser Gln Leu
        195                 200                 205

Pro Gly Ile Val Glu Asp Tyr Leu Asp Gly Lys Leu Lys Val Glu Glu
    210                 215                 220

Phe Ile Thr His Arg Glu Pro Leu Asp Lys Ile Asn Thr Ala Phe Asp
225                 230                 235                 240

Glu Met His Gly Gly Asp Cys Ile Arg Ala Val Val Ser Leu Trp
                245                 250                 255

<210> SEQ ID NO 37
<211> LENGTH: 768
<212> TYPE: DNA
<213> ORGANISM: Artificial sequence
<220> FEATURE:
<223> OTHER INFORMATION: Synthetic polynucleotide

<400> SEQUENCE: 37
atgccggacg gtacgccgcg cttcacctgt aaaggcaaag aaatcctgca cttcatgggc    60
tgtagcacgt tcagtcaata tcggttgtt gcagacatca gcgtggttgc catcaacgaa    120
aaagcagaat tcgaaaaagc ttgcctgctg ggttgtggca tcaccacggg ttatggcgcg    180
gccaccatta cggcgaacgt gcaggaaggt gataatgttg cggtgtttgg cggtggctgc    240
gtgggtctga gtgttatcca aggctgtaaa gaacgtaaag ttaacaaaat catcctggtc    300
gatattaatg acaagaaaga agaatggggt aaacagtttg gcgccaccga cttcgttaac    360
tccacgaaac tgccggaagg taccacgatc gtggataaac tgattgaaat gaccgatggt    420
ggctgcgact ataccttga ttgtacgggc aacgttaatg tcatgcgcaa tgctctggaa    480
gcgtgccata aggttgggg caccagcatt atcattggtg tggcagctgc gggcaaagaa    540
atctctaccc gtccgtttca gctggtcacc ggtcgtgtgt ggaaaggtgc agcattcggt    600
ggcgtgaaag gtcgtagcca actgccgggc attgttgaag attacctgga cggcaaactg    660
aaagtcgaag aattcatcac ccaccgcgaa ccgctggata aaattaatac ggcgtttgat    720
gaaatgcacg gtggtgattg tatccgcgca gtcgttagcc tgtggtaa              768

<210> SEQ ID NO 38
<211> LENGTH: 2103
<212> TYPE: DNA
<213> ORGANISM: Yarrowia lipolytica
<220> FEATURE:
<221> NAME/KEY: misc_feature
<223> OTHER INFORMATION: acyl-coenzyme A oxidase POX2

<400> SEQUENCE: 38
atgaacccca caacactgg caccattgaa atcaacggta aggagtacaa caccttcacc    60

```
gagcccccg   tggccatggc   tcaggagcga   gccaagacct   ccttcccgt   gcgagagatg        120 acctacttcc  tcgacggtgg   cgagaagaac   accctcaaaa   acgagcagat  catggaggag        180
attgagcgag  accctctttt   caacaacgac   aactactacg   atctcaacaa  ggagcagatc        240
cgagagctca  ccatggagcg   agtcgccaag   ctgtctctgt   ttgtgcgtga  tcagcccgag        300
gacgacatca  agaagcgatt   tgctctcatt   ggtatcgccg   atatgggaac  ctacacccga        360
cttggtgtcc  actacggcct   cttctttggc   ccgtccgag    gtaccggaac  tgccgagcag        420
tttggccact  ggatctccaa   gggagccgga   gacctgcgaa   agttctacgg  atgtttctcc        480
atgaccgagc  tgggccatgg   ctccaacctg   gctggtctcg   agaccaccgc  catctacgat        540
gaggagaccg  acgagttcat   catcaacacc   cctcacattg   ccgccaccaa  gtggtggatt        600
ggaggagccg  cccacaccgc   cacccacact   gtcgtgttcg   cccgactcat  tgtcaagggc        660
aaggactacg  gtgtcaagac   ctttgttgtc   cagctgcgaa   acatcaacga  ccacagcctc        720
aaggtcggta  tctctattgg   tgatatcgga   aagaagatgg   gccgagacgg  tatcgataac        780
ggatggatcc  agttcaccaa   cgtgcgaatc   ccccgacaga   acctgctcat  gaagtacaca        840
aaggtcgacc  gagagggtaa   cgtgacccag   cctcctctgg   ctcagcttac  ctacggttct        900
cttatcactg  tcgagtctc    catggcctct   gattctcacc   aggtcggaaa  gcgattcatc        960
accattgctc  tgcgatacgc   ctgcattcga   cgacagttct   ccaccacccc  cggccagccc       1020
gagaccaaga  tcatcgacta   ccctaccat    cagcgacgac  ttctgcctct  ctggcctat        1080 gtctatgctc  ttaagatgac   tgccgatgag   gttggagctc   tcttctcccg  aaccatgctt       1140
aagatggacg  acctcaagcc   cgacgacaag   gccggcctca   atgaggttgt  ttccgacgtc       1200
aaggagctct  tctccgtctc   cgccggtctc   aaggccttct   ccacctgggc  ttgtgccgac       1260
gtcattgaca  agacccgaca   ggcttgcggt   ggccacggtt   actctggata  caacggtttc       1320
ggccaggcct  acgccgactg   ggttgtccag   tgcacctggg   agggtgacaa  caacattctc       1380
accctttctg  ccgccgagc    tcttatccag   tctgccgttg   ctctgcgaaa  gggcgagcct       1440
gttggtaacg  ccgtttctta   cctgaagcga   tacaaggatc   tggccaacgc  taagctcaat       1500
ggccgatctc  tcaccgaccc   caaggtcctc   gtcgaggcc    gggaggttgc  tgccggtaac       1560
atcatcaacc  gagccaccga   ccagtacgag   aagctcattg   gcgagggtct  taacgccgac       1620
caggcctttg  aggttctgtc   tcagcagcga   ttccaggccg   ccaaggtcca  cacgacga         1680 cacctcattg  ccgctttctt   ctcccgaatt   gacaccgagg   ctggcgaggc  catcaagcag       1740
cccctgctta  acctggctct   gctgtttgcc   ctgtggtcca   tcgaagagga  ctctggtctg       1800
ttcctgcgag  agggcttcct   cgagcccaag   gatatcgaca   ccgtcaccga  gctcgtcaac       1860
aagtactgca  ccactgtgcg   agaggaggtc   attggctaca   ccgatgcctt  caacctgtcc       1920
gactacttca  tcaacgctcc   tattggatgc   tacgatggtg   acgcttaccg  acactacttc       1980
cagaaggtca  cgagcagaa    ccctgcccga  gaccccgac   ctccttacta  cgcctctact       2040
ctcaagccct  tcctttccg    agaggaggag   gatgatgaca   tttgcgagct  tgatgaggaa       2100
tag                                                                            2103
```

<210> SEQ ID NO 39
<211> LENGTH: 700
<212> TYPE: PRT
<213> ORGANISM: Yarrowia lipolytica
<220> FEATURE:
<221> NAME/KEY: MISC_FEATURE
<223> OTHER INFORMATION: acyl-coenzyme A oxidase POX2

<400> SEQUENCE: 39

```
Met Asn Pro Asn Asn Thr Gly Thr Ile Glu Ile Asn Gly Lys Glu Tyr
1               5                   10                  15

Asn Thr Phe Thr Glu Pro Pro Val Ala Met Ala Gln Glu Arg Ala Lys
            20                  25                  30

Thr Ser Phe Pro Val Arg Glu Met Thr Tyr Phe Leu Asp Gly Gly Glu
        35                  40                  45

Lys Asn Thr Leu Lys Asn Glu Gln Ile Met Glu Glu Ile Glu Arg Asp
    50                  55                  60

Pro Leu Phe Asn Asn Asp Asn Tyr Tyr Asp Leu Asn Lys Glu Gln Ile
65                  70                  75                  80

Arg Glu Leu Thr Met Glu Arg Val Ala Lys Leu Ser Leu Phe Val Arg
                85                  90                  95

Asp Gln Pro Glu Asp Asp Ile Lys Lys Arg Phe Ala Leu Ile Gly Ile
            100                 105                 110

Ala Asp Met Gly Thr Tyr Thr Arg Leu Gly Val His Tyr Gly Leu Phe
        115                 120                 125

Phe Gly Ala Val Arg Gly Thr Gly Thr Ala Glu Gln Phe Gly His Trp
130                 135                 140

Ile Ser Lys Gly Ala Gly Asp Leu Arg Lys Phe Tyr Gly Cys Phe Ser
145                 150                 155                 160

Met Thr Glu Leu Gly His Gly Ser Asn Leu Ala Gly Leu Glu Thr Thr
                165                 170                 175

Ala Ile Tyr Asp Glu Glu Thr Asp Glu Phe Ile Ile Asn Thr Pro His
            180                 185                 190

Ile Ala Ala Thr Lys Trp Trp Ile Gly Gly Ala Ala His Thr Ala Thr
        195                 200                 205

His Thr Val Val Phe Ala Arg Leu Ile Val Lys Gly Lys Asp Tyr Gly
    210                 215                 220

Val Lys Thr Phe Val Val Gln Leu Arg Asn Ile Asn Asp His Ser Leu
225                 230                 235                 240

Lys Val Gly Ile Ser Ile Gly Asp Ile Gly Lys Lys Met Gly Arg Asp
                245                 250                 255

Gly Ile Asp Asn Gly Trp Ile Gln Phe Thr Asn Val Arg Ile Pro Arg
            260                 265                 270

Gln Asn Leu Leu Met Lys Tyr Thr Lys Val Asp Arg Glu Gly Asn Val
        275                 280                 285

Thr Gln Pro Pro Leu Ala Gln Leu Thr Tyr Gly Ser Leu Ile Thr Gly
    290                 295                 300

Arg Val Ser Met Ala Ser Asp Ser His Gln Val Gly Lys Arg Phe Ile
305                 310                 315                 320

Thr Ile Ala Leu Arg Tyr Ala Cys Ile Arg Arg Gln Phe Ser Thr Thr
                325                 330                 335

Pro Gly Gln Pro Glu Thr Lys Ile Ile Asp Tyr Pro Tyr His Gln Arg
            340                 345                 350

Arg Leu Leu Pro Leu Leu Ala Tyr Val Tyr Ala Leu Lys Met Thr Ala
        355                 360                 365

Asp Glu Val Gly Ala Leu Phe Ser Arg Thr Met Leu Lys Met Asp Asp
    370                 375                 380

Leu Lys Pro Asp Asp Lys Ala Gly Leu Asn Glu Val Val Ser Asp Val
385                 390                 395                 400

Lys Glu Leu Phe Ser Val Ser Ala Gly Leu Lys Ala Phe Ser Thr Trp
                405                 410                 415
```

Ala Cys Ala Asp Val Ile Asp Lys Thr Arg Gln Ala Cys Gly Gly His
              420                 425                 430

Gly Tyr Ser Gly Tyr Asn Gly Phe Gly Gln Ala Tyr Ala Asp Trp Val
          435                 440                 445

Val Gln Cys Thr Trp Glu Gly Asp Asn Asn Ile Leu Thr Leu Ser Ala
      450                 455                 460

Gly Arg Ala Leu Ile Gln Ser Ala Val Ala Leu Arg Lys Gly Glu Pro
465                 470                 475                 480

Val Gly Asn Ala Val Ser Tyr Leu Lys Arg Tyr Lys Asp Leu Ala Asn
                  485                 490                 495

Ala Lys Leu Asn Gly Arg Ser Leu Thr Asp Pro Lys Val Leu Val Glu
              500                 505                 510

Ala Trp Glu Val Ala Ala Gly Asn Ile Ile Asn Arg Ala Thr Asp Gln
          515                 520                 525

Tyr Glu Lys Leu Ile Gly Glu Gly Leu Asn Ala Asp Gln Ala Phe Glu
      530                 535                 540

Val Leu Ser Gln Gln Arg Phe Gln Ala Ala Lys Val His Thr Arg Arg
545                 550                 555                 560

His Leu Ile Ala Ala Phe Phe Ser Arg Ile Asp Thr Glu Ala Gly Glu
                  565                 570                 575

Ala Ile Lys Gln Pro Leu Leu Asn Leu Ala Leu Phe Ala Leu Trp
              580                 585                 590

Ser Ile Glu Glu Asp Ser Gly Leu Phe Leu Arg Glu Gly Phe Leu Glu
          595                 600                 605

Pro Lys Asp Ile Asp Thr Val Thr Glu Leu Val Asn Lys Tyr Cys Thr
      610                 615                 620

Thr Val Arg Glu Glu Val Ile Gly Tyr Thr Asp Ala Phe Asn Leu Ser
625                 630                 635                 640

Asp Tyr Phe Ile Asn Ala Pro Ile Gly Cys Tyr Asp Gly Asp Ala Tyr
                  645                 650                 655

Arg His Tyr Phe Gln Lys Val Asn Glu Gln Asn Pro Ala Arg Asp Pro
              660                 665                 670

Arg Pro Pro Tyr Tyr Ala Ser Thr Leu Lys Pro Phe Leu Phe Arg Glu
          675                 680                 685

Glu Glu Asp Asp Asp Ile Cys Glu Leu Asp Glu Glu
      690                 695                 700

<210> SEQ ID NO 40
<211> LENGTH: 2100
<212> TYPE: DNA
<213> ORGANISM: Yarrowia lipolytica
<220> FEATURE:
<221> NAME/KEY: misc_feature
<223> OTHER INFORMATION: acyl-coenzyme A oxidase POX 5

<400> SEQUENCE: 40
atgaacaaca acccccaccaa cgtgatcctt ggaggcaagg agtacgacac cttcaccgag    60
cctccggccc agatggagct ggagcgagcc aagacacaat tcaaggtccg agacgtgacc   120
aacttcctca caggcagcga gcaggagaca ctgctgaccg agcgaatcat gcgggagatt   180
gagcgagatc ccgttctcaa cgtcgccggc gactacgacg ccgatcttcc caccaagcga   240
cgacaagctg ttgagcgaat cggggctctg gcccgatacc tgcccaagga ttccgagaag   300
gaggccattt tgcgaggcca gctgcatggt attgtggaca tgggtacccg aacccgaatc   360
gccgttcact acggtctgtt tatgggcgcc attcgtggct caggaaccaa ggagcagtac   420

-continued

```
gattactggg tcgccaaggg cgccgctact ctgcacaaat tctatggctg ctttgccatg    480
actgagctgg gtcacggatc taacgtggcc ggtctcgaga ccaccgccac ccttgataag    540
gacaccgacg agttcatcat caacacccc aactcgggag ccacaaagtg gtggattgga    600
ggagctgccc actctgctac ccacacggct tgtcttgccc gactcattgt tgatggcaag    660
gactatggtg ttaagatctt cattgttcag ctgcgagacc tcaactccca ctctctactc    720
aacggtattg ccattggaga tatcggcaag aagatgggcc gagatgccat tgataatggt    780
tggatccagt tcacagacgt ccgaattccc cgacagaaca tgctcatgcg atacgaccgg    840
gtgtctcgag acggcgaggt taccacctcc gagcttgccc agctcaccta cggagcactt    900
ctgtctggcc gagtgaccat gattgccgag tctcacctcc tgtctgctcg gttcctcacc    960
attgctcttc ggtacgcctg tatccgtcga cagttcggag ctgtgcctga caagcccgag   1020
actaagctca tcgactaccc ctaccaccaa cgacgtctgc tgcctcttct ggcctacacc   1080
tacgccatga agatgggcgc cgacgaggcc cagcagcagt acaactcctc ctttggcgct   1140
cttctcaagc tcaaccccgt caaggacgct gagaagtttg ctgtcgccac tgccgacctc   1200
aaggctctgt ttgcctcttc tgccggaatg aaggccttca ccacctgggc tgccgccaag   1260
atcattgacg agtgccgaca ggcctgtggt ggccatggct actccggcta caacggtttc   1320
ggtcaggctt acgccgactg ggtcgtccaa tgcacttggg agggtgacaa caacgtgctg   1380
tgtctgtcca tgggtcgatc gctcatccag tcgtgcattg ccatgagaaa aagaagggc   1440
catgtcggca agtcggtcga gtacctgcag cgacgagacg agctgcagaa tgcccgagtt   1500
gacaacaagc ctctcactga ccctgctgtg ctcatcactg catgggagaa ggttgcctgc   1560
gaggccatca acagagccac tgactccttc atcaagctca cccaggaggg tctgtctcct   1620
gaccaggcct ttgaggagct gtctcaacag agatttgagt gtgcgcgaat ccacacccga   1680
aagcatctga tcacctcgtt ctacgctcga atctccaagg ccaaggcccg agtcaagccc   1740
caccttactg ttcttgccaa cctctttgcc gtctggtcca tcgaggagga ctctggtctc   1800
ttccttcggg agggctgctt cgagcctgcc gagatggacg agatcaccgc tctggtcgac   1860
gagctgtgct gcgaggctcg agagcaggtc attggattca ccgacgcctt caacctgtcc   1920
gacttcttca ttaacgcccc cattggccga ttcgacggag acgcctacaa gcactacatg   1980
gacgaggtca aggctgccaa caaccctcgt aacacccatg ctccttacta cgagaccaag   2040
ctgcgacccct tcctgttccg acccgatgag gacgaggaga tttgcgacct ggacgagtag   2100
```

<210> SEQ ID NO 41
<211> LENGTH: 699
<212> TYPE: PRT
<213> ORGANISM: Yarrowia lipolytica
<220> FEATURE:
<221> NAME/KEY: MISC_FEATURE
<223> OTHER INFORMATION: acyl-coenzyme A oxidase POX5

<400> SEQUENCE: 41

```
Met Asn Asn Asn Pro Thr Asn Val Ile Leu Gly Gly Lys Glu Tyr Asp
1               5                   10                  15

Thr Phe Thr Glu Pro Pro Ala Gln Met Glu Leu Glu Arg Ala Lys Thr
            20                  25                  30

Gln Phe Lys Val Arg Asp Val Thr Asn Phe Leu Thr Gly Ser Glu Gln
        35                  40                  45

Glu Thr Leu Leu Thr Glu Arg Ile Met Arg Glu Ile Glu Arg Asp Pro
    50                  55                  60
```

```
Val Leu Asn Val Ala Gly Asp Tyr Asp Ala Asp Leu Pro Thr Lys Arg
 65                  70                  75                  80

Arg Gln Ala Val Glu Arg Ile Gly Ala Leu Ala Arg Tyr Leu Pro Lys
                 85                  90                  95

Asp Ser Glu Lys Glu Ala Ile Leu Arg Gly Gln Leu His Gly Ile Val
            100                 105                 110

Asp Met Gly Thr Arg Thr Arg Ile Ala Val His Tyr Gly Leu Phe Met
        115                 120                 125

Gly Ala Ile Arg Gly Ser Gly Thr Lys Glu Gln Tyr Asp Tyr Trp Val
    130                 135                 140

Ala Lys Gly Ala Ala Thr Leu His Lys Phe Tyr Gly Cys Phe Ala Met
145                 150                 155                 160

Thr Glu Leu Gly His Gly Ser Asn Val Ala Gly Leu Glu Thr Thr Ala
                165                 170                 175

Thr Leu Asp Lys Asp Thr Asp Glu Phe Ile Ile Asn Thr Pro Asn Ser
            180                 185                 190

Gly Ala Thr Lys Trp Trp Ile Gly Gly Ala Ala His Ser Ala Thr His
        195                 200                 205

Thr Ala Cys Leu Ala Arg Leu Ile Val Asp Gly Lys Asp Tyr Gly Val
    210                 215                 220

Lys Ile Phe Ile Val Gln Leu Arg Asp Leu Asn Ser His Ser Leu Leu
225                 230                 235                 240

Asn Gly Ile Ala Ile Gly Asp Ile Gly Lys Lys Met Gly Arg Asp Ala
                245                 250                 255

Ile Asp Asn Gly Trp Ile Gln Phe Thr Asp Val Arg Ile Pro Arg Gln
            260                 265                 270

Asn Met Leu Met Arg Tyr Asp Arg Val Ser Arg Asp Gly Glu Val Thr
        275                 280                 285

Thr Ser Glu Leu Ala Gln Leu Thr Tyr Gly Ala Leu Leu Ser Gly Arg
    290                 295                 300

Val Thr Met Ile Ala Glu Ser His Leu Leu Ser Ala Arg Phe Leu Thr
305                 310                 315                 320

Ile Ala Leu Arg Tyr Ala Cys Ile Arg Arg Gln Phe Gly Ala Val Pro
                325                 330                 335

Asp Lys Pro Glu Thr Lys Leu Ile Asp Tyr Pro Tyr His Gln Arg Arg
            340                 345                 350

Leu Leu Pro Leu Leu Ala Tyr Thr Tyr Ala Met Lys Met Gly Ala Asp
        355                 360                 365

Glu Ala Gln Gln Gln Tyr Asn Ser Ser Phe Gly Ala Leu Leu Lys Leu
    370                 375                 380

Asn Pro Val Lys Asp Ala Glu Lys Phe Ala Val Ala Thr Ala Asp Leu
385                 390                 395                 400

Lys Ala Leu Phe Ala Ser Ser Ala Gly Met Lys Ala Phe Thr Thr Trp
                405                 410                 415

Ala Ala Ala Lys Ile Ile Asp Glu Cys Arg Gln Ala Cys Gly Gly His
            420                 425                 430

Gly Tyr Ser Gly Tyr Asn Gly Phe Gly Gln Ala Tyr Ala Asp Trp Val
        435                 440                 445

Val Gln Cys Thr Trp Glu Gly Asp Asn Asn Val Leu Cys Leu Ser Met
    450                 455                 460

Gly Arg Ser Leu Ile Gln Ser Cys Ile Ala Met Arg Lys Lys Lys Gly
465                 470                 475                 480
```

```
His Val Gly Lys Ser Val Glu Tyr Leu Gln Arg Arg Asp Glu Leu Gln
                485                 490                 495

Asn Ala Arg Val Asp Asn Lys Pro Leu Thr Asp Pro Ala Val Leu Ile
            500                 505                 510

Thr Ala Trp Glu Lys Val Ala Cys Glu Ala Ile Asn Arg Ala Thr Asp
        515                 520                 525

Ser Phe Ile Lys Leu Thr Gln Glu Gly Leu Ser Pro Asp Gln Ala Phe
    530                 535                 540

Glu Glu Leu Ser Gln Gln Arg Phe Glu Cys Ala Arg Ile His Thr Arg
545                 550                 555                 560

Lys His Leu Ile Thr Ser Phe Tyr Ala Arg Ile Ser Lys Ala Lys Ala
                565                 570                 575

Arg Val Lys Pro His Leu Thr Val Leu Ala Asn Leu Phe Ala Val Trp
            580                 585                 590

Ser Ile Glu Glu Asp Ser Gly Leu Phe Leu Arg Glu Gly Cys Phe Glu
        595                 600                 605

Pro Ala Glu Met Asp Glu Ile Thr Ala Leu Val Asp Glu Leu Cys Cys
    610                 615                 620

Glu Ala Arg Glu Gln Val Ile Gly Phe Thr Asp Ala Phe Asn Leu Ser
625                 630                 635                 640

Asp Phe Phe Ile Asn Ala Pro Ile Gly Arg Phe Asp Gly Asp Ala Tyr
                645                 650                 655

Lys His Tyr Met Asp Glu Val Lys Ala Ala Asn Pro Arg Asn Thr
            660                 665                 670

His Ala Pro Tyr Tyr Glu Thr Lys Leu Arg Pro Phe Leu Phe Arg Pro
        675                 680                 685

Asp Glu Asp Glu Glu Ile Cys Asp Leu Asp Glu
    690                 695

<210> SEQ ID NO 42
<211> LENGTH: 1752
<212> TYPE: DNA
<213> ORGANISM: Escherichia coli
<220> FEATURE:
<221> NAME/KEY: misc_feature
<223> OTHER INFORMATION: acyl-coenzyme A oxidase, FadD

<400> SEQUENCE: 42
atgttaacag tatgtttatc acttgggggtt gcgatgacga cgaacgcgca ttttagaggt     60
gaagaattga agaaggtttg gcttaaccgt tatcccgcgg acgttccgac ggagatcaac    120
cctgaccgtt atcaatctct ggtagatatg tttgagcagt cggtcgcgcg ctacgccgat    180
caacccgcgt tgtgaatat gggggaggtg atgaccttcc gcaaactgga agaacgcagt    240
cgcgcgtttg ccgcttattt gcaacaaggg ttggggctga agaaggcga tcgcgttgcg    300 ttgatgatgc taacttatt gcaatatccg gtggcgctgt ttggcatttt cgtgccggg     360 atgatcgtcg taaacgttaa cccgttgtat accccgcgtg agcttgagca tcagcttaac    420
gatagcggcg catcggcgat tgttatcgtg tctaactttg cccacactct ggaaaaagtg    480
gttgataaaa ccgccgttca gcacgttatt ctgacccgta tgggcgatca gctatctacg    540
gcaaaaggca cggtagtcaa tttcgttgtt aaatacatca agcgtctggt gccgaaatac    600
catctgccag atgccatttc atttcgtagc gccctgcaca acggctaccg gatgcagtac    660
gtcaaaccag aactggtgcc ggaagattta gcttcctgc aatacaccgg cggcaccact    720
ggtgtggcga aggcgcgat gctgactcac cgcaatatgc tggcgaacct ggaacaggtt    780
```

-continued

```
aacgcgacct atggtccgct gttgcatccg ggcaaagagc tggtggtgac ggcgctgccg      840
ctgtatcaca tttttgcact gaccattaac tgcctgctgt ttatcgaact gggggggcag      900
aacctgctta tcactaaccc gcgcgatatt ccagggctgg taaaagagtt agcgaaatat      960
ccgtttaccg ctatcactgg cgttaacacc ttgttcaatg cgttgctgaa caataaagag     1020
ttccagcagc tggatttctc cagtctgcat ctttccgcag gcggtgggat gcctgttcag     1080
caagtggttg cagaacgttg ggttaaactg actggacagt atctgctgga aggttatggc     1140
ctgaccgagt gcgcgccgct ggtcagcgtt aacccgtatg atattgatta tcatagtggt     1200
agcatcggtt taccggtgcc gtcgacggaa gccaaactgg tggatgatga tgataatgaa     1260
gtaccacctg gtcaaccagg tgagctttgt gtcaaggac cgcaggtgat gctgggttac     1320
tggcagcgtc cggatgctac cgatgaaatc atcaaaaatg gctggttaca caccggcgac     1380
atcgcggtga tggatgaaga aggattcctg cgcattgtcg atcgtaaaaa agacatgatt     1440
ctggtttccg gttttaacgt ttatcccaac gagattgaag atgtcgtcat gcagcatcct     1500
ggcgtacagg aagtcgcggc tgttggcgta ccttccggct ccagtggtga agcggtgaaa     1560
atcttcgtag tgaaaaaaga tccatcgctt accgaagagt cactggtgac cttttgccgc     1620
cgtcagctca cgggctacaa agtaccgaag ctggtggagt tcgtgatga gttaccgaaa     1680 tctaacgtcg gaaaattttt gcgacgagaa ttacgtgacg aagcgcgcgg caaagtggac     1740
aataaagcct ga                                                         1752
```

<210> SEQ ID NO 43
<211> LENGTH: 583
<212> TYPE: PRT
<213> ORGANISM: Escherichia coli
<220> FEATURE:
<221> NAME/KEY: MISC_FEATURE
<223> OTHER INFORMATION: acyl-coenzyme A oxidase, FadD

<400> SEQUENCE: 43

```
Met Leu Thr Val Cys Leu Ser Leu Gly Val Ala Met Thr Thr Asn Ala
1               5                   10                  15

His Phe Arg Gly Glu Glu Leu Lys Lys Val Trp Leu Asn Arg Tyr Pro
            20                  25                  30

Ala Asp Val Pro Thr Glu Ile Asn Pro Asp Arg Tyr Gln Ser Leu Val
        35                  40                  45

Asp Met Phe Glu Gln Ser Val Ala Arg Tyr Ala Asp Gln Pro Ala Phe
    50                  55                  60

Val Asn Met Gly Glu Val Met Thr Phe Arg Lys Leu Glu Glu Arg Ser
65                  70                  75                  80

Arg Ala Phe Ala Ala Tyr Leu Gln Gln Gly Leu Gly Leu Lys Lys Gly
                85                  90                  95

Asp Arg Val Ala Leu Met Met Pro Asn Leu Leu Gln Tyr Pro Val Ala
            100                 105                 110

Leu Phe Gly Ile Leu Arg Ala Gly Met Ile Val Val Asn Val Asn Pro
        115                 120                 125

Leu Tyr Thr Pro Arg Glu Leu Glu His Gln Leu Asn Asp Ser Gly Ala
    130                 135                 140

Ser Ala Ile Val Ile Val Ser Asn Phe Ala His Thr Leu Glu Lys Val
145                 150                 155                 160

Val Asp Lys Thr Ala Val Gln His Val Ile Leu Thr Arg Met Gly Asp
                165                 170                 175

Gln Leu Ser Thr Ala Lys Gly Thr Val Val Asn Phe Val Val Lys Tyr
```

```
            180             185                 190
Ile Lys Arg Leu Val Pro Lys Tyr His Leu Pro Asp Ala Ile Ser Phe
            195                 200                 205

Arg Ser Ala Leu His Asn Gly Tyr Arg Met Gln Tyr Val Lys Pro Glu
    210                 215                 220

Leu Val Pro Glu Asp Leu Ala Phe Leu Gln Tyr Thr Gly Gly Thr Thr
225                 230                 235                 240

Gly Val Ala Lys Gly Ala Met Leu Thr His Arg Asn Met Leu Ala Asn
                245                 250                 255

Leu Glu Gln Val Asn Ala Thr Tyr Gly Pro Leu Leu His Pro Gly Lys
            260                 265                 270

Glu Leu Val Val Thr Ala Leu Pro Leu Tyr His Ile Phe Ala Leu Thr
        275                 280                 285

Ile Asn Cys Leu Leu Phe Ile Glu Leu Gly Gly Gln Asn Leu Leu Ile
    290                 295                 300

Thr Asn Pro Arg Asp Ile Pro Gly Leu Val Lys Glu Leu Ala Lys Tyr
305                 310                 315                 320

Pro Phe Thr Ala Ile Thr Gly Val Asn Thr Leu Phe Asn Ala Leu Leu
                325                 330                 335

Asn Asn Lys Glu Phe Gln Gln Leu Asp Phe Ser Ser Leu His Leu Ser
            340                 345                 350

Ala Gly Gly Gly Met Pro Val Gln Gln Val Val Ala Glu Arg Trp Val
        355                 360                 365

Lys Leu Thr Gly Gln Tyr Leu Leu Glu Gly Tyr Gly Leu Thr Glu Cys
    370                 375                 380

Ala Pro Leu Val Ser Val Asn Pro Tyr Asp Ile Asp Tyr His Ser Gly
385                 390                 395                 400

Ser Ile Gly Leu Pro Val Pro Ser Thr Glu Ala Lys Leu Val Asp Asp
                405                 410                 415

Asp Asp Asn Glu Val Pro Pro Gly Gln Pro Gly Glu Leu Cys Val Lys
            420                 425                 430

Gly Pro Gln Val Met Leu Gly Tyr Trp Gln Arg Pro Asp Ala Thr Asp
        435                 440                 445

Glu Ile Ile Lys Asn Gly Trp Leu His Thr Gly Asp Ile Ala Val Met
450                 455                 460

Asp Glu Glu Gly Phe Leu Arg Ile Val Asp Arg Lys Lys Asp Met Ile
465                 470                 475                 480

Leu Val Ser Gly Phe Asn Val Tyr Pro Asn Glu Ile Glu Asp Val Val
                485                 490                 495

Met Gln His Pro Gly Val Gln Glu Val Ala Ala Val Gly Val Pro Ser
            500                 505                 510

Gly Ser Ser Gly Glu Ala Val Lys Ile Phe Val Val Lys Lys Asp Pro
        515                 520                 525

Ser Leu Thr Glu Glu Ser Leu Val Thr Phe Cys Arg Arg Gln Leu Thr
    530                 535                 540

Gly Tyr Lys Val Pro Lys Leu Val Glu Phe Arg Asp Glu Leu Pro Lys
545                 550                 555                 560

Ser Asn Val Gly Lys Ile Leu Arg Arg Glu Leu Arg Asp Glu Ala Arg
                565                 570                 575

Gly Lys Val Asp Asn Lys Ala
            580

<210> SEQ ID NO 44
```

<211> LENGTH: 1959
<212> TYPE: DNA
<213> ORGANISM: Escherichia coli
<220> FEATURE:
<221> NAME/KEY: misc_feature
<223> OTHER INFORMATION: Adenosine monophosphate (AMP)-forming acetyl-CoA synthetase

<400> SEQUENCE: 44

```
atgagccaaa ttcacaaaca caccattcct gccaacatcg cagaccgttg cctgataaac      60
cctcagcagt acgaggcgat gtatcaacaa tctattaacg tacctgatac cttctggggc     120
gaacagggaa aaattcttga ctggatcaaa ccttaccaga aggtgaaaaa cacctccttt     180
gcccccggta atgtgtccat taaatggtac gaggacggca cgctgaatct ggcggcaaac     240
tgccttgacc gccatctgca agaaaacggc gatcgtaccg ccatcatctg gaaggcgac      300
gacgccagcc agagcaaaca tatcagctat aaagagctgc accgcgacgt ctgccgcttc     360
gccaataccc tgctcgagct gggcattaaa aaggtgatg tggtggcgat ttatatgccg      420
atggtgccgg aagccgcggt tgcgatgctg gcctgcgccc gcattggcgc ggtgcattcg     480
gtgattttcg gcggcttctc gccggaagcc gttgccgggc gcattattga ttccaactca     540
cgactggtga tcacttccga cgaaggtgtg cgtgccgggc gagtattcc gctgaagaaa      600
aacgttgatg acgcgctgaa aaacccgaac gtcaccagcg tagagcatgt ggtggtactg     660
aagcgtactg cgggaaaaat tgactggcag gaagggcgcg acctgtggtg gcacgacctg     720
gttgagcaag cgagcgatca gcaccaggcg gaagagatga acgccgaaga tccgctgttt     780
attctctaca cctccggttc taccggtaag ccaaaaggtg tgctgcatac taccggcggt     840
tatctggtgt acgcggcgct gacctttaaa tatgtctttg attatcatcc gggtgatatc     900
tactggtgca ccgccgatgt gggctgggtg accggacaca gttacttgct gtacggcccg     960
ctggcctgcg gtgcgaccac gctgatgttt gaaggcgtac cgaactggcc gacgcctgcc    1020
cgtatggcgc aggtggtgga caagcatcag gtcaatattc tctataccgc gcccacggcg    1080
attcgcgcgc tgatggcgga aggggataaa gcgattgaag caccgaccg atcgtcgctg      1140
cgcattctcg gttccgtggg cgagccaatc aacccggaag cgtgggagtg gtactggaaa    1200
aaaatcggca acgagaaatg tccggtggtc gataccggt ggcagaccga actggcggt      1260
ttcatgatca cgccgctgcc tggcgctacc gagctgaaag ccggttcggc aacacgtccg    1320
ttcttcggcg tgcaaccggc gctggtcgat aacgaaggta accgctgga aggcgctacc     1380
gaaggcagcc tggtgatcac cgactcctgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg ggcgtgtgga cgatgtgctg    1560
aacgtctccg gtcaccgtct gggaacggcg gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aaacccgctc cggcaaaatt atgcgccgta ttctgcgcaa aattgcggcg    1860
ggcgatacca gcaacctggg cgatacctcg acgcttgccg atcctggcgt agtcgagaag    1920
ctgcttgaag agaagcaggc tatcgcgatg ccatcgtaa                          1959
```

<210> SEQ ID NO 45
<211> LENGTH: 652

<210> TYPE: PRT
<213> ORGANISM: Escherichia coli
<220> FEATURE:
<221> NAME/KEY: MISC_FEATURE
<223> OTHER INFORMATION: Adenosine monophosphate (AMP)-forming acetyl-CoA synthetase

<400> SEQUENCE: 45

```
Met Ser Gln Ile His Lys His Thr Ile Pro Ala Asn Ile Ala Asp Arg
1               5                   10                  15
Cys Leu Ile Asn Pro Gln Gln Tyr Glu Ala Met Tyr Gln Gln Ser Ile
                20                  25                  30
Asn Val Pro Asp Thr Phe Trp Gly Glu Gln Gly Lys Ile Leu Asp Trp
            35                  40                  45
Ile Lys Pro Tyr Gln Lys Val Lys Asn Thr Ser Phe Ala Pro Gly Asn
50                  55                  60
Val Ser Ile Lys Trp Tyr Glu Asp Gly Thr Leu Asn Leu Ala Ala Asn
65                  70                  75                  80
Cys Leu Asp Arg His Leu Gln Glu Asn Gly Asp Arg Thr Ala Ile Ile
                85                  90                  95
Trp Glu Gly Asp Asp Ala Ser Gln Ser Lys His Ile Ser Tyr Lys Glu
            100                 105                 110
Leu His Arg Asp Val Cys Arg Phe Ala Asn Thr Leu Leu Glu Leu Gly
        115                 120                 125
Ile Lys Lys Gly Asp Val Val Ala Ile Tyr Met Pro Met Val Pro Glu
130                 135                 140
Ala Ala Val Ala Met Leu Ala Cys Ala Arg Ile Gly Ala Val His Ser
145                 150                 155                 160
Val Ile Phe Gly Gly Phe Ser Pro Glu Ala Val Ala Gly Arg Ile Ile
                165                 170                 175
Asp Ser Asn Ser Arg Leu Val Ile Thr Ser Asp Glu Gly Val Arg Ala
            180                 185                 190
Gly Arg Ser Ile Pro Leu Lys Lys Asn Val Asp Asp Ala Leu Lys Asn
        195                 200                 205
Pro Asn Val Thr Ser Val Glu His Val Val Val Leu Lys Arg Thr Gly
210                 215                 220
Gly Lys Ile Asp Trp Gln Glu Gly Arg Asp Leu Trp Trp His Asp Leu
225                 230                 235                 240
Val Glu Gln Ala Ser Asp Gln His Gln Ala Glu Met Asn Ala Glu
                245                 250                 255
Asp Pro Leu Phe Ile Leu Tyr Thr Ser Gly Ser Thr Gly Lys Pro Lys
            260                 265                 270
Gly Val Leu His Thr Thr Gly Gly Tyr Leu Val Tyr Ala Ala Leu Thr
        275                 280                 285
Phe Lys Tyr Val Phe Asp Tyr His Pro Gly Asp Ile Tyr Trp Cys Thr
290                 295                 300
Ala Asp Val Gly Trp Val Thr Gly His Ser Tyr Leu Leu Tyr Gly Pro
305                 310                 315                 320
Leu Ala Cys Gly Ala Thr Thr Leu Met Phe Glu Gly Val Pro Asn Trp
                325                 330                 335
Pro Thr Pro Ala Arg Met Ala Gln Val Val Asp Lys His Gln Val Asn
            340                 345                 350
Ile Leu Tyr Thr Ala Pro Thr Ala Ile Arg Ala Leu Met Ala Glu Gly
        355                 360                 365
Asp Lys Ala Ile Glu Gly Thr Asp Arg Ser Ser Leu Arg Ile Leu Gly
```

```
        370               375               380
Ser Val Gly Glu Pro Ile Asn Pro Glu Ala Trp Glu Trp Tyr Trp Lys
385                   390                   395                 400

Lys Ile Gly Asn Glu Lys Cys Pro Val Val Asp Thr Trp Trp Gln Thr
                405                   410                   415

Glu Thr Gly Gly Phe Met Ile Thr Pro Leu Pro Gly Ala Thr Glu Leu
                420                   425                   430

Lys Ala Gly Ser Ala Thr Arg Pro Phe Phe Gly Val Gln Pro Ala Leu
                435                   440                   445

Val Asp Asn Glu Gly Asn Pro Leu Glu Gly Ala Thr Glu Gly Ser Leu
450                   455                   460

Val Ile Thr Asp Ser Trp Pro Gly Gln Ala Arg Thr Leu Phe Gly Asp
465                   470                   475                 480

His Glu Arg Phe Glu Gln Thr Tyr Phe Ser Thr Phe Lys Asn Met Tyr
                485                   490                   495

Phe Ser Gly Asp Gly Ala Arg Arg Asp Glu Asp Gly Tyr Tyr Trp Ile
                500                   505                   510

Thr Gly Arg Val Asp Asp Val Leu Asn Val Ser Gly His Arg Leu Gly
                515                   520                   525

Thr Ala Glu Ile Glu Ser Ala Leu Val Ala His Pro Lys Ile Ala Glu
530                   535                   540

Ala Ala Val Val Gly Ile Pro His Asn Ile Lys Gly Gln Ala Ile Tyr
545                   550                   555                 560

Ala Tyr Val Thr Leu Asn His Gly Glu Glu Pro Ser Pro Glu Leu Tyr
                565                   570                   575

Ala Glu Val Arg Asn Trp Val Arg Lys Glu Ile Gly Pro Leu Ala Thr
                580                   585                   590

Pro Asp Val Leu His Trp Thr Asp Ser Leu Pro Lys Thr Arg Ser Gly
                595                   600                   605

Lys Ile Met Arg Arg Ile Leu Arg Lys Ile Ala Ala Gly Asp Thr Ser
610                   615                   620

Asn Leu Gly Asp Thr Ser Thr Leu Ala Asp Pro Gly Val Val Glu Lys
625                   630                   635                 640

Leu Leu Glu Glu Lys Gln Ala Ile Ala Met Pro Ser
                645                   650
```

<210> SEQ ID NO 46
<211> LENGTH: 1689
<212> TYPE: DNA
<213> ORGANISM: Escherichia coli
<220> FEATURE:
<221> NAME/KEY: misc_feature
<223> OTHER INFORMATION: acyl-CoA synthetase

<400> SEQUENCE: 46

```
atgcgctatg ccgatttttcc aacgctggtt gatgctttgg actacgccgc tctgagtagc      60
gccggaatga attttatga cagacgttgc caacttgaag atcaactgga atatcagaca       120
ttaaaaacgc gtgccgaagc tggtgcgaag cggttgttat cgctgaacct gaaaaaaggc      180
gatcgcgtgg cactgattgc cgaaacaagt agcgggttcg tagaggcttt ttttgcctgc     240
cagtatgccg gcttagtcgc cgtcccgttg gcgattccaa tgggcgttgg tcagcgggat     300
tcctggagcg ccaaattgca gggtttactg gcaagttgcc agcccgcagc cattatcact     360
ggtgatgagt ggttgccact ggtcaatgcc gcgacgcatg acaacccccga attacatgtt    420
ttaagccacg cctggtttaa ggcattaccg gaagccgatg ttgcgctcca gcgtccagtt     480
```

```
ccgaacgata tcgcctacct ccagtacacc tccggcagca cccgttttcc cgtggcgtc      540
attatcaccc atcgcgaagt gatggctaat ctacgtgcta taagccacga cggcattaaa      600
ttacgccctg cgaccgctg cgtctcctgg ctgcctttct accatgatat gggactggtc       660
ggctttctcc tgaccccgt cgccacgcag ctttcagtag attatttgcg cactcaggat       720
tttgccatgc gtcctctgca atggcttaaa ttgatcagta aaatcgcgg caccgttttcc      780
gttgcgccgc cgtttggcta tgaattgtgc cagcgccgcg tgaatgaaaa agatctcgct      840
gaactggatc tttcctgctg gcgcgtcgct ggtattggtg cagaacccat ctccgcagaa      900
caactccatc aattcgctga atgtttccgt caggttaact ttgacaataa aactttcatg      960
ccgtgctacg gactggcaga aaatgcgctg gctgtcagct tctctgatga agcctccggg     1020
gttgtggtta acgaagtgga tcgcgacatc ctcgaatatc agggtaaagc cgtcgcgccg     1080
ggtgcagaga cacgcgccgt atcgactttc gtcaactgcg gcaaagcgtt gccggaacat     1140
ggtattgaaa tccgcaatga agcaggtatg ccggtcgcgg aacgtgtggt aggccatatt     1200
tgcatctccg gtcccagtct gatgagcggt tactttggcg accaggcttc gcaagacgag     1260
attgccgcga cgggctggtt agacaccggc gacctcggtt atctgctgga cggttatctg     1320
tatgtcaccg gacgcattaa agatctgatt attattcgtg gccgtaatat ctggccgcag     1380
gatattgaat atattgcgga caagaaccg gaaattcatt ctggcgatgc gattgctttt     1440
gttaccgccc aggaaaaaat cattttgcag atccagtgtc ggatcagcga cgaagaacgt     1500
cgcgggcagc ttatccacgc gctggcggca cggatccaaa gcgaatttgg cgtgaccgcg     1560
gctatcgagc tgttgccgcc ccacagtatt ccccgaacgt cctccggcaa gcctgcccgt     1620
gcggaagcga aaaacgtta tcagaaggct tatgctgcca gtcttcatgt gcaggaatcc      1680
ctggcatga                                                             1689
```

<210> SEQ ID NO 47
<211> LENGTH: 562
<212> TYPE: PRT
<213> ORGANISM: Escherichia coli
<220> FEATURE:
<221> NAME/KEY: MISC_FEATURE
<223> OTHER INFORMATION: acyl-CoA synthetase

<400> SEQUENCE: 47

```
Met Arg Tyr Ala Asp Phe Pro Thr Leu Val Asp Ala Leu Asp Tyr Ala
1               5                   10                  15

Ala Leu Ser Ser Ala Gly Met Asn Phe Tyr Asp Arg Arg Cys Gln Leu
            20                  25                  30

Glu Asp Gln Leu Glu Tyr Gln Thr Leu Lys Thr Arg Ala Glu Ala Gly
        35                  40                  45

Ala Lys Arg Leu Leu Ser Leu Asn Leu Lys Lys Gly Asp Arg Val Ala
    50                  55                  60

Leu Ile Ala Glu Thr Ser Ser Gly Phe Val Glu Ala Phe Phe Ala Cys
65                  70                  75                  80

Gln Tyr Ala Gly Leu Val Ala Val Pro Leu Ala Ile Pro Met Gly Val
            85                  90                  95

Gly Gln Arg Asp Ser Trp Ser Ala Lys Leu Gln Gly Leu Leu Ala Ser
            100                 105                 110

Cys Gln Pro Ala Ala Ile Ile Thr Gly Asp Glu Trp Leu Pro Leu Val
        115                 120                 125

Asn Ala Ala Thr His Asp Asn Pro Glu Leu His Val Leu Ser His Ala
```

```
            130                 135                 140
Trp Phe Lys Ala Leu Pro Glu Ala Asp Val Ala Leu Gln Arg Pro Val
145                 150                 155                 160

Pro Asn Asp Ile Ala Tyr Leu Gln Tyr Thr Ser Gly Ser Thr Arg Phe
                165                 170                 175

Pro Arg Gly Val Ile Ile Thr His Arg Glu Val Met Ala Asn Leu Arg
            180                 185                 190

Ala Ile Ser His Asp Gly Ile Lys Leu Arg Pro Gly Asp Arg Cys Val
        195                 200                 205

Ser Trp Leu Pro Phe Tyr His Asp Met Gly Leu Val Gly Phe Leu Leu
    210                 215                 220

Thr Pro Val Ala Thr Gln Leu Ser Val Asp Tyr Leu Arg Thr Gln Asp
225                 230                 235                 240

Phe Ala Met Arg Pro Leu Gln Trp Leu Lys Leu Ile Ser Lys Asn Arg
                245                 250                 255

Gly Thr Val Ser Val Ala Pro Pro Phe Gly Tyr Glu Leu Cys Gln Arg
            260                 265                 270

Arg Val Asn Glu Lys Asp Leu Ala Glu Leu Asp Leu Ser Cys Trp Arg
        275                 280                 285

Val Ala Gly Ile Gly Ala Glu Pro Ile Ser Ala Glu Gln Leu His Gln
    290                 295                 300

Phe Ala Glu Cys Phe Arg Gln Val Asn Phe Asp Asn Lys Thr Phe Met
305                 310                 315                 320

Pro Cys Tyr Gly Leu Ala Glu Asn Ala Leu Ala Val Ser Phe Ser Asp
                325                 330                 335

Glu Ala Ser Gly Val Val Asn Glu Val Asp Arg Asp Ile Leu Glu
            340                 345                 350

Tyr Gln Gly Lys Ala Val Ala Pro Gly Ala Glu Thr Arg Ala Val Ser
        355                 360                 365

Thr Phe Val Asn Cys Gly Lys Ala Leu Pro Glu His Gly Ile Glu Ile
    370                 375                 380

Arg Asn Glu Ala Gly Met Pro Val Ala Glu Arg Val Val Gly His Ile
385                 390                 395                 400

Cys Ile Ser Gly Pro Ser Leu Met Ser Gly Tyr Phe Gly Asp Gln Ala
                405                 410                 415

Ser Gln Asp Glu Ile Ala Ala Thr Gly Trp Leu Asp Thr Gly Asp Leu
            420                 425                 430

Gly Tyr Leu Leu Asp Gly Tyr Leu Tyr Val Thr Gly Arg Ile Lys Asp
        435                 440                 445

Leu Ile Ile Ile Arg Gly Arg Asn Ile Trp Pro Gln Asp Ile Glu Tyr
    450                 455                 460

Ile Ala Glu Gln Glu Pro Glu Ile His Ser Gly Asp Ala Ile Ala Phe
465                 470                 475                 480

Val Thr Ala Gln Glu Lys Ile Ile Leu Gln Ile Gln Cys Arg Ile Ser
                485                 490                 495

Asp Glu Glu Arg Arg Gly Gln Leu Ile His Ala Leu Ala Ala Arg Ile
            500                 505                 510

Gln Ser Glu Phe Gly Val Thr Ala Ala Ile Glu Leu Leu Pro Pro His
        515                 520                 525

Ser Ile Pro Arg Thr Ser Ser Gly Lys Pro Ala Arg Ala Glu Ala Lys
    530                 535                 540

Lys Arg Tyr Gln Lys Ala Tyr Ala Ala Ser Leu His Val Gln Glu Ser
545                 550                 555                 560
```

Leu Ala

<210> SEQ ID NO 48
<211> LENGTH: 1284
<212> TYPE: DNA
<213> ORGANISM: Escherichia coli
<220> FEATURE:
<221> NAME/KEY: misc_feature
<223> OTHER INFORMATION: citric synthetase

<400> SEQUENCE: 48

```
atggctgata caaaagcaaa actcaccctc aacggggata cagctgttga actggatgtg      60
ctgaaaggca cgctgggtca agatgttatt gatatccgta ctctcggttc aaaaggtgtg     120
ttcacctttg acccaggctt cacttcaacc gcatcctgcg aatctaaaat tactttttatt    180
gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat ttaaaactac ggtgacccgt cataccatga tccacgagca gattacccgt     360
ctgttccatg ctttccgtcg cgactcgcat ccaatggcag tcatgtgtgg tattaccggc     420
gcgctggcgg cgttctatca cgactcgctg atgttaaca atcctcgtca ccgtgaaatt      480
gccgcgttcc gcctgctgtc gaaaatgccg accatggccg cgatgtgtta caagtattcc     540
attggtcagc catttgttta cccgcgcaac gatctctcct acgccggtaa cttcctgaat     600
atgatgttct ccacgccgtg cgaaccgtat gaagttaatc cgattctgga acgtgctatg     660
gaccgtattc tgatcctgca cgctgaccat gaacagaacg cctctacctc caccgtgcgt     720
accgctggct cttcgggtgc gaacccgttt gcctgtatcg cagcaggtat tgcttcactg     780
tggggacctg cgcacggcgg tgctaacgaa gcggcgctga aaatgctgga agaaatcagc     840
tccgttaaac acattccgga atttgttcgt cgtgcgaaag acaaaaatga ttcttttccgc    900
ctgatgggct tcggtcaccg cgtgtacaaa aattacgacc cgcgcgccac cgtaatgcgt     960
gaaacctgcc atgaagtgct gaaagagctg ggcacgaagg atgacctgct ggaagtggct    1020
atggagctgg aaaacatcgc gctgaacgac ccgtacttta tcgagaagaa actgtacccg    1080
aacgtcgatt tctactctgg tatcatcctg aaagcgatgg gtattccgtc ttccatgttc    1140
accgtcattt tcgcaatggc acgtaccgtt ggctggatcg cccactggag cgaaatgcac    1200
agtgacggta tgaagattgc cgtccgcgt cagctgtata caggatatga aaaacgcgac      1260
tttaaaagcg atatcaagcg ttaa                                           1284
```

<210> SEQ ID NO 49
<211> LENGTH: 427
<212> TYPE: PRT
<213> ORGANISM: Escherichia coli
<220> FEATURE:
<221> NAME/KEY: MISC_FEATURE
<223> OTHER INFORMATION: citric synthetase

<400> SEQUENCE: 49

Met Ala Asp Thr Lys Ala Lys Leu Thr Leu Asn Gly Asp Thr Ala Val
1               5                  10                  15

Glu Leu Asp Val Leu Lys Gly Thr Leu Gly Gln Asp Val Ile Asp Ile
            20                  25                  30

Arg Thr Leu Gly Ser Lys Gly Val Phe Thr Phe Asp Pro Gly Phe Thr
        35                  40                  45

Ser Thr Ala Ser Cys Glu Ser Lys Ile Thr Phe Ile Asp Gly Asp Glu

```
                50             55             60
Gly Ile Leu Leu His Arg Gly Phe Pro Ile Asp Gln Leu Ala Thr Asp
 65                  70                  75                  80

Ser Asn Tyr Leu Glu Val Cys Tyr Ile Leu Leu Asn Gly Glu Lys Pro
                 85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
            115                 120                 125

Ser His Pro Met Ala Val Met Cys Gly Ile Thr Gly Ala Leu Ala Ala
        130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Val Arg Arg Ala Lys Asp Lys Asn Asp Ser Phe Arg Leu Met Gly Phe
        290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
        355                 360                 365

Ile Leu Lys Ala Met Gly Ile Pro Ser Ser Met Phe Thr Val Ile Phe
370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425

<210> SEQ ID NO 50
<211> LENGTH: 72
<212> TYPE: DNA
<213> ORGANISM: Artificial sequence
<220> FEATURE:
<223> OTHER INFORMATION: Synthetic oligonucleotide
```

```
<400> SEQUENCE: 50
atgcgctatg ccgattttcc aacgctggtt gatgctttgg actacgccgc aattaaccct    60
cactaaaggg cg                                                        72

<210> SEQ ID NO 51
<211> LENGTH: 73
<212> TYPE: DNA
<213> ORGANISM: Artificial sequence
<220> FEATURE:
<223> OTHER INFORMATION: Synthetic oligonucleotide

<400> SEQUENCE: 51
tcatgccagg gattcctgca catgaagact ggcagcataa gccttctgat taatacgact    60
cactataggg ctc                                                       73

<210> SEQ ID NO 52
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 52
atggctgata caaaagcaaa actcaccctc aacggggata cagctgttga aattaaccct    60
cactaaaggg cg                                                        72

<210> SEQ ID NO 53
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 53
taacgcttga tatcgctttt aaagtcgcgt ttttcatatc ctgtatacat aatacgactc    60
actatagggc tc                                                        72
```